US011612570B2

United States Patent
Woodworth et al.

(10) Patent No.: US 11,612,570 B2
(45) Date of Patent: *Mar. 28, 2023

(54) DECREASED ADHESIVITY RECEPTOR-TARGETED NANOPARTICLES FOR FN14-POSITIVE TUMORS

(71) Applicant: UNIVERSITY OF MARYLAND, BALTIMORE, Baltimore, MD (US)

(72) Inventors: Graeme F. Woodworth, Baltimore, MD (US); Jeffrey A. Winkles, Frederick, MD (US); Anthony J. Kim, Clarksville, MD (US); Aniket Wadajkar, Germantown, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/949,198

(22) Filed: Oct. 19, 2020

(65) Prior Publication Data
US 2021/0030689 A1 Feb. 4, 2021

Related U.S. Application Data

(63) Continuation of application No. 16/289,424, filed on Feb. 28, 2019, now Pat. No. 11,045,428, which is a continuation-in-part of application No. 15/528,555, filed as application No. PCT/US2015/061853 on Nov. 20, 2015, now Pat. No. 11,033,637.

(60) Provisional application No. 62/083,011, filed on Nov. 21, 2014.

(51) Int. Cl.
| | |
|---|---|
| *A61K 9/51* | (2006.01) |
| *A61K 9/50* | (2006.01) |
| *C07K 16/28* | (2006.01) |
| *A61K 47/69* | (2017.01) |
| *A61P 35/00* | (2006.01) |
| *A61K 47/68* | (2017.01) |
| *A61K 47/60* | (2017.01) |
| *A61K 31/337* | (2006.01) |
| *A61K 39/00* | (2006.01) |

(52) U.S. Cl.
CPC ............. *A61K 9/51* (2013.01); *A61K 9/5031* (2013.01); *A61K 31/337* (2013.01); *A61K 47/60* (2017.08); *A61K 47/6855* (2017.08); *A61K 47/6921* (2017.08); *A61P 35/00* (2018.01); *C07K 16/2875* (2013.01); *A61K 2039/505* (2013.01); *C07K 2317/55* (2013.01); *C07K 2317/56* (2013.01); *C07K 2317/92* (2013.01)

(58) Field of Classification Search
None
See application file for complete search history.

(56) References Cited

U.S. PATENT DOCUMENTS

| | | |
|---|---|---|
| 2011/0224288 A1 | 9/2011 | Zale et al. |
| 2014/0023715 A1 | 1/2014 | Yang et al. |
| 2014/0044791 A1 | 2/2014 | Basilion et al. |

FOREIGN PATENT DOCUMENTS

WO 2013040499 A1 3/2013

OTHER PUBLICATIONS

Bobo, R.H., et al., "Convection-enhanced delivery of macromolecules in the brain," Proc. Natl. Acad. Sci. USA 1994, pp. 2076-2080, vol. 91.
Brem, H., et al., "Placebo-controlled trial of safety and efficacy of intraoperative controlled delivery by biodegradable polymers of chemotherapy for recurrent gliomas," Lancet 1995, pp. 1008-1012, vol. 345.
Dhruv, H., et al., "Structural basis and targeting of the interaction between fibroblast growth factor-inducible 14 and tumor necrosis factor-like weak inducer of apoptosis," J Biol Chem 2013, pp. 32261-32276, vol. 288, No. 45.
Fung, L.K., et al., "Chemotherapeutic drugs released from polymers: distribution of 1,3-bis(2-chloroethyl)-I-nitrosourea in the rat brain," Pharm Res 1996, pp. 671-682, vol. 13, No. 5.
Kim, A.J., et al., "Use of single-site-functionalized PEG dendrons to prepare gene vectors that penetrate human mucus barriers," Angew. Chem. Int. Ed. 2013, pp. 3985-3988, vol. 52.
Madhankumar, A.B., et al., "Interleukin-13 receptor-targeted nanovesicles are a potential therapy for glioblastoma multiforme," Mol Cancer Ther 2006, pp. 3162-3169, vol. 5, No. 12.
Meighan-Mantha, R.L., et al., "The mitogen-inducible Fn14 gene encodes a type I transmembrane protein that modulates fibroblast adhesion and migration," J Biol Chem 1999, pp. 33166-33176, vol. 274, No. 46.

(Continued)

*Primary Examiner* — Robert A Wax
*Assistant Examiner* — Randeep Singh
(74) *Attorney, Agent, or Firm* — Wolter Van Dyke Davis, PLLC; Eugene J. Molinelli; Martha Cassidy

(57) ABSTRACT

Metastatic triple negative breast cancer (TNBC) still carries a dismal prognosis with the current treatment paradigms. The effectiveness of drug treatment for many solid tumors such as TNBC is limited by tumor heterogeneity, lack of tumor specificity, off-target toxicities, and transient therapeutic action(s). Strategies that provide tumor-specific, sustained concentrations of drugs to the tumors and tumor receptor-specific binding, while reducing off-target effects are needed to ensure sufficient tumor cell uptake within the primary and metastatic tumor microenvironment. The decreased non-specific adhesivity, receptor-targeted nanoparticle formulations ("DART" nanoparticles) of the invention were assessed for clinical potential in directing biological agents to the cell surface receptor Fn14, which is expressed in many solid cancer types, including TNBC primary tumors and metastatic lesions. They are contemplated for use against solid tumors, particularly brain tumors such as glioblastoma and breast cancer, including metastatic breast cancer.

16 Claims, 38 Drawing Sheets

Specification includes a Sequence Listing.

(56) References Cited

OTHER PUBLICATIONS

Nakayama, M., et al., "Fibroblast growth factor-inducible 14 mediates multiple pathways of TWEAK-induced cell death," J Immunol. 2003, pp. 341-348, vol. 170.
Nance, E.A., et al., "A dense poly(ethylene glycol) coating improves penetration of large polymeric nanoparticles within brain tissue," Sci Transl Med 2012, pp. 1-8, vol. 4, Issue 149.
Nance, E., et al., "Non-invasive delivery of stealth, brain-penetrating nanoparticles across the blood-brain barrier using MRI-guided focused ultrasound," J Control Release 2014, pp. 123-132, vol. 189.
Rich, J.N. and Bigner, D.D., "Development of novel targeted therapies in the treatment of malignant glioma," Nat Rev Drug Discov 2004, pp. 430-446, vol. 3, No. 5.
Tran, N.L., et al., "Increased fibroblast growth factor-inducible 14 expression levels promote glioma cell invasion via Rac1 and nuclear factor-kappaB and correlate with poor patient outcome," Cancer Res 2006, pp. 9535-9542, vol. 66, No. 19.
Veiseh, O., et al., "Specific targeting of brain tumors with an optical/magnetic resonance imaging nanoprobe across the blood-brain barrier," Cancer Res 2009, pp. 6200-6207, vol. 69, No. 15.
Whitsett, T.G., et al., "Elevated expression of Fn14 in non-small cell lung cancer correlates with activated EGFR and promotes tumor cell migration and invasion," Am J Pathol 2012, pp. 111-120, No. 181, vol. 1.
Willis, A.L., et al., "The fibroblast growth factor-inducible 14 receptor is highly expressed in HER2-positive breast tumors and regulates breast cancer cell invasive capacity," Mol Cancer Res 2008, pp. 725-734, vol. 6, No. 5.
Winkles, J.A., "The TWEAK-Fn14 cytokine-receptor axis: discovery, biology and therapeutic targeting," Nat Rev Drug Discov. 2008, pp. 411-425, vol. 7, No. 5.
Yin, J., et al., "AR-Regulated TWEAK-FN14 Pathway Promotes Prostate Cancer Bone Metastasis," Cancer Res 2014, pp. 4306-4317, vol. 74, No. 16.
Zhou, J., et al., "Highly penetrative, drug-loaded nanocarriers improve treatment of glioblastoma," Proc Natl Acad Sci USA 2013, pp. 11751-11756, vol. 110, No. 29.
Zhou, H., et al., "The TWEAK receptor Fn14 is a therapeutic target in melanoma: immunotoxins targeting Fn14 receptor for malignant melanoma treatment," J Invest Dermatol 2013, pp. 1052-1062, vol. 133.
Zhou, et al., "Antitumor activity of a humanized, bivalent immunotoxin targeting fn14- positive solid tumors," Cancer Res 2013, pp. 4439-4450, vol. 73, No. 14.
Zhou, H., et al., "Development and characterization of a potent immunoconjugate targeting the Fn14 receptor on solid tumor cells," Mol Cancer Ther, 2011, pp. 1276-1288, vol. 10, No. 7.
Kanapathipillai, M., et al., "Nanoparticle targeting of anti-cancer drugs that alter intracellular signaling or influence the tumor microenvironment," Advanced Drug Delivery Reviews 2014, pp. 107-118, vols. 79-80.
Schneider, C., et al., "Minimizing the Non-specific Binding of Nanoparticles to the Brain Enables Active Targeting of Fn14-positive Glioblastoma Cells," Biomaterials 2015, pp. 42-51, Vols. vol. 42.
ISA/KR: International Search Report and Written Opinion, International Patent Application No. PCT/US2015/061853, dated Aug. 10, 2016, pp. 1-14.
European Extended Search Report, EP Patent Application No. 15860689.7, dated Jun. 13, 2018, pp. 1-7.
Michaelson, J., et al., Development of an Fn14 agonistic antibody as an anti-tumor agent,"mAbs" pp. 362-375, vol. 3, Issue 4 (2011).
Bertrand et al. (2014). Cancer nanotechnology: The impact of passive and active targeting in the era of modern cancer biology. Advanced Drug Delivery Reviews, 66: 2-26.
Dancy et al. (2016). Non-specific binding and steric hindrance thresholds for penetration of particulate drug carriers within tumor tissue. Journal of Controlled Release 238:139-148.
Zhou et al. (2014). Development of human serine protease-based therapeutics targeting Fn14 and identification of Fn14 as a new target overexpressed in TNBC. Molecular Cancer Therapeutics 13:2688-2705.
Liu et al., "A strategy for precision engineering of nanoparticles of biodegradable copolymers for quantitative control of targeted drug delivery", 2010, Biomaterials, vol. 31 , pp. 9145-9155.

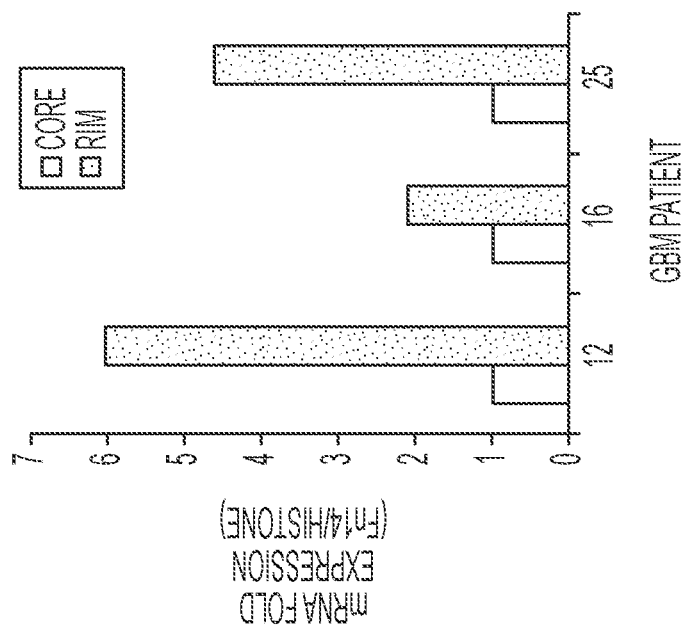
FIG. 2C
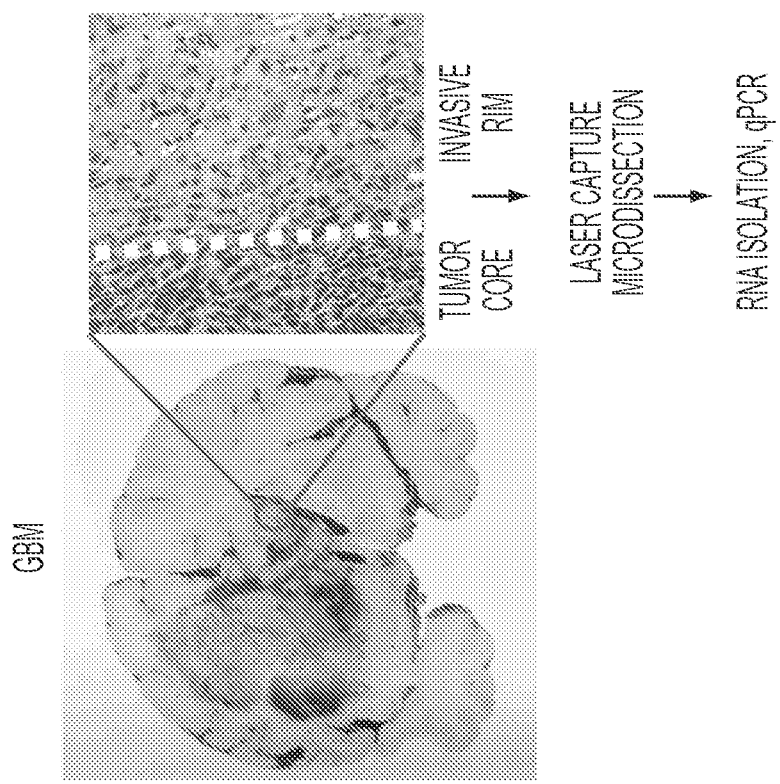
FIG. 2B
FIG. 2A

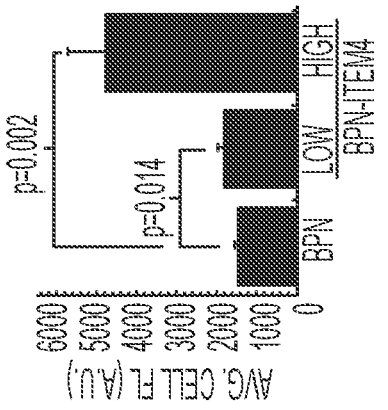
FIG. 3C
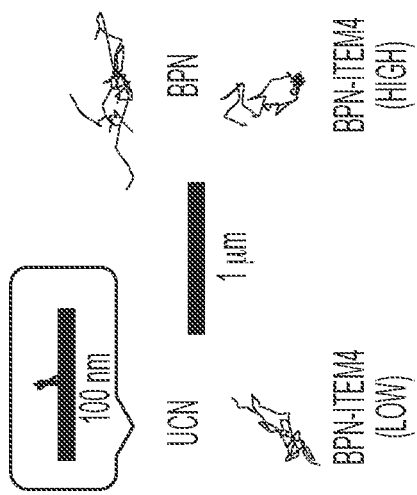
FIG. 3B
FIG. 3D
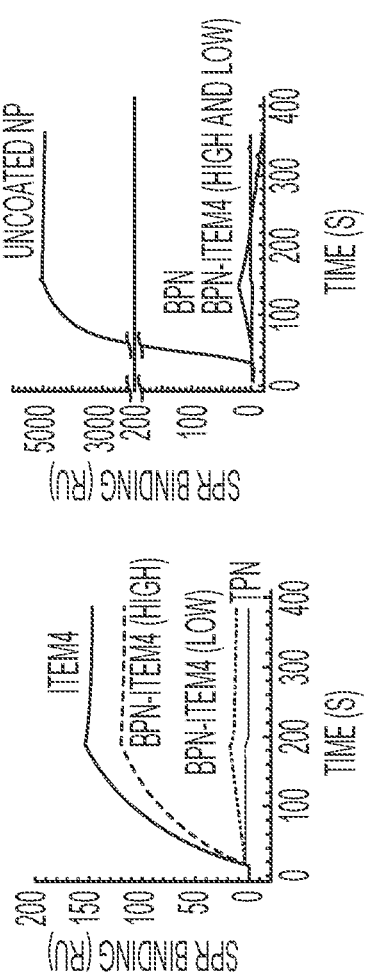
FIG. 3A

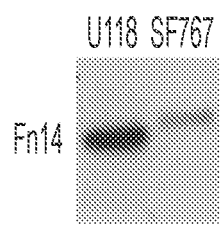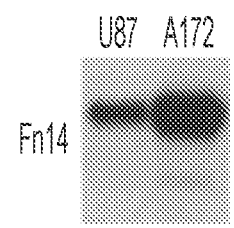
FIG. 7A  FIG. 7B

FIG. 7C  FIG. 7D

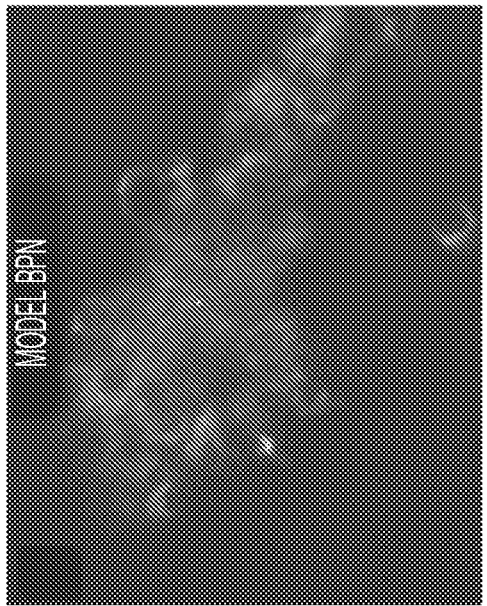
FIG. 8B MODEL BPN
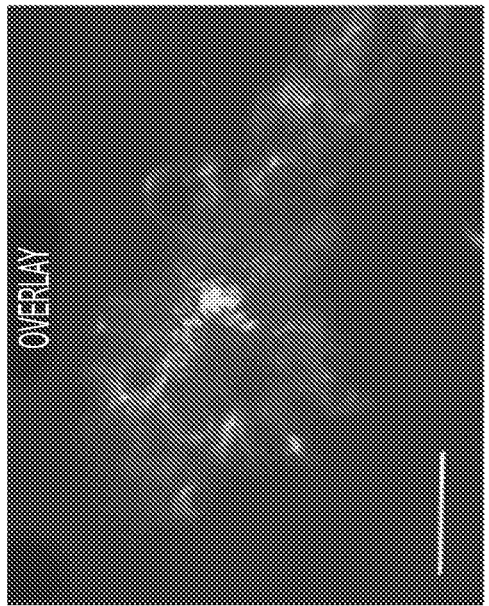
FIG. 8D OVERLAY
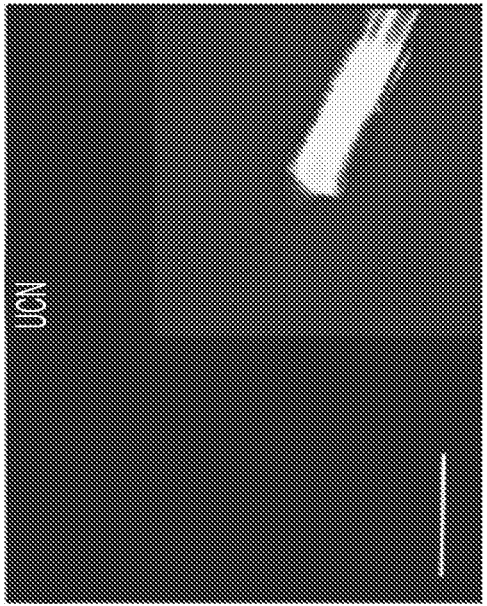
FIG. 8A UCN
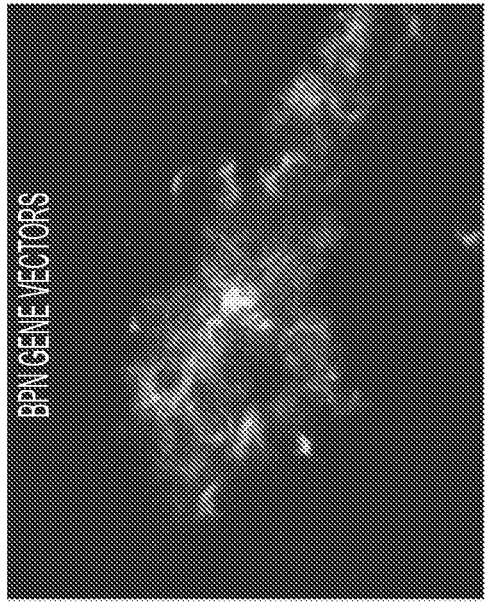
FIG. 8C BPN GENE VECTORS

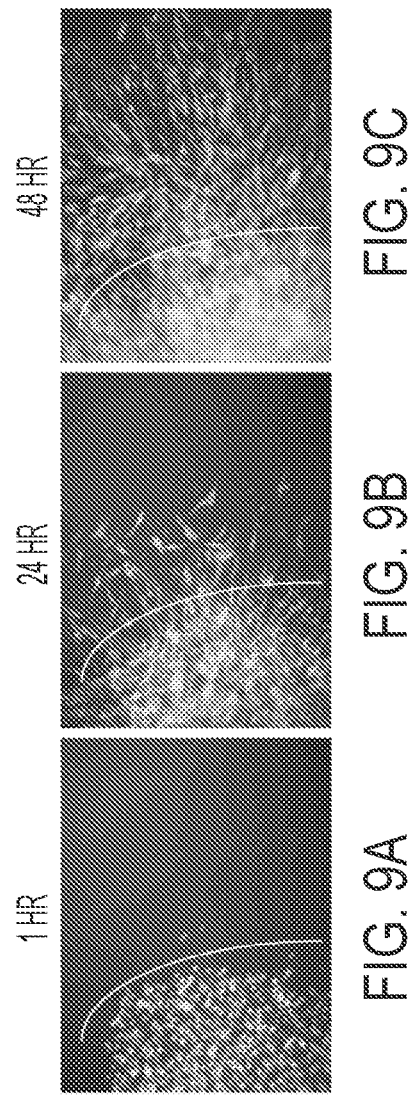

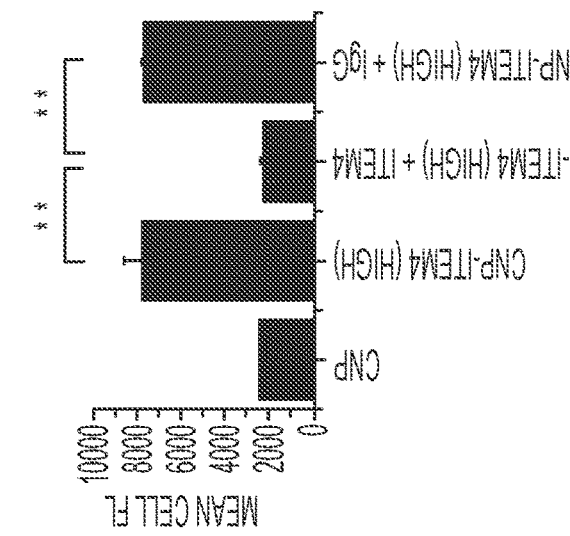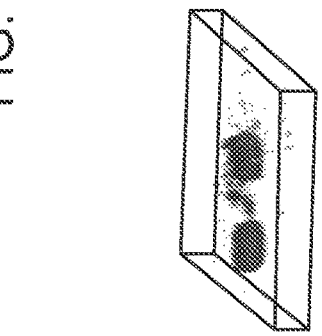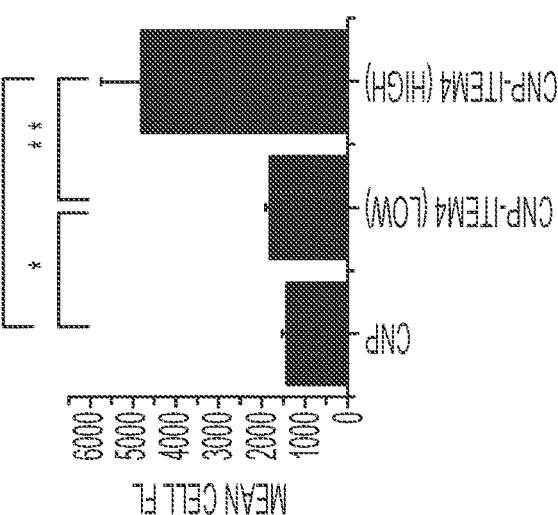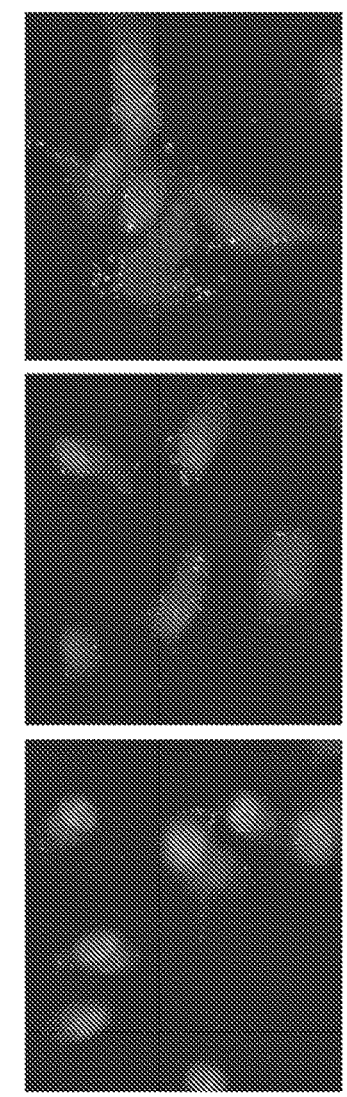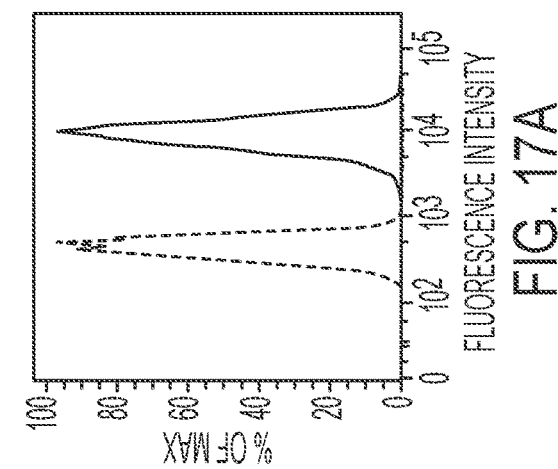

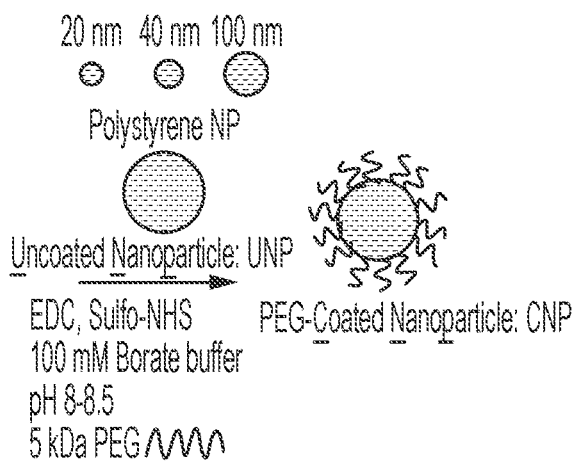
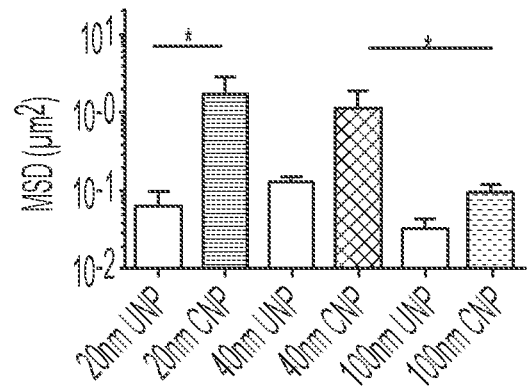
FIG. 24A  FIG. 24B
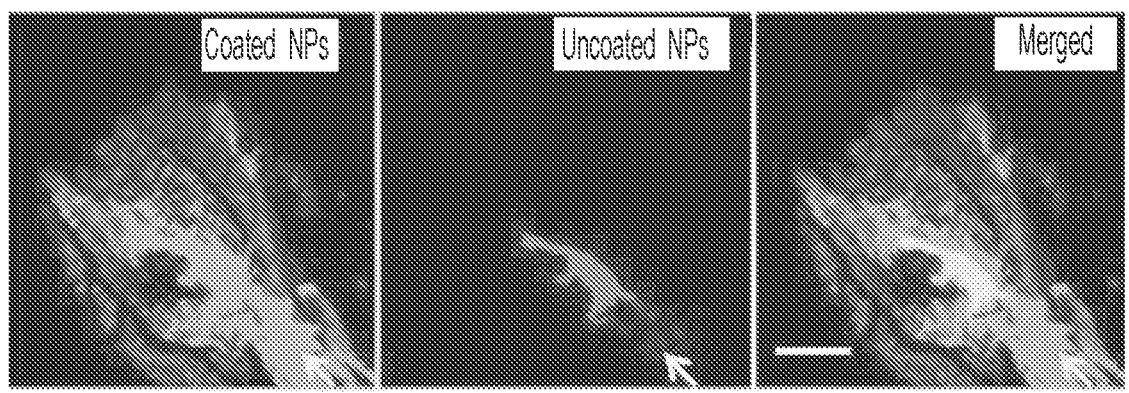
FIG. 25A  FIG. 25B  FIG. 25C

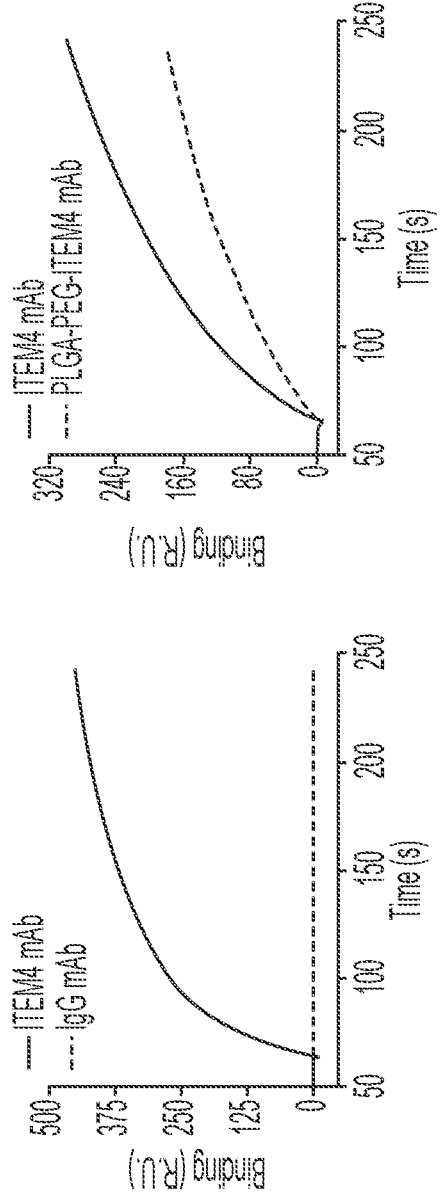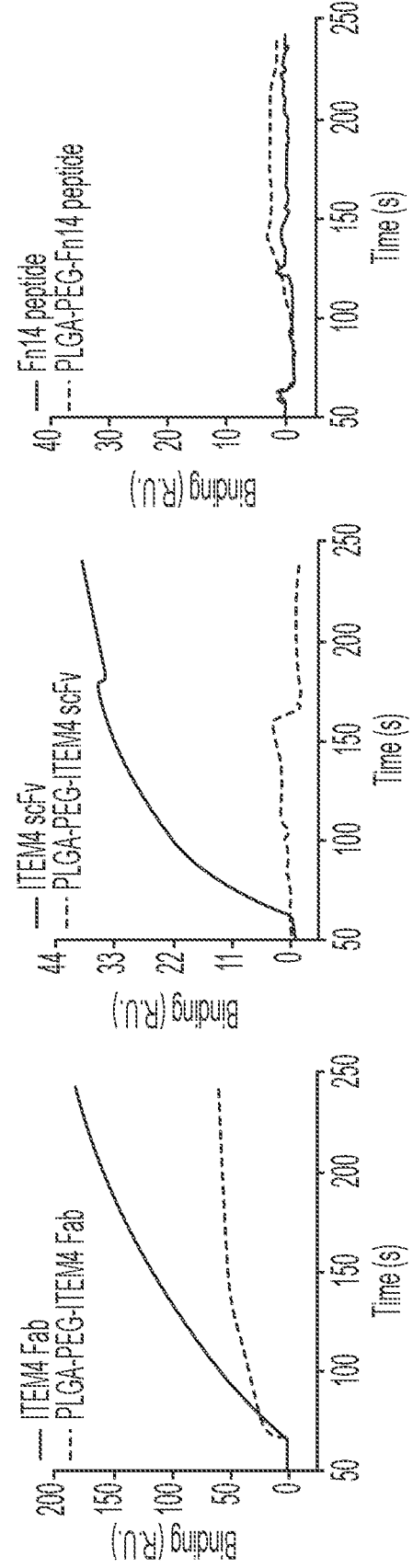
FIG. 32A
FIG. 32B
FIG. 32C
FIG. 32D
FIG. 32E

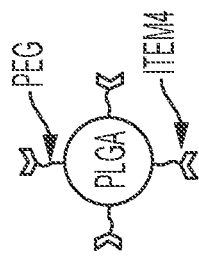
FIG. 33A
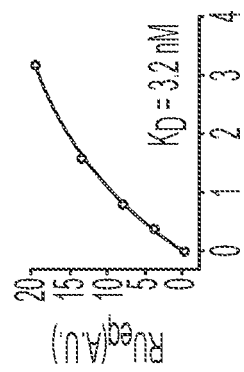
FIG. 33B
FIG. 33C
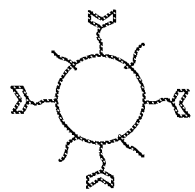
FIG. 33D
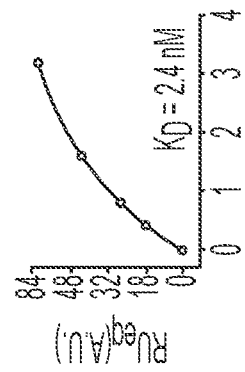
FIG. 33E
FIG. 33F
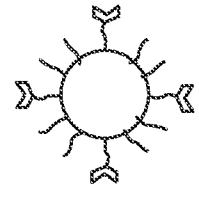
FIG. 33G
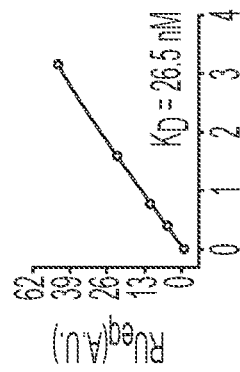
FIG. 33H
FIG. 33I

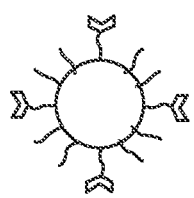
FIG. 33J
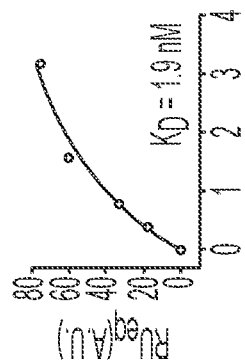
FIG. 33K
FIG. 33L
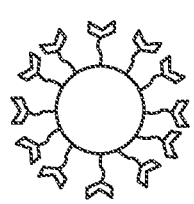
FIG. 33M
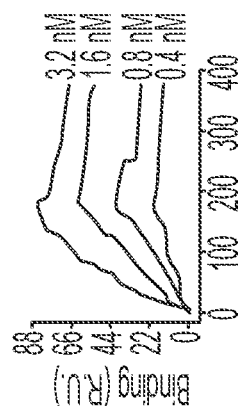
FIG. 33N
FIG. 33O

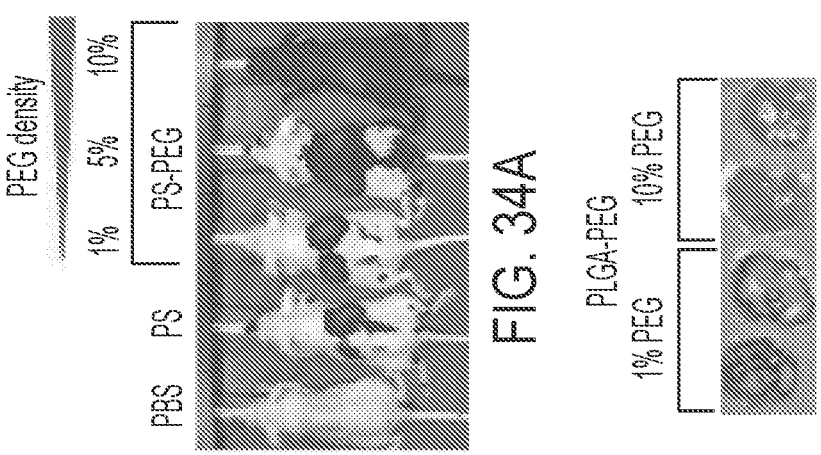
FIG. 34B
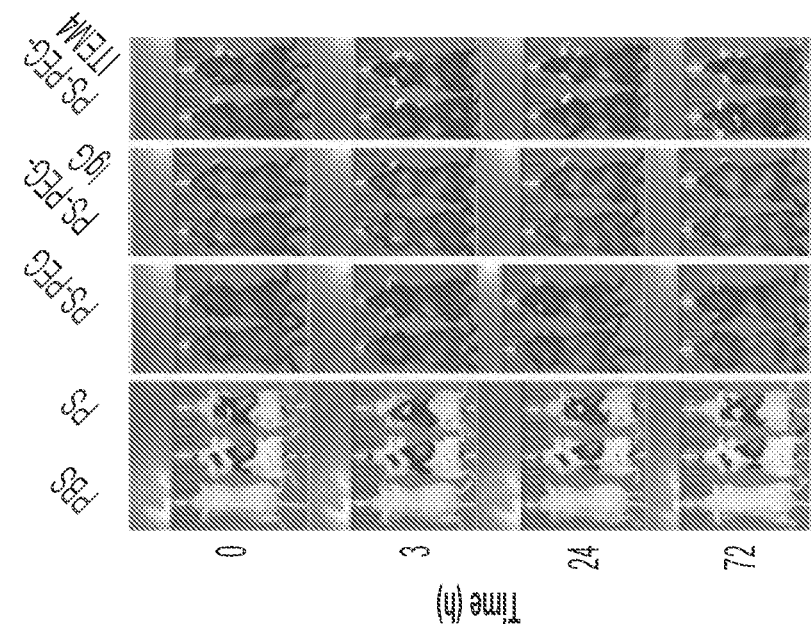
FIG. 34A
FIG. 34C

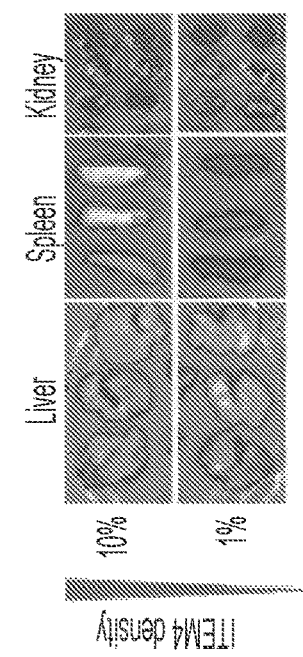
FIG. 36A
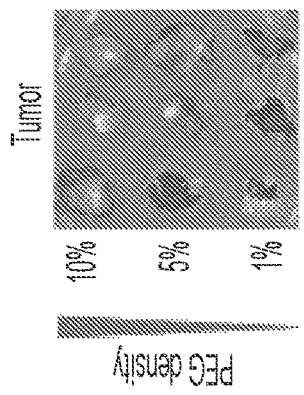
FIG. 36B
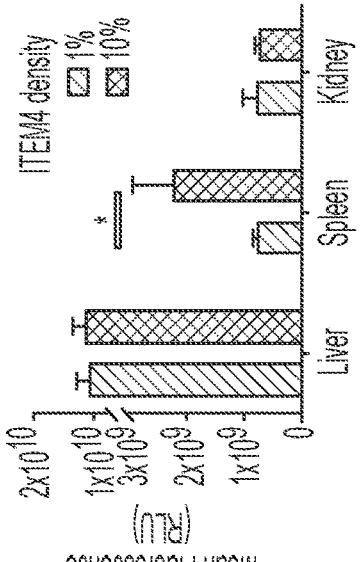
FIG. 36C
FIG. 36D
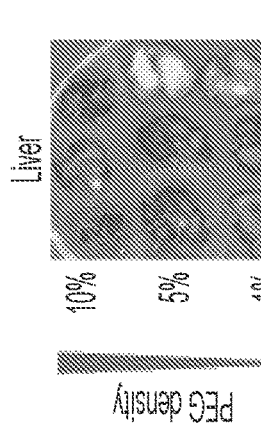
FIG. 36E
FIG. 36F
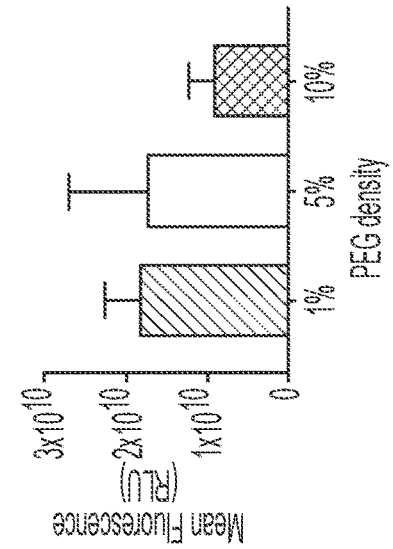
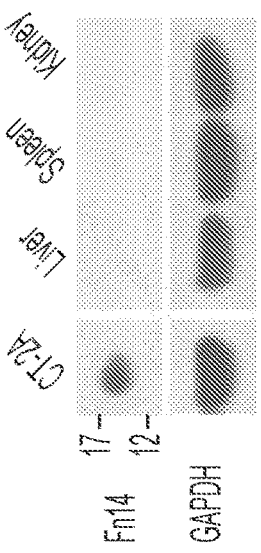
FIG. 37

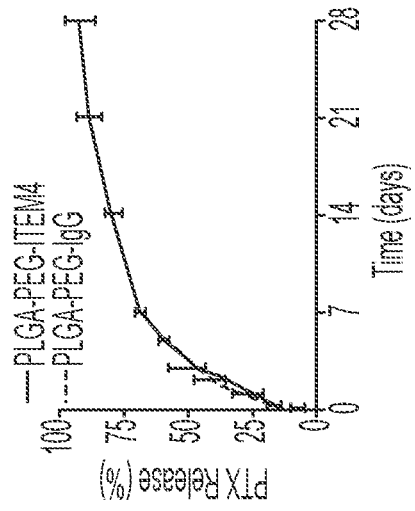
FIG. 38A
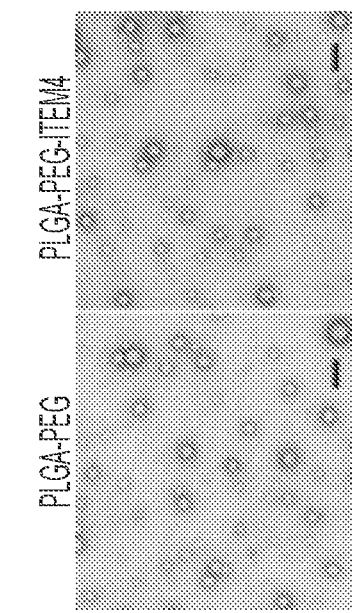
FIG. 38B
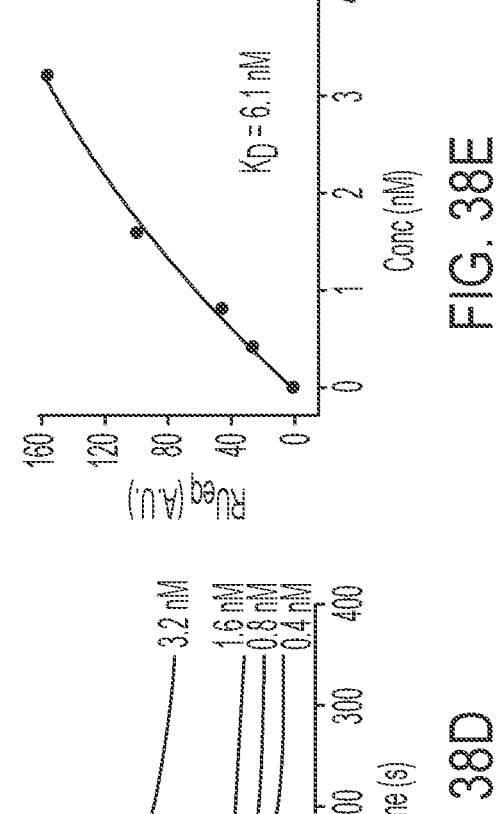
FIG. 38D
FIG. 38E
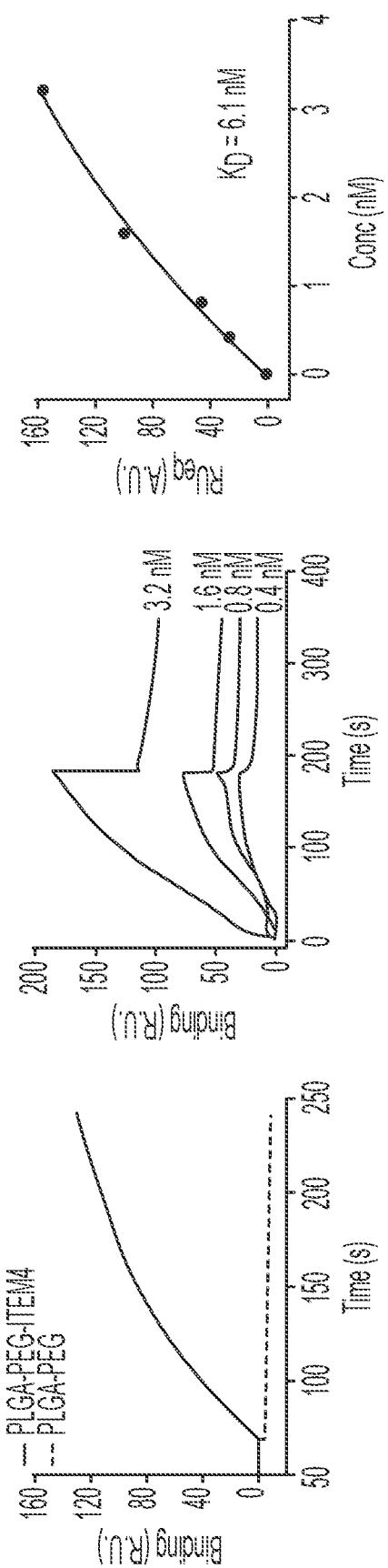
FIG. 38C

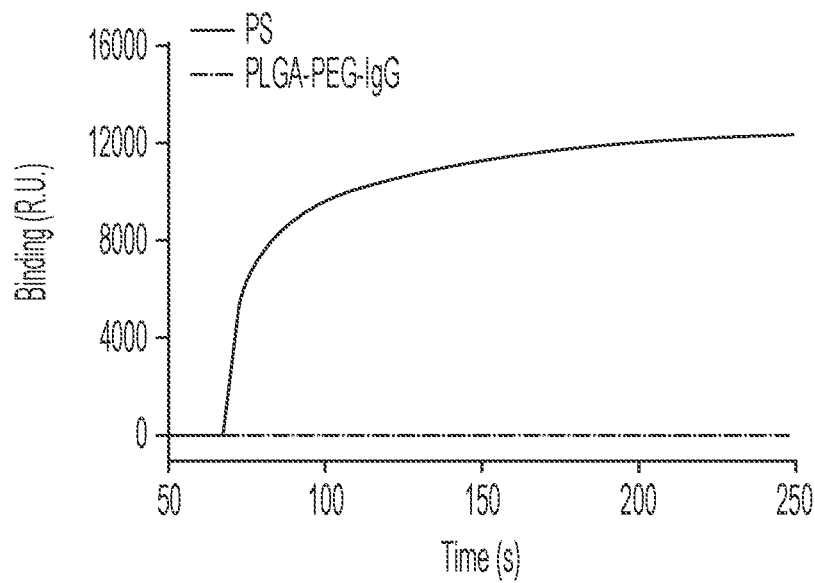
FIG. 42
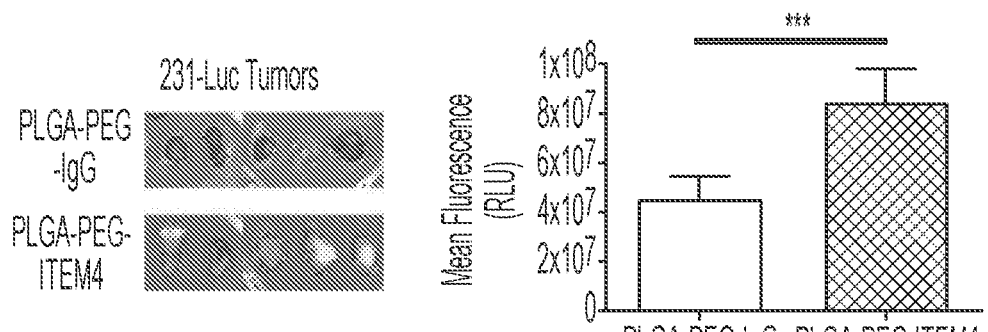
FIG. 43A
FIG. 43B
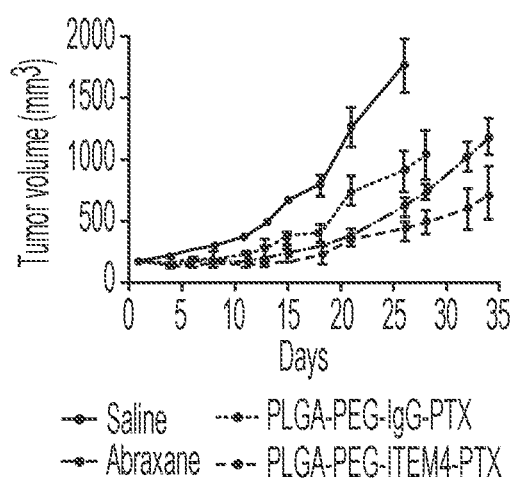
FIG. 43C
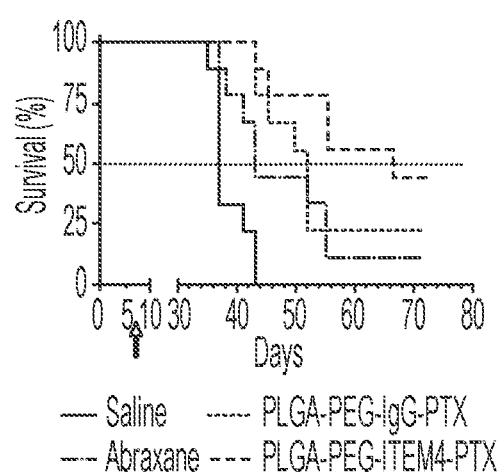
FIG. 43D

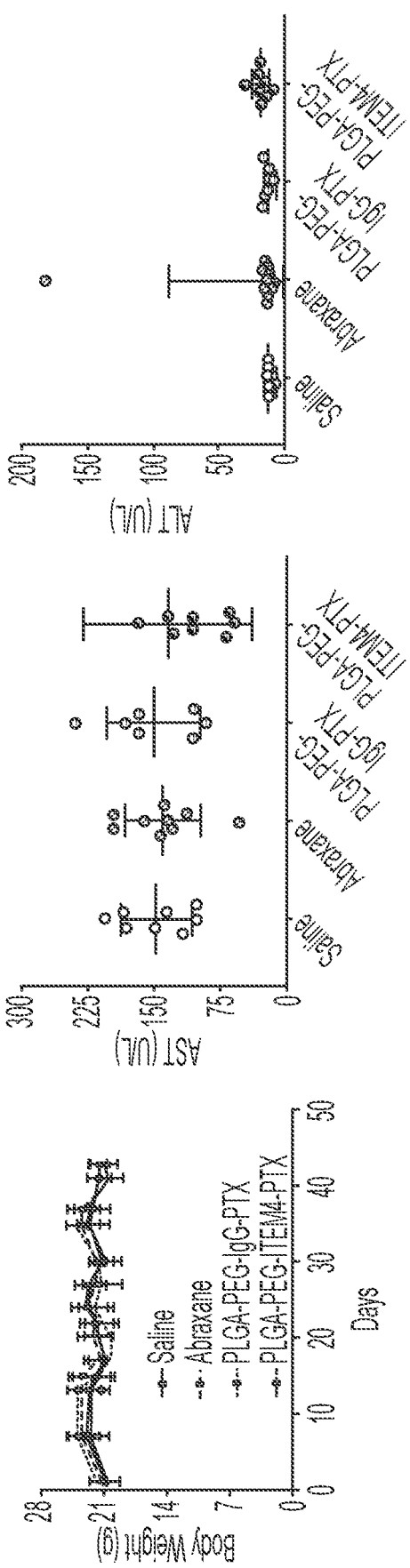
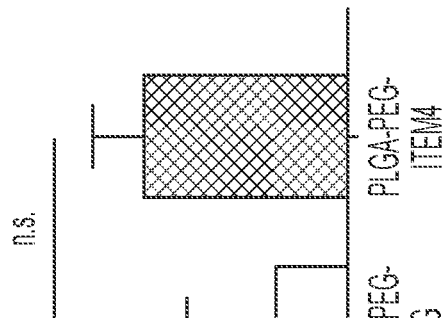
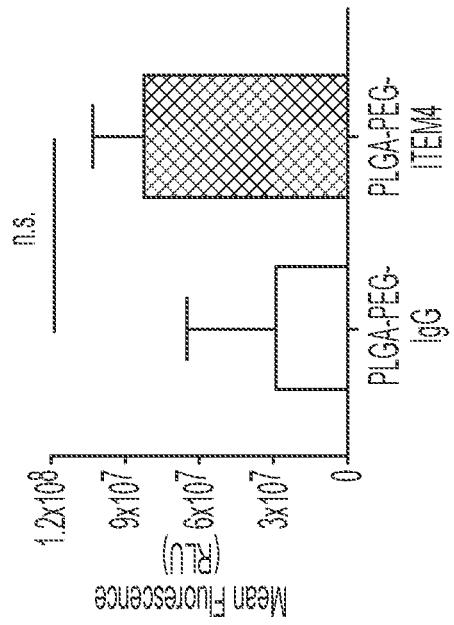
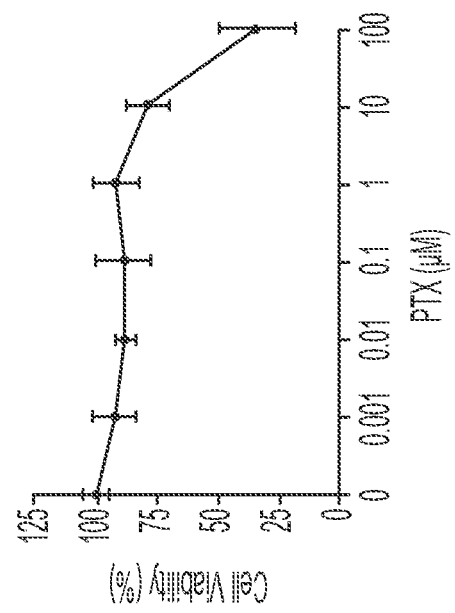

SEQUENCE LISTING

<160> NUMBER OF SEQ ID NOS: 1

<210> SEQ ID NO 1
<211> LENGTH: 128
<212> TYPE: PRT
<213> ORGANISM: Homo sapiens
<220> FEATURE:
<221> NAME/KEY: misc_feature
<223> OTHER INFORMATION: human Fn14

<400> SEQUENCE: 1

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
            20                  25                  30

Thr Ala Pro Cys Ser Arg Gly Ser Ser Trp Ser Ala Asp Leu Asp Lys
        35                  40                  45

Cys Met Asp Cys Ala Ser Cys Arg Ala Arg Pro His Ser Asp Phe Leu
    50                  55                  60

Gly Cys Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Glu Lys Phe Thr Thr Pro
            100                 105                 110

Ile Glu Glu Thr Gly Gly Glu Gly Cys Pro Ala Val Ala Leu Ile Gln
        115                 120                 125
```

DECREASED ADHESIVITY RECEPTOR-TARGETED NANOPARTICLES FOR FN14-POSITIVE TUMORS

CROSS-REFERENCE TO RELATED APPLICATIONS

This application is a continuation of U.S. patent application Ser. No. 16/289,424, filed Feb. 28, 2019 which is a continuation-in-part of U.S. patent application Ser. No. 15/528,555, filed 22 May 2017, which is a 371 national stage application of PCT Application No. PCT/US2015/061853 filed 20 Nov. 2015, which claims benefit of U.S. Provisional Application No. 62/083,011, filed 21 Nov. 2014, the entire contents of each of which are hereby incorporated by reference as if fully set forth herein, under 35 U.S.C. § 119(e).

GOVERNMENT FUNDING SUPPORT

This invention was made with government support under Grant Number CA218617 awarded by the National Institutes of Health. The government has certain rights in the invention.

REFERENCE TO SEQUENCE LISTING SUBMITTED VIA EFS-WEB

This application includes an electronically submitted sequence listing in .txt format. The .txt file contains a sequence listing entitled "15024-311US2_ST25.txt" created on Dec. 10, 2020 and is 1,674 bytes in size. The sequence listing contained in this .txt file is part of the specification and is hereby incorporated by reference herein in its entirety.

BACKGROUND

1. Field of the Invention

The invention relates to a nanoparticle delivery system suitable for delivery of treatment, imaging, and other agents to Fn14-positive tumors. These particularly include Fn14-positive, breast cancer cells. The nanoparticles of the invention are designed to overcome the specific barriers to effective treatment of primary and metastatic brain and breast cancers, tumor heterogeneity, lack of efficacious primary and metastatic tumor-specific drug targets, off-target delivery to healthy tissues, and inability to deliver sufficient quantities of the treatment or other agent into the tumor microenvironment.

2. Background of the Invention

A. Breast Cancer

Breast cancer is the most common malignancy in women in the United States of America as well as worldwide. Triple-negative breast cancer (TNBC), an aggressive subtype of breast cancer that is associated with increased metastatic potential and shorter patient survival, is characterized by the lack of expression of estrogen receptor (ER), progesterone receptor (PR), and human epidermal growth factor receptor-2 (HER2). This subtype constitutes about 20% of all breast cancer patients. Overall survival of patients diagnosed with metastatic disease is approximately 13 months. TNBC represents an important clinical challenge because these cancers respond poorly to hormone-based therapies or other available targeted agents. Therefore, chemotherapy is currently the standard treatment for TNBC patients. Patients with TNBC and HER2-positive tumors also have an increased likelihood of distant recurrences and, compared to other breast cancer subtypes, a higher risk of developing brain metastasis.

There are multiple barriers to developing effective therapeutic strategies for TNBC, including (1) tumor heterogeneity, (2) lack of primary and metastatic tumor-specific drug targets, (3) off-target delivery to healthy tissues, and (4) restricted drug delivery into the tumor microenvironment. Nanoparticles offer the possibility of engineering drug formulations that enhance the biodistribution, pharmacokinetics, and selective targeting of tumor cells in the body, which could substantially improve the therapeutic ratio of treatments for TNBC. Several FDA-approved nanotherapeutics for metastatic breast cancer are in clinical use, including Abraxane™ an albumin-bound paclitaxel (PTX) nanoparticle. Although Abraxane™ has a markedly improved safety profile compared to free PTX (administered in Cremophor™), it has not significantly improved tumor control or patient survival.

Previous studies exploring delivery improvements and limitations to solid tumors have revealed that therapeutic agents not designed to avoid body clearance and degradation mechanisms, are resistant to dispersion within tissues, and/or partition readily into non-disease sites, lead to undesirable biological effects and toxicities. While directing therapeutics to tumor specific components by receptor-mediated interactions may decrease some of these limitations, in order to fully capitalize on the potential benefits of targeting, minimizing levels of non-specific adhesivity to tissues, and off-target binding and partitioning must be considered. However, this effective balance is often quite challenging to attain and then maintain in vivo, since many targeting moieties (antibodies and related fragments, peptides, etc.) and drug delivery carriers exhibit non-specific binding to cellular, extracellular and intravascular components. In order to achieve efficient tumor-specific active targeting within tissues (such as brain and breast), the non-specific binding of nanocarriers to brain tissue components (e.g., ECM proteins) needs to be minimized to allow nanoparticles to access the target sites within the tissue and undergo the desired specific interactions. Herein, this decreased non-specific adhesivity, with respect to receptor-targeted nanoparticle formulations is sometimes referred to as "DARTs."

Therefore, there is a pressing need to identify new therapeutic targets and treatment strategies for primary and metastatic TNBC tumors.

B. Glioblastoma

Glioblastomas are tumors that arise from astrocytes, the star-shaped cells that make up the "glue-like," supportive tissue of the brain. These tumors are often highly malignant (cancerous) because the cells reproduce quickly, invade within the brain, and they are supported by a large network of blood vessels. Glioblastomas are generally found in the cerebral hemispheres of the brain, but can be found anywhere in the brain or spinal cord. Glioblastomas usually contain a heterogeneous mix of cell types. It is not unusual for these tumors to contain cystic mineral, calcium deposits, blood vessels, or mixed grades and types of tumor cells. Dead cells may also be seen, especially toward the center of the tumor. Because these tumors come from transformed brain cells, it is easy for them to invade and live within normal brain tissue. However, glioblastoma rarely spreads (metastasizes) elsewhere in the body.

There are two types of glioblastomas: primary (de novo) and secondary. Primary tumors tend to form and make their presence known quickly. This is the most common form of glioblastoma; it is very aggressive. Secondary tumors have somewhat slower growth, but still can become very aggressive. They may begin as lower-grade tumors which eventually become higher grade. They tend to be found in people 45 and younger, and represent about 10% of glioblastomas. Because glioblastomas can grow rapidly, the most common symptoms are usually caused by increased pressure in the brain. These symptoms can include headache, nausea, vomiting, and drowsiness. Depending on the location of the tumor, patients can develop a variety of other symptoms such as weakness on one side of the body, memory and/or speech difficulties, and visual changes. This type of tumor represents about 17% of all primary brain tumors and about 60-75% of all astrocytomas. They occur with increased frequency with age, and affect more men than women. Only three percent of childhood brain tumors are glioblastomas. Like many tumor types, the exact cause of glioblastoma is not known.

Glioblastoma can be difficult to treat because the tumors contain a vast array of cell types with varying sensitivity and resistance to current treatments. For a given therapy, some cells may respond well to certain therapies, while others in the tumor may not be affected at all. This is why the treatment plan for glioblastoma often combines several approaches. The first step in treating glioblastoma is a procedure to make a diagnosis, relieve pressure on the brain, and safely remove as much tumor as possible through surgery. Because glioblastomas have finger-like tentacles, they are very difficult to completely remove. This is particularly true when they are growing near the parts of the brain that control important functions such as language and coordination. Radiation and chemotherapy may be used to slow the growth of tumors that cannot be removed with surgery. Chemotherapy may also be used to delay the need for radiation in young children.

Prognosis is usually reported in years or months of "median survival." Median survival is the time at which an equal number of patients do better and an equal number of patients do worse. With standard treatment, median survival for adults with an anaplastic astrocytoma is about two to three years. For adults with more aggressive glioblastoma, treated with concurrent temozolamide and radiation therapy, median survival is about 14.6 months and two-year survival is 30%. A 2009 study reported, however, that almost 10% of patients with glioblastoma live five years or longer. Children with high-grade tumors (grades III and IV) tend to do better than adults; five-year survival for children is about 25%. In addition, glioblastoma patients who have had their MGMT gene shut off by a process called methylation also have prolonged survival rates. The MGMT gene is thought to be a significant predictor of response. However, not all glioblastomas have the same biologic abnormalities. This may be the reason different patients respond differently to the same treatment and why different patients with the same tumor have different outcomes. Researchers continue to study the common characteristics of long-term brain tumor survivors, and how personalized and targeted treatments may be optimally used to treat brain tumor patients.

C. Targeting Cancers

A broad range of cancers overexpress fibroblast growth factor-inducible 14 ("Fn14"). Fn14 receptor overexpression has been detected in solid tumors (e.g., bladder, prostate, brain (e.g., glioblastoma), breast, cervical, colorectal, esophageal, liver, lung (e.g., non-small cell lung cancer), skin (e.g., melanoma), ovarian, pancreatic, prostate, renal, testicular) and in tumor metastases (e.g., bone, liver, brain lymph node). For example, northern blot analysis was used to compare Fn14 mRNA levels in HCC tumor tissue versus adjacent non-tumoral liver tissue; elevated levels of Fn14 gene expression were found in three of the four tumor specimens examined. Investigators also detected Fn14 mRNA induction in two transgenic mouse models of hepatocarcinogenesis. Fn14 gene expression was examined in normal breast tissue and primary breast tumor samples using two experimental approaches: in situ hybridization and immunohistochemistry. Fn14 mRNA expression was detected in 0/10 normal tissue specimens and 35/60 breast tumor specimens using the first approach and, in a different set of samples, Fn14 protein expression was detected in 1/10 normal tissue specimens and 10/19 breast tumor specimens using the second approach.

Glioblastoma is the most common form of primary brain cancer and takes more than 15,000 lives in the USA each year, often with devastating neurological consequences. GBM is not curable with surgery alone because tumor cells invade the surrounding brain, rendering complete resection unsafe. Current adjuvant therapies use fractionated external beam radiation combined with the orally delivered chemotherapeutic agent Temodar®. Despite these treatments, median survival is still less than 18 months. A major limitation is believed to be delivery of therapeutics to invasive cancer cells, often found many centimeters away from the main tumor mass within functioning brain tissue. Novel treatment approaches such as Gliadel®, a biodegradable chemo-loaded polymer wafer that is implanted in the brain after tumor resection, only provides a modest improvement in median survival time due in part to limited drug penetration into the surrounding brain tissue.

The location of invasive tumor cells presents several barriers to therapeutic delivery. The blood-brain barrier (BBB) regulates the trafficking of molecules to and from the brain. Unresectable tumor cells are consistently found in brain regions with relatively healthy blood vessels. Therapeutics can potentially be delivered to the brain by receptor-mediated transport across the BBB, mechanical disruption of the BBB via focused ultrasound, or using hyperosmotic agents, however it is not yet clear whether sufficient therapeutic doses can be safely achieved. Local delivery approaches, such as Gliadel®, wafer or convection-enhanced delivery (CED), avoid the complexities associated with the BBB, delivering therapies more directly and deeper into brain tissue. The safety and feasibility of these approaches in human clinical studies has been repeatedly shown, yet penetration of substances is often still limited. This is largely due to the anisotropic and electrostatically charged extracellular space (ECS) found between brain cells, comprising 15-20% of total brain volume, which acts as a 'brain penetration barrier' (BPB). The surrounding extracellular matrix (ECM) and brain cells act as sinks for small molecule drugs, proteins, viral particles, and standard nanoparticles, thereby limiting their diffusion and distribution throughout the brain and effective therapeutic results. In addition, perivascular channels serve as critical and efficient brain clearance mechanisms for small molecules and particulate delivery systems, further limiting the distribution, residence time, and efficacy of therapeutic agents.

Targeted therapeutics offer the potential for delivering therapies directly to invasive brain cancer cells to improve the desired treatment effects while minimizing unwanted toxicity. Previous studies exploring this approach for invasive brain cancer have included targeting tumor cell surface molecules and tumor-associated ECM components. However, most targeted therapeutic formulations have yet to show improvements in disease progression or survival.

There is a need in the art for new and improved methods of treatment, especially for cancers such as metastatic breast cancer and glioblastoma which can deliver therapeutics directly to tumor cells outside an area that is safe or available for surgical removal.

SUMMARY OF THE INVENTION

The present invention provides a targeted nanoparticle therapeutic carrier that allows one to deliver one or more therapeutic agent(s) to a tumor component, for example breast cancer cells, including metastatic cancer cells. These nanoparticles have (1) an optimized stealth surface coating (e.g., dense low molecular weight PEG), (2) a targeting moiety conjugated on the surface of the particle that binds to specific tumor component(s) (e.g., Fn14 via a monoclonal antibody (e.g., ITEM4), and (3) a biologically active agent such as one or more therapeutic agent (e.g., an anticancer agent), diagnostic agent (e.g., contrast agents; radionuclides; and fluorescent, luminescent, and magnetic moieties), prophylactic agent (e.g. a vaccine), nutraceutical agent (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging). This particle delivery system can target disease-specific structures with minimized non-specific binding within the microenvironment and/or circulation and highly specific binding to the disease-specific structures.

Preferred embodiments of the invention include tumor tissue-penetrating, paclitaxel (PTX)-loaded (or any other suitable anti-tumor treatment agent) nanoparticle formulation that specifically targets tumor (preferably breast cancer cells and/or metastatic breast cancer cells) via Fn14. This advanced drug formulation preferably significantly improves the efficacy of the anti-tumor treatment agent against breast cancer (including TNBC) while minimizing toxicity.

Therefore, the invention provides a drug delivery nanoparticle for treatment of breast cancer and metastatic breast cancer, comprising:

a) a nanoparticle having a hydrodynamic diameter of about 4 nm to about 200 nm;

b) a coating of polyethylene glycol with a surface density of at least 3 polyethylene glycol molecules per 100 nm$^2$;

c) an Fn14 targeting moiety that specifically binds to the cell surface of a breast cancer cell or metastatic breast cancer cell; and d) a therapeutic agent.

Other embodiments include a drug delivery nanoparticle as described above, wherein the hydrodynamic diameter of the nanoparticle is about 20 nm to about 200 nm, or about 100 nm.

Further embodiments also include a drug delivery nanoparticle as described above, wherein the Fn14 targeting moiety is an anti-Fn14 antibody or a binding fragment thereof, preferably a monoclonal anti-Fn14 antibody, for example ITEM4, ITEM4-SH, ITEM4 scFv, and ITEM4 Fab.

In some embodiments, the drug delivery nanoparticle has a surface density of PEG about 5 polyethylene glycol molecules per nm$^2$ to about 20 polyethylene glycol molecules per nm$^2$. In some embodiments, the drug delivery nanoparticle has a surface density of the Fn14 targeting moiety about 0.05% to about 15%, or about 0.1% to about 10%, or about 1% to about 10%, or about 2% to about 8%, for example, 0.1%, 0.2%, 0.5%, 1%, 1.5%, 2%, 5%, 8%, 10%, or 12%. Preferably, the density of the Fn14 targeting moiety, such as ITEM 4, is about 0.0006 ITEM 4 molecules per 100 nm$^2$ (0.1%) to about 0.075 ITEM 4 molecules per 100 nm$^2$ (10%).

The invention also provides a pharmaceutical composition comprising a pharmaceutically acceptable vehicle and a drug delivery nanoparticle as described herein.

The invention also provides a method of treating breast cancer, comprising administering to a subject in need a therapeutically effective amount of a drug delivery nanoparticle as described herein or a therapeutically effective amount of the pharmaceutical compositions described herein. Preferably, in some embodiments, the breast cancer is metastatic breast cancer.

BRIEF DESCRIPTION OF THE DRAWINGS

The following drawings form part of the present specification and are included to further demonstrate certain embodiments of the present invention. The invention may be better understood by reference to one or more of these drawings in combination with the detailed description of specific embodiments presented herein.

FIG. 2A is a photograph illustrating the approach used to generate the data in FIG. 2C.

FIG. 2B is an insert magnifying the indicated portion of FIG. 2A. FIG. 2C is a bar graph showing that Fn14 mRNA expression is higher in actively invading glioma cells compared to stationary core cells.

FIG. 3A, FIG. 3B, and FIG. 3C are graphs illustrating (FIG. 3A) surface plasmon resonance (SPR) analysis measuring the binding of the Fn14 monoclonal antibody ITEM4, uncoated polystyrene NPs and polystyrene BPNs with varying surface densities of FFEM4 to the Fn14 receptor, (FIG. 3B) SPR analysis measuring the binding of uncoated polystyrene NPs and polystyrene BPNs with varying surface densities of ITEM4 to mouse brain ECM, and (FIG. 3C) human U87 glioma cells treated with fluorescent non-targeted BPNs or BPNs with varying surface densities of ITEM4 and analyzed by flow cytometry. FIG. 3D shows individual particle trajectories in fresh rodent brain tissue, determined using a multiple particle tracking (MPT) assay and high resolution microscopy.

FIG. 4A shows that immunohistochemical staining for Fn14 occurs in the PDX tumors, GBM44 (Fn14+) but not GBM5 (Fn14-).

FIG. 5A provides expression levels of Fn14 mRNA in 184 normal and brain tumor specimens and FIG. 5B provides expression values of Fn14 mRNA, analyzed in two patient survival clusters.

FIG. 6A shows that nanovectors efficiently enter mouse glioma cells (GL261). FIG. 6B shows that, after entering cells, nanovectors effectively deliver a plasmid gene construct with green fluorescent reporter and inhibitor RNA for luciferase (shLuc) to GL261 cells that constitutively express luciferase.

FIG. 7A through FIG. 7D are western blot images illustrating Fn14 expression in several GBM cell lines.

FIG. 8A, FIG. 8B, FIG. 8C, and FIG. 8D are photographs illustrating BPN gene vectors, showing similar in vivo brain distribution as optimized model BPN. FIG. 8A shows that conventional uncoated nanoparticles injected directly into the living mouse brain have minimal diffusion or transport. FIG. 8B shows that the preferred model BPN rapidly distribute within the mouse brain. FIG. 8C shows that BPN gene vectors also penetrate well in brain tissue. FIG. 8D is an overlay of model BPN and BPN gene vectors, showing a close overlap of the two particle types.

FIG. 9A, FIG. 9B, and FIG. 9C are photographs illustrating the brain slice invasion assay, featuring green fluorescence protein ("GFP")-labeled human glioma cells after 1 hour (FIG. 9A), 24 hours (FIG. 9B), and 48 hours (FIG. 9C) incubation.

FIG. 11A presents data on free ITEM 4 and thiol-modified ITEM4 (ITEM4-SH) and FIG. 11B presents data on CNP and CNP-ITEM4 nanoparticles with two different surface densities of ITEM4.

FIG. 17A, FIG. 17B, FIG. 17C, FIG. 17D, FIG. 17E, FIG. 17F, FIG. 17G and FIG. 17H are graphs and photographs illustrating FACS analysis of Fn14 expression in U87 GBM cells (FIG. 17A), and analysis of CNP, CNP-ITEM4 (low), and CNP-ITEM4 (high) uptake in Fn14-positive U87 GBM cells (FIG. 17B, FIG. 17C, FIG. 17D, FIG. 17E, FIG. 17F, FIG. 17G, AND FIG. 17H).

FIG. 24A is a diagram of 20, 40, and 100 nm fluorescent PS NPs that were either left uncoated (UNP) or were coated with PEG (CNP) for MPT studies. FIG. 24B shows the ensemble-averaged mean square displacement (MSD) of 20, 40, and 100 nm UNPs and CNPs at a time scale of 1 second in tumor slices.

FIG. 25A, FIG. 25B, and FIG. 25C are fluorescent microscopic images showing the distribution of PEG-coated and uncoated nanoparticles 10 minutes after co-injection into the breast tumor of a living mouse. FIG. 25C is a merged image.

FIG. 28 is a set of images showing Fn14-targeted nanoparticles associate with Fn14-positive breast tumors.

FIG. 32A, FIG. 32B, FIG. 32C, FIG. 32D, and FIG. 32E are graphs showing that ITEM4 mAb, but not control IgG, bind to Fn14-oated Biacore™ chips (FIG. 32A); and comparing Fn14-specific binding of ITEM4 (FIG. 32B), ITEM4 fab (FIG. 32C), ITEM4 scFv (FIG. 32D) and Fn14 peptide (FIG. 32E) and their corresponding formulations.

FIG. 33A, FIG. 33D, FIG. 33G, FIG. 33J, and FIG. 33M depict various nanoparticle formulations that were tested. FIG. 33B, FIG. 33E, FIG. 33H, FIG. 33K, and FIG. 33N provide binding kinetics data for these nanoparticle formulations, and FIG. 33C, FIG. 33F, FIG. 33I, FIG. 33L and FIG. 33O provide equilibrium binding data for these nanoparticle formulations.

FIG. 34A, FIG. 34B, and FIG. 34C show the distribution of the indicated nanoparticles following tail injection into normal mice.

FIG. 36A presents a fluorescence image of livers from 231-Luc tumor-bearing mice isolated 1 hour after administration of rhodamine-labeled PLGA-PEG-ITEM4 nanoparticles with 1%, 5%, or 10% PEG density; FIG. 36B shows analysis of fluorescence intensity from FIG. 36A.

FIG. 37C is a fluorescence image of 231-Luc tumors after administration of rhodamine-labeled PLGA-PEG-ITEM4 nanoparticles with 1%, 5%, or 10% PEG density. FIG. 36D presents analysis of fluorescence intensity from FIG. 36C. FIG. 36E is an image of livers, spleens, and kidneys isolated from non-tumor bearing mice 1 hour after administration of rhodamine-labeled PLGA-PEG10%-ITEM4 with 1% or 10% ITEM4 density. FIG. 36F presents analysis of fluorescence intensity from FIG. 36E.

FIG. 37 presents western blot analysis of Fn14 and GAPDH levels in mouse CT-2A glioma cells (positive control), liver, spleen, and kidney samples.

FIG. 38A shows well-dispersed round shaped nanoparticles viewed by transmission electron microscopy (scale bars=100 nm). FIG. 38B is a graph presenting PTX release kinetics from PLGA-PEG-IgG and PLGA-PEG-ITEM4 nanoparticles in PBS at 37° C. FIG. 38C shows specific binding of nanoparticles to Fn14-Coated™ chips using an SPR assay. FIG. 38D provides kinetic binding analysis showing binding curves of PLGA-PEG-ITEM4 at various concentrations after incubation with mouse blood serum. FIG. 38E provides a binding isotherm of PLGA-PEG-ITEM4, showing $RU_{eq}$ values determined from their respective kinetic binding analysis. The data were fit to a single class of binding sites by non-linear regression analysis using GraphPad™ software.

FIG. 42 is a graph showing that the binding of non-targeted PLGA-PEG-IgG nanoparticles do not bind to Matrigel™-coated Biacore™ chip compared to PS nanoparticles used as positive control.

FIG. 43A shows fluorescence images of 231-Luc tumors after tail vein injection of fluorescent nanoparticles; FIG. 43B provides the analysis of fluorescence data from FIG. 43A.

FIG. 43C and FIG. 43D are graphs showing 231-Luc tumor growth curves and cumulative survival of mice after one intravenous administration of the indicated agents.

FIG. 44A shows the body weight of individual mice in each treatment group of FIG. 43C and FIG. 43D, measured every 2-3 days. FIG. 44B and FIG. 44C present data on the serum levels of the AST (FIG. 44B) and ALT liver enzymes (FIG. 44C).

FIG. 45A presents data on the viability of 231-Br-Luc cells determined by MTS assay after 24 hours' of incubation with various PTX concentrations. FIG. 45B shows the fluorescence intensity of rhodamine-labeled nanoparticle accumulation in intracranial 231-Br-Luc tumors isolated from mice 24 hours after nanoparticle administration. The data were analyzed for significance using Student's t-test (n.s.=not significant).

DETAILED DESCRIPTION

1. Definitions

Figure 1A:
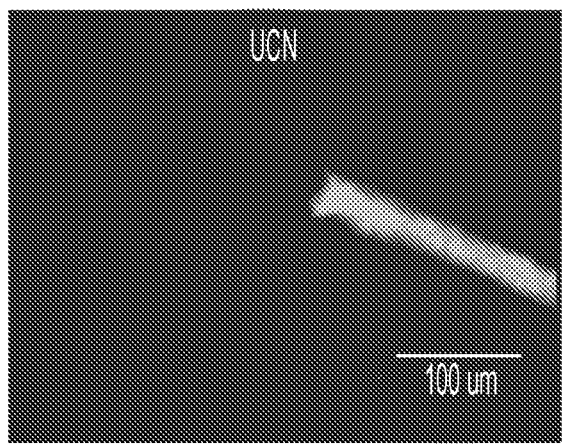
FIG. 1A and FIG. 1B are photographs showing in vivo imaging of uncoated nanoparticles (UCN) and brain penetrating nanoparticle (BPN) movement in the mouse brain.

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated.

The term "about," as used herein, means plus or minus 20 percent of the recited value, so that, for example, "about 0.125" means 0.125±0.025, and "about 1.0" means 1.0±0.2.

The term "administering" as used herein, refers to any convenient method of providing the inventive compounds and compositions of the invention. These methods can include any known method, however preferably administering is performed by injection, for example direct injection into or around the tumor site, intravenous, intraarterial, intracranial, or intraperitoneal injection, intrathecal injection, intramuscular or subcutaneous injection, and the like, including any means known in the art, for example for delivery of a biologically active agent.

As used herein, the term "amphiphilic" refers to a property where a molecule has both a polar portion and a non-polar portion. Often, an amphiphilic compound has a polar head attached to a long hydrophobic tail.

As used herein, the term "biologically active agent" includes, for example, therapeutic agents (anticancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging) or any agent that has or will have a biological effect on cells. These agents can be delivered by the disclosed nanoparticles. Exemplary agents to be delivered in accordance with the present invention include, but are not limited to, drugs, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, vaccines, immunological agents, etc., and/or combinations thereof. In some embodiments, the agent or agents to be delivered are useful in the treatment of cancer (e.g., breast cancer or brain cancer, including metastatic breast cancer and glioblastoma).

As used herein, the term "bind" or "binding" refers to the interaction between a corresponding pair of molecules or portions thereof that exhibit mutual affinity or binding capacity, typically due to specific or non-specific binding or interaction, including, but not limited to, biochemical, physical, physiological, and/or chemical interactions. "Biological binding" defines a type of interaction that occurs between pairs of biological molecules such as proteins, nucleic acids, glycoproteins, carbohydrates, hormones, and the like. The term "binding partner" refers to a molecule that can undergo binding with a particular molecule. "Specific binding" refers to molecules, such as polynucleotides or antibodies, that are able to specifically bind to or recognize a binding partner (or a limited number of binding partners) to a substantially higher degree than to other, similar biological entities.

As used herein, the term "biodegradable" means that the materials degrades or breaks down into its component subunits, or digestion, e.g., by a biochemical process, of the material into smaller (e.g., non-polymeric) subunits.

As used herein, the term "cancer" includes pre-malignant as well as malignant cancers. Cancers include, but are not limited to, brain or central nervous system cancer, prostate, gastric cancer, colorectal cancer, skin cancer, e.g., melanomas or basal cell carcinomas, lung cancer, breast cancer, cancers of the head and neck, bronchus cancer, pancreatic cancer, urinary bladder cancer, peripheral nervous system cancer, esophageal cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like, including metastatic cancers. "Cancer cells" can be in the form of a tumor, exist alone within a subject, or be cell lines derived from a cancer. Cancer can be associated with a variety of physical symptoms.

As used herein, the term "Fn14" (fibroblast growth factor-inducible 14), also known as "CD266" or "TWEAK R (TNFRSF12A)" is a receptor for TNF-like weak inducer or apoptosis (TWEAK)/TNFSF12, also known as CD255. Fn14 is expressed on endothelial cells, as well as on many cancer tissues, and plays a role in TWEAK-induced endothelial cell migration, proliferation, and angiogenesis as well as cancer cell growth, migration and invasion. The TWEAK-Fn14 interaction, or antibody-mediated triggering of Fn14 is also able to induce apoptosis and necrosis in certain cells, which might have therapeutic potential.

As used herein, the term "coating density" refers to either (1) number of polymer chains or antibodies per total surface area of a nanoparticle ($\#/nm^2$) or (2) total mass of polymer chains or antibodies per total mass of a nanoparticle (% w/w). These are two different but related ways to describe the term "coating density" of polymer chains (e.g. PEG), antibodies, and Fn14-targeting targeting ligands on the surface of nanoparticles.

As used herein, the term "controlled release" (and variants of that term) particularly, in the context of a "controlled-release system," generally encompasses release of a substance (e.g., a drug) at a selected site, controllable in rate, interval, and/or amount. Controlled release encompasses, but is not necessarily limited to, delayed delivery, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)). As used herein, the term "sustained release" refers to release of a substance over an extended period of time in contrast to a bolus type administration in which the entire amount of the substance is made biologically available at one time.

The term "diameter" is art-recognized and is used herein to refer to either of the physical diameter or the hydrodynamic diameter of the nanoparticle. The diameter of an essentially spherical nanoparticle may refer to the physical or hydrodynamic diameter. The diameter of a nonspherical nanoparticle may refer preferentially to the hydrodynamic diameter. As used herein, the diameter of a non-spherical nanoparticle can refer to the largest linear distance between two points on the surface of the nanoparticle. When referring to multiple nanoparticles, the diameter of the nanoparticles typically refers to the average diameter of the nanoparticles. Nanoparticle diameter can be measured using a variety of techniques in the art including, but not limited to, dynamic light scattering. In certain embodiments, the nanoparticle has a diameter of about 100 nm, 110 nm, 120 nm, 130 nm, 140 nm, 150 nm, 160 nm, 170 nm, 180 nm, or 190 nm. Or, the nanoparticle has a diameter between 50 nm and 100 nm. In other embodiments, the nanoparticle has a diameter between 110 nm and 115 nm. Preferred nanoparticles have a diameter of about 20 nm to about 200 nm, and most preferably about 50 nm to about 120 nm. In certain embodiments, the nanoparticle has a diameter of about 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, or 190 nm. Or, the nanoparticle has a diameter between 50 nm and 100 nm. In other embodiments, the nanoparticle has a diameter between 110 nm and 115 nm. Preferred nanoparticles have a diameter of about 20 nm to about 200 nm, and most preferably about 50 nm to about 120 nm.

The term "extracellular matrix" ("ECM") as used herein, is a collection of extracellular molecules that provides structural and biochemical support to the surrounding cells in any tissue. The composition of ECM varies between multicellular structures; however, cell adhesion, cell-to-cell communication and differentiation are common functions of the ECM. The animal extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest.

The extracellular matrix of the adult brain tissue has a unique composition. The striking feature of this matrix is the prominence of lecticans, proteoglycans that contain a lectin domain and a hyaluronic acid-binding domain. Hyaluronic acid and tenascin family adhesive/anti-adhesive proteins are also abundant. Matrix proteins common in other tissues are nearly absent in adult brain. The brain extracellular matrix appears to have trophic effects on neuronal cells and affect neurite outgrowth. The unique composition of this matrix may be responsible for the resistance of brain tissue toward invasion by tumors of neuronal and non-neuronal origin. The role of ECM in neurological development, function and degeneration has evolved from a simplistic physical adhesion to a system of intricate cellular signaling. While most cells require ECM adhesion to survive, it is now clear that differentiated function is intimately dependent upon cellular interaction with the ECM. Therefore, it is not surprising that the ECM is increasingly found to be involved in the enigmatic process of neurode generation and plays a central role in numerous neurological diseases.

The ECM in breast tissue is increasingly recognized as an important regulator in breast cancer progression and metastasis. Breast tumor ECM proteins include fibrillar collagens, fibronectin, specific laminins, proteoglycans, matricellular proteins, as well as remodeling enzymes, which change the matrix structure and biomechanical properties.

The term, "Fn14," as used herein, means fibroblast growth factor-inducible 14, a member of the tumor necrosis factor (TNF) receptor family that is induced in a variety of cell types in situations of tissue injury. Fn14 becomes activated by TNF-like weak inducer of apoptosis (TWEAK), a typical member of the TNF ligand family. Fn14 is an FGF-inducible receptor. It is often expressed at low levels on cells of normal tissues, and can be upregulated in injury or disease, or on cancer (e.g., tumor) cells. Without wishing to be bound by theory, it is believed that stimulation of Fn14 by an Fn14 ligand (e.g., TWEAK) can in some cases induce tumor cell death, and that an anti-Fn14 antibody will also be effective in killing tumor cells. It is also believed that Fn14 is overexpressed in human tumors. An anti-Fn14 antibody can trigger tumor cell death and therefore be therapeutically beneficial in treating cancer. The sequence of human Fn14 is:

(SEQ ID NO: 1)
MARGSLRRLLRLLVLGLWLALLRSVAGEQAPGTAPCSRGSSWSADLDKCM

DCASCRARPHSDFLGCCAAAPPAPFRLLWPILGGALSLTFVLGLLSGFLV

WRRCRREKFTTPIEETGGEGCPAVALIQ.

Additional Fn14 protein sequences include: mouse Fn14 (e.g., NCBI accession no. AAF07882 or NP 0.038777 or Q9CR75 or AAH25860), human Fn14 (e.g., NCBI accession no. NP . . . 057723 or BAA94792 or Q9NP84 or AAH02718 or AAF69108); rat Fn14 (e.g., NCBI accession no, NP_851600 or AAH60537); and Xenopus Fn14 (e.g., NCBI accession no, AAR21225 or NP_001083640). These Fn14 proteins can be used, e.g., as an immunogen to prepare anti-Fn14 antibodies. Anti-Fn14 antibodies can then be screened to identify agonist antibodies, as described herein.

As used herein, the term "gene construct" can mean a construct which is capable of expressing one or more gene(s) or sequence(s) of interest in a host cell. In certain embodiments, the "gene construct" is delivered by a nanoparticle such as a polymeric nanogene vector. These highly compacted pH-responsive nanoparticles can mediate transgene silencing in gliomas and can be targeted to Fn14-positive glioblastoma cells.

As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient.

As used herein, the term "intracranial" means within the cranium or at or near the dorsal end of the spinal cord and includes the medulla, brain stem, pons, cerebellum, and cerebrum.

As used herein, the terms "incorporated" and "encapsulated" refers to incorporating, formulating, or otherwise including an active agent into and/or onto a composition that allows for release, such as sustained release, of such agent in the desired application. The terms contemplate any manner by which a biologically active agent or other material is incorporated into a polymer matrix, including for example: attached to a monomer of such polymer (by covalent, ionic, or other binding interaction), physical admixture, enveloping the agent in a coating layer of polymer, and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to-the incorporation of a biologically active agent or other material and at least one other biologically active agent or other material in a subject composition.

As used herein, "ITEM4" is an antibody that recognizes human Fn14, otherwise known as CD266/TWEAK Receptor, a 14 kDa type I transmembrane protein and member of the tumor necrosis factor receptor superfamily (TNFRSF12A) expressed by a few normal tissues and at much elevated levels by most human tumor types. The ITEM4 antibody reacts with human TWEAK Receptor/

Fn14. Fn14 contains one cysteine-rich domain in the extracellular region and a TNFR-associated factor binding domain, but does not contain a death domain (DD) cytoplasmic region. Fn14 plays a role in TWEAK-induced endothelial cell migration, proliferation, and angiogenesis. TWEAK-Induced cell death via Fn14 includes both apoptosis and necrosis and can be blocked by an anti-TWEAK antibody, CARL-1. Fn14 is expressed on HUVEC and in some cancer tissues but not on freshly isolated PB-Cs. Fn14 mRNA expression has been identified during liver regeneration, it has been reported that ITEM4 cross-reacts with mouse Fn14.

As used herein, the term 'local administration" means direct administration of a pharmaceutical at or to the vicinity of a site on or within an animal body, at which site a biological effect of the pharmaceutical is desired. Local administration generally excludes systemic routes of administration, such as intravenous or oral administration.

As used herein, the term "liposome" refers to an artificially-prepared spherical vesicle composed of a lamellar phase lipid bilayer. The liposome can be used as a vehicle for administration of nutrients and pharmaceutical drugs. Liposomes can be prepared by disrupting biological membranes (such as by sonication). Liposomes are often composed of phosphatidylcholine-enriched phospholipids and may also contain mixed lipid chains with surfactant properties such as egg phosphatidylethanolamine. A liposome design may employ surface ligands for attaching to unhealthy tissue. The major types of liposomes are the multilamellar vesicle (MLV), the small unilamellar liposome vesicle (SUV), the large unilamellar vesicle (LUV), and the cochleate vesicle. In certain embodiments, anti-cancer drugs such as paclitaxel may be conjugated to a liposome or inserted into a liposome and delivered to tumor cells.

As used herein, the term "nanoparticle" refers to particles with at least one dimension less than 100 nm or between 1 and 200 nanometers in size. In nanotechnology, a particle is defined as a small object that behaves as a whole unit with respect to its transport and properties. Particles are further classified according to diameter. Ultrafine particles are the same as nanoparticles and between 1 and 100 nanometers in size. Coarse particles cover a range between 2,500 and 10,000 nanometers. Fine particles are sized between 200 and 2,500 nanometers.

As used herein, the term "non-immunogenic" refers to a compound (such as an endogenous growth factor) in its native state which normally elicits no, or only minimal levels of, circulating antibodies, T-cells, or reactive immune cells, and which normally does not elicit in the individual an immune response against itself.

As used herein, the term "neurodegenerative disease" or "neurological disorder" refers to a disease in which neurons of the CNS die or lose function or have physical degeneration including loss (death) of axons. Neurodegenerative diseases include Parkinson's Disease, Alzheimer's disease, Huntington's disease and brain and spinal cord injuries that are associated with axon death.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer, i.e., a copolymer or a block copolymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer."

The term "small molecule" refers to compounds, whether naturally-occurring or artificially created (e.g., via chemical synthesis) that have relatively low molecular weight and that are not proteins, polypeptides, or nucleic acids. Small molecules typically have multiple carbon-carbon bonds (i.e. are organic compounds).

As used herein, the terms "subject," "host," and "patient," are used interchangeably and mean an animal being treated with the present compositions, including, but not limited to, simians, humans, avians, felines, canines, equines, rodents, bovines, porcines, ovines, caprines, mammalian farm animals, mammalian sport animals, and mammalian pets. A "subject in need thereof" is a subject that suffers from a tumor, for example of the breast or brain, or a metastatic condition such as metastatic breast cancer, or is a subject that is suspected of suffering from such a condition or tumor.

As used herein, the term "targeting moiety" means any binding partner that can bind to the cell of interest, preferably an antibody. The term "antibody" includes antibody fragments, characteristic portions of antibodies, as are known in the art. Single chain targeting moieties can be identified, e.g., using procedures such as phage display. Targeting moieties disclosed herein are typically conjugated to a disclosed polymer or copolymer (e.g. PLA-PEG), and such a polymer conjugate may form part of a disclosed nanoparticle.

As used herein, "therapeutically effective amount" means an amount sufficient to treat a subject afflicted with a disease (e.g., a neurodegenerative disease or neurological disorder or brain cancer) or to alleviate a symptom or a complication associated with the disease in one dose or in a course of treatment comprising two or more doses administered over time.

As used herein, "therapeutic agent" means a compound that has a beneficial and desirable or therapeutic effect when consumed, administered, or applied. In certain embodiments, therapeutic agents are chemotherapy medications used to attack cancers, e.g., glioblastomas or breast cancer. In other embodiments, therapeutic agents are anti-AD agents, anti-PD agents, anti-HD agents, anti-epilepsy agents). Some therapeutic agents are biological in origin, and can include components of plants and minerals as well as animal products. Others are synthetic, produced in a lab environment.

As used herein, the terms "treating" and "treatment" refer to slowing, stopping or reversing the progression of a disease, particularly a neurodegenerative disease or cancer. These terms "treatment," "treating," and the like, refer to obtaining a desired pharmacologic and/or physiologic effect. The effect can be prophylactic in terms of completely or partially preventing a condition, progression of a pre-disease state or symptom thereof and/or can be therapeutic in terms of a partial or complete cure for a condition or disease and/or adverse effect attributable to the condition or disease. "Treatment" therefore includes any treatment of a condition or disease in a mammal, particularly in a human, such as by administration of a compound or composition. This includes: (a) preventing the condition or disease or symptom thereof from occurring in a subject which may be predisposed to the condition or disease but has not yet been diagnosed as having it, (b) inhibiting the condition or disease or symptom thereof, such as, arresting its development, and (c) relieving, alleviating or ameliorating the condition or disease or symptom thereof, such as, for example, causing regression of the condition or disease or symptom thereof.

2. Overview

It has been discovered that tumor cells (i.e., breast cancer and glioblastoma cells) and diseased cells of the brain due to neurodegenerative diseases or neurological disorders (i.e., Alzheimer's Disease ("AD"), Parkinson's Disease ("PD") or Huntington's Disease ("HD")) and elsewhere in the body can be specifically targeted by using a particulate delivery system that is loaded with biologically active agents. Other conditions suitable for targeted effects include but are not limited to lung cancer, prostate cancer, breast cancer, medulloblastoma, radiation injury, and inflammatory diseases.

This particulate delivery system is able to bind to a target on the tumor cell or disease specific region. Specifically, binding can occur using a biologically active agent such as an Fn14 monoclonal antibody that is specific for the Fn14 protein on the cell surface of an Fn14 positive cancer cell (i.e., breast cancer cell or metastatic breast cancer cell) in patients with cancer. These Fn14 monoclonal antibody-decorated particles are designed and engineered to penetrate tissue and selectively bind to Fn14 but not to normal cells or to the tumor microenvironment such as ECM proteins. Minimizing non-specific binding and size-related steric restrictions of targeted particles in the tissue to be treated can greatly improve the access of particulate delivery systems to remote tumor cells such as widely distributed metastatic cells released from a tumor.

Certain embodiments of the invention involve a targeted nanoparticle having a hydrodynamic diameter between 4 nm and 200 nm. The nanoparticle is coated with a polyethylene glycol (PEG) polymer to achieve a surface density of at least 3 PEG molecules per 100 nm$^2$ (preferably between 3-25 PEG molecules per 100 nm$^2$, more preferably 5-20 PEG molecules per 100 nm$^2$ or more, and most preferably 10-15 PEG molecules per 100 nm$^2$, including, for example, 3, 4, 5, 6, 7, 8, 9, 10, 12, 15, 20, and 25 PEG molecules per 100 nm$^2$) and configured to penetrate tissue and the extracellular matrix around the area to be treated (e.g., a tumor, such as breast cancer cells), thereby enabling improved distribution of the therapeutic agent within the tumor. Targeting moieties such as the Fn14 monoclonal antibody, ITEM4, or modified versions such ITEM4-SH, are conjugated on a surface of the nanoparticle and configured to promote specific binding to a cell surface molecule such as Fn14 protein expressed by the target cell (i.e., a tumor cell such as a breast cancer cell).

The nanoparticle may further comprise a biologically active agent such as therapeutic agents (anticancer agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), nucleic acids (e.g. DNA and RNA), and imaging agents (e.g., via magnetic resonance imaging, optical imaging, positron emission tomography, X-ray computed tomography, and ultrasound imaging) in or on the nanoparticle. The biologically active agent is selected to enhance a desired response in the target cell intracellularly or extracellularly or region, for example to treat, kill, or image the tumor. In some embodiments of the invention, methods are provided for treating or diagnosing breast cancer or breast cancer metastasis, or a disease or disorder of the brain (e.g., a tumor such as glioblastoma, neurological disorder, neurodegenerative disease, brain injury, or trauma), or lung, administering to a patient in need thereof a therapeutically effective amount of the optimized particulate therapeutic formulation either locally or systemically.

Certain embodiments of the invention also include pharmaceutical compositions and kits encompassing them. The pharmaceutical composition can comprise a nanoparticle as described herein and a pharmaceutically acceptable excipient or excipients for delivery. The pharmaceutical compositions can further comprise imaging agents via magnetic resonance imaging, optical imaging, positron emission tomography, X-ray computed tomography, and ultrasound imaging. The compositions can be delivered to the tissue or cells to be treated via direct approaches (i.e. stereotactic injection or other direct injection into the tumor and/or the area around the tumor, convection enhanced delivery), systemic approaches (i.e. intravenous, intra-arterial), intra-thecal, and others.

The disclosure of the invention in this specification includes all possible combinations of such particular features. For example, where a particular feature is disclosed in the context of a particular embodiment or embodiment of the invention, or a particular claim, that feature can also be used, to the extent possible, in combination with and/or in the context of other particular embodiments and embodiments of the invention, and in the invention generally. For the purposes of explanation, numerous specific details are set forth in order to provide a thorough understanding of the present invention. It will be apparent, however, to one skilled in the art that the present invention may be practiced without these specific details. These and other features, aspects, and advantages of the present invention will become better understood with regard to the following description, appended claims, and accompanying figures.

3. Brief Summary of Results

The surface properties of therapeutic nanoparticles were engineered to decrease non-specific adhesivity and optimize tumor receptor-targeting (DART formulation) in order to improve blood circulation time, tumor accumulation, tissue penetration, and therapeutic efficacy. Paclitaxel-loaded Fn14-targeted DARTs outperformed Abraxane™, an FDA-approved paclitaxel nano-drug formulation, in both orthotopic and brain metastasis models of TNBC growth. These results offer new insights into methods to develop therapeutic nanoparticles for effective treatment of primary cancers and metastatic lesions.

This application contains work designed to determine the NP size and surface PEG density characteristics of nanoparticle delivery systems that are required for tumor tissue penetration adequate to treat the tumor and for low enough adhesivity to the extracellular tumor components for sufficient specific binding to the tumor to occur. This work is designed to explain in vivo differences between clinically-relevant particulate delivery systems including albumin-based nanoformulations, PEGylated liposomes, and biodegradable polymeric nanoparticles. This work also highlights the utility of SPR as a high throughput method to screen NPs for tumor penetration. Finally, drug-loaded targeted and non-targeted biodegradable particles were successfully generated and were assessed for their specific and non-specific binding abilities using SPR.

PLGA-containing nanoparticles with a low molecular weight PEG coating were used to encapsulate PTX. Surface modifications have been made to enable nanoparticle targeting to Fn14-positive TNBC tumors and to prevent non-specific binding to tumor ECM. TNBC tumor growth inhibition of these PTX-loaded nanoparticles was assessed. In summary, the invention involves a nanoparticle platform that can diffuse and penetrate within tumor tissue and selectively target tumors. This optimizes therapeutics to improve drug efficacy while limiting side effects of free drug and non-targeted therapies.

4. EMBODIMENTS OF THE INVENTION

A. General Discussion

In certain embodiments of the invention, relatively free movement of nanoparticles within tissue with minimal non-specific binding and consideration of size-related steric restrictions has been accomplished by using a targeted nanoparticle delivery system. Specifically, the enhanced ability to diffuse through tissue allows the development of a selective targeting strategy to produce nanoparticulate drug carriers to breast and brain tumors.

When administered intracranially, in certain embodiments, 100 nm PEG-coated, Fn14-targeted nanoparticles (CNP-ITEM4) showed broad distribution in the brain and selective targeting to the Fn14-positive tumor cells in mice bearing human U87 tumor xenografts. Tumor cells located at distant sites, deep within the brain, likely contribute to tumor recurrence since they cannot be removed with surgery and are the most difficult to treat due to the close proximity of functioning brain cells and the intact BBB. Therefore, reducing the non-specific binding towards the brain ECM is a critical rate-limiting step in the development of effective targeted treatments. Tumor specific targeting of nanoparticles can be enhanced through a balance of (i) minimal non-specific binding to provide broad particle dispersion and (ii) selective binding to distant glioma cells via Fn14, a cell surface molecule expressed by these cells.

Fn14, the smallest member of the TNFR superfamily, is an emerging molecular target for GBM therapy. Fn14 is minimally expressed in normal human brain, but highly expressed in malignant gliomas with more aggressive and invasive characteristics, and in breast cancer. Importantly, elevated Fn14 mRNA and protein expression has been detected in the rim of invading glioma cells with less elevation in the tumor core, which provides the opportunity to target the invasive cells with Fn14-directed therapeutics. The Fn14-specific monoclonal antibody ITEM4 was used as the targeting moiety in initial studies here. This targeting molecule was chosen based on previous studies revealing that Fn14-positive cancer cells are vulnerable to ITEM4-based immunotoxins. Although monoclonal antibodies introduce some inherent limitations (specifically, their relatively large size due to the presence of non-binding regions and the Fc region may contribute to off-target effects, for example cell binding, recognition, and clearance) the highly specific binding of a full monoclonal antibody enabled an important proof-of-concept determination in this study.

Current therapies and clinical trials using non-targeted and targeted therapeutic strategies for GBM have been affected by limited distribution within the brain. For example, carmustine was shown to diffuse a few millimeters from the implantable Gliadel polymer wafer surface during the majority of the release phase in vivo. In addition, recent clinical trials have shown that CED of targeted toxins, such as IL-13-, IL-4-, and transferrin-conjugated toxins, as well as viral particles, failed to show survival improvements. This is most likely because penetration and distribution of the therapeutic agent is still limited. In other examples, investigators have shown that even following CED, the ECM acts as a diffusion barrier limiting the spatial distribution of therapeutic nanoparticles. Therefore, the diffusion and distribution of therapeutics within the brain and in other tissues remains a major limitation to achieving significant treatment efficacy, even with these local therapeutic approaches. This is thought to be especially important for GBM given the invasive, migratory nature of the disease.

Recent studies suggest targeted nanoparticle therapies offer the potential of delivering agents directly to invading tumor cells to improve treatment efficacy while minimizing associated toxicities. In one example, chlorotoxin conjugated chitosan-based nanoparticles showed preferential accumulation in gliomas in mice. In other study, liposomes conjugated with IL-13 were able to deliver doxorubicin specifically to glioma cells. However, achieving broad particle distribution and therapeutically relevant nanoparticle targeting remain a challenge. Nanoparticle diffusion in the brain predominantly takes place through narrow tortuous spaces between cells. The ECM, the main component of the extracellular space, imposes an adhesive and steric barrier to the diffusion of nanoparticles through the brain parenchyma, as shown with the uncoated 100 nm nanoparticles (UNP) in this study. The ECS volume fraction and tortuosity have been found to increase with glioma histopathological grade, further increasing the diffusion barriers for small molecules and nanoparticles. Hence, limited penetration of targeted therapeutic nanoparticles in the ECS remains a key hurdle to (i) effective drug distribution within tumor-affected regions, and (ii) targeting to tumor-related structures where moving through tissue and only attaching to specific structures may improve efficacy and reduce toxicity.

It is possible to minimize the non-specific binding to the ECM in the design of a targeted tissue penetrating nanoparticle system, which then can allow for selective tumor cell targeting with minimal off-target binding. The demonstration here of enhanced particle distribution and tumor targeting suggests a promising opportunity for the development of new formulation strategies for brain, breast, and other cancers. Based on the formulation characteristics developed here in model polystyrene nanoparticles, drug delivery platforms that can be readily translated into new therapeutic systems, such as biodegradable PLGA nanoparticles, can be envisioned. A similar strategy can be adapted to a variety of different FDA-approved polymers, drugs, gene constructs, and targeting ligands. These results support further investigation into the use of the Fn14-targeted nanoparticle platform with CED and other novel delivery approaches for GBM to potentially improve the distribution and duration of therapeutic and other effects. Fn14 also is overexpressed in a broad range of other cancers outside the brain and breast, including melanoma, prostate, and non-small cell lung cancer. Accordingly, an Fn14-targeted nanoparticle platform may have broader applicability beyond GBM and breast cancer patient therapy in the future.

A particularly promising tumor cell surface target for drug delivery in TNBC is fibroblast growth factor-inducible 14 (Fn14). Fn14, a member of the tumor necrosis factor receptor (TNFR) superfamily, is expressed at low levels in healthy tissues but highly expressed in approximately 20 solid cancer types. High Fn14 expression levels in tumors positively correlates with poor patient outcome. Previous studies have shown that Fn14 expression is low in normal breast tissue, but frequently elevated in the HER2-positive and TNBC intrinsic subtypes of breast cancer. Importantly, Fn14 is also highly expressed in bone, lymph node, and brain metastases of breast cancer patients. These findings indicate that Fn14 has the potential to serve as a potentially powerful cell surface portal for delivery of therapeutic DARTs for TNBC and other solid tumors.

Therapeutic nanoparticles (NPs) approved for clinical use in breast cancer patients provide only modest improvements in patient survival, in part due to tumor tissue penetration barriers, such as a dense and complex extracellular matrix (ECM) and elevated interstitial fluid pressure, which hinder the penetration of drugs and NPs into and within the tumor interstitium. While there is some published information about potential NP size limits for effective tumor penetration, the influence of surface properties on the optimal size and dispersion of NPs in tumors remains unclear. Most chemotherapeutics have a non-specific mechanism of action and show poor biodistribution, which results in dose-limiting toxicities. Nanomedicine has the potential to improve treatment efficacy and reduce side-effects and toxicities through sustained and targeted drug delivery.

Here, the thresholds for NP size and surface poly(ethylene glycol) (PEG) density in these nanoparticles, for tumor tissue penetration, have been explored. NPs as large as 63 nm, but less than 116 nm in diameter, diffused rapidly within a tumor extracellular matrix (ECM) preparation and tumor xenograft tissues. In addition there is a positive correlation between PEG density and NP diffusion. Non-specific binding of NPs to tumor ECM was assessed by surface plasmon resonance (SPR), which showed excellent correlation with the particle diffusion results. Paclitaxel has been conjugated to the polymer backbone of PLGA containing a low molecular weight PEG coating. Additional surface modifications have been made to enable NP targeting to Fn14-positive triple-negative breast tumors and to prevent non-specific binding to tumor ECM. In summary, an NP platform that can diffuse and penetrate within tumor tissue and selectively target tumors has been developed. Using this approach, therapeutic versions can be optimized to improve drug efficacy while limiting many of the side effects and risks of free drug and either non-targeted or inadequately targeted therapies.

B. Polymers

In some embodiments, the nanoparticles of the invention comprise a matrix of polymers and a biologically active agent. In some embodiments, a biologically active agent and/or targeting moiety can be associated with at least part of the polymeric matrix. For example, in some embodiments, a targeting moiety (e.g. an antibody or ligand) can be covalently associated with the surface of a polymeric matrix. In some embodiments, covalent association is mediated by a linker. The biologically active agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g. targeting moiety) and the second macromolecule comprising a second polymer that is not bound to a targeting moiety. The nanoparticle can optionally include one or more additional, unfunctionalized, polymers.

Any biocompatible polymer can be used in accordance with the present invention.

Polymers can be natural or unnatural (synthetic) polymers. Typically, polymers in accordance with the present invention are organic polymers. Non-limiting examples include peptides or proteins. In some cases, additional moieties may also be present in the polymer, for example biological moieties such as those described below.

Polymers can be homopolymers or copolymers comprising two or more monomers. Copolymers, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. In terms of sequence, copolymers can be random, block, or comprise a combination of random and block sequences.

Block copolymers may have two (a diblock copolymer), three (a triblock copolymer), or more numbers of distinct blocks. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties {e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water. In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise taken up by such cells. Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, PLGA, polycaprolactone, or copolymers or derivatives including these and/or other polymers. In certain embodiments, the biodegradable polymer is selected from the group consisting of: poly(lactic-co-glycolic acid (PLGA), polylactic acid (PLA), polyglycolic acid (PGA), polyglutamic acid, polycaprolatone (PCL), polysebacid acid (PS), chitosan, gelatin, albumin, and PAC.

In certain embodiments, contemplated biocompatible polymers may be biodegradable, i.e., the polymer is able to degrade, chemically and/or biologically, within a physiological environment, such as within the body. Preferably, the biodegradable polymer and its degradation byproducts are biocompatible. For instance, a contemplated polymer may be one that hydrolyzes spontaneously upon exposure to water (e.g., within a subject), or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other non-polymeric moieties) may be on the order of days, weeks, months, or years, depending on the polymer. The polymers may be biologically degraded, e.g., by enzymatic activity or cellular machinery, in some cases, for example, through exposure to a lysozyme {e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide {e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly(4-hydroxy-L-proline ester), poly[alpha.-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85: 15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGAPEG block copolymer), may be selected to optimize for various parameters such as water uptake, biologically active agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments.

In some embodiments, polymers can be degradable polyesters bearing cationic side chains. Examples of these polyesters include poly(L-lactide-co-L-lysine), poly(serine ester), poly(4-hydroxy-L-proline ester). Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer. It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics.

For example, the molecular weight of the polymer can be adjusted such that the particle biodegrades in the subject being treated within the desired period of time (for example, about 1-2 weeks or about 6-7 weeks). In addition, the time can include 2-3 weeks, 3-4 weeks, 4-5 weeks, 5-6 weeks, and 7-8 weeks, etc.).

A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000. An exemplary therapeutic nanoparticle may include about 10 to about 99 weight percent poly(lactic) acid-poly(ethylene)glycol copolymer or poly (lactic)-co-poly(glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-copoly(glycolic) acid-poly(ethylene)glycol copolymer. Exemplary poly(lactic) acid-poly(ethylene)glycol copolymers can include a number average molecular weight of about 2 to about 200 kDa of poly(lactic) acid and a number average molecular weight of about 2 kDa to about 10 kDa of poly(ethylene)glycol.

Disclosed nanoparticles optionally include about 1 to about 50 weight percent poly(lactic) acid or poly(lactic) acid co-poly(glycolic) acid (which does not include PEG), or may optionally include about 1 to about 50 weight percent, or about 10 to about 50 weight percent or about 30 to about 50 weight percent poly(lactic) acid or poly(lactic) acid-copoly(glycolic) acid. For example, poly(lactic) or poly (lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

In certain embodiments, the polymers of the nanoparticles can be conjugated to a lipid. The polymer can be, for example, a lipid-terminated PEG. As described below, the lipid portion of the polymer can be used for self assembly with another polymer, facilitating the formation of a nanoparticle. For example, a hydrophilic polymer could be conjugated to a lipid that will self-assemble with a hydrophobic polymer.

In some embodiments, lipids are oils. In general, any oil known in the art can be conjugated to the polymers used in the invention. In some embodiments, an oil can comprise one or more fatty acid groups or salts thereof. In some embodiments, a fatty acid group can comprise digestible, long chain (e.g., C8-C50), substituted or unsubstituted hydrocarbons. In some embodiments, a fatty acid group can be a Cio-Cio fatty acid or salt thereof. In some embodiments, a fatty acid group can be a $C_{15}$-C2o fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

C. Targeting Moieties

Provided herein are targeted nanoparticle delivery systems comprising nanoparticles that include an optional targeting moiety, i.e., a moiety able to bind to or otherwise associate with a biological entity, for example, a membrane component, a cell surface receptor, prostate specific membrane antigen, or the like. A targeting moiety present on the surface of the nanoparticle allows the nanoparticle to become localized at a particular targeting site, for instance, a tumor, a disease site, a tissue, an organ, a type of cell, etc. As such, the nanoparticle is "target specific." The drug or other payload or gene construct may then, in some cases, be released from the particle and allowed to interact locally with the particular targeting site.

In one set of embodiments, a targeting portion may cause the nanoparticles to become localized to a tumor {e.g. a solid tumor) a disease site, a tissue, an organ, a type of cell, etc. within the body of a subject, depending on the targeting moiety used. For example, an Fn14 monoclonal antibody can become localized to a Fn14 cell surface receptor on a solid tumor, e.g. glioblastoma tumor or glioblastoma cancer cells, or on a breast cancer cell. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human, and the like.

D. Small Molecules

Contemplated targeting moieties include small molecules. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol. In some embodiments, small molecule targeting moieties that may be used to target cells associated with glioblastoma tumors include thiol and indole thiol derivatives, such as 2-MPPA and 3-(2-mercaptoethyl)-1H-indole-2-carboxylic acid derivatives. In some embodiments, for example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide.

Appropriate small molecule targeting moieties suitable for breast cancer cells and breast tumors, including metastatic breast tumors, included, for example, folate, PSMA ligand, aptamers, peptide ligands, and anisamides. Preferred small molecule targeting moieties for breast cancer include folate, aptamers, and peptide ligands, and most preferably peptide ligands.

E. Receptor Ligands

In some embodiments, a targeting moiety may be a naturally occurring or synthetic ligand for a cell surface receptor, e.g., a growth factor, cytokine, hormone, LDL, transferrin, etc. Zhou et al., Mol. Cancer Ther. 13(11):2688-2705, 2014 also describes suitable receptor ligands for use with the invention. Development of human serine protease-based therapeutics targeting Fn14 and identification of Fn14 as a new target overexpressed in TNBC (see Id., where the Fn14 ligand TWEAK is used to target a cytotoxin to Fn14-positive breast tumors).

F. Antibodies

A targeting moiety can be an antibody or binding portion thereof, including single chain targeting moieties. Procedures such as phage display can be used. In one embodiment, a disclosed nanoparticle includes a targeting moiety that is an Fn14 monoclonal antibody, ITEM4, ITEM4-SH, ITEM4-scFv, or ITEM4 Fab. Other antibodies are contemplated that are available commercially (e.g., ITEM1) to target Fn14-positive tumors as described in Johnston et al., Targeting of Fn14 Prevents Cancer-Induced Cachexia and Prolongs Survival. Cell, 162(6): 1365-1378, 2015.

The amino acids of an anti-Fn14 antibody or antigen-binding fragment thereof that interacts with the Fn14 protein are preferably not mutated (or, if mutated, replaced by a conserved amino acid residue); in one embodiment of a variant of the ITEM4 antibody or a variant of a ITEM4 antibody is not changed.

In one embodiment, the antibody or antigen-binding fragment does not cross-react with other TNF and TNFR family members. An antibody or antigen-binding fragment, described herein can be, for example, a humanized antibody, a fully human antibody, a monoclonal antibody, a single chain antibody, a monovalent antibody, a polyclonal antibody, a chimeric antibody, a multispecific antibody (e.g., a bispecific antibody), a multivalent antibody, an $F^A$ fragment, an $F(^A)_2$ fragment, an Fab' fragment, an $F_{sc}$ fragment, or an $F_v$ fragment. An antibody or antigen-binding fragment thereof described herein may be "multispecific," e.g., bispecific, trispecific or of greater multispecificity, meaning that it recognizes and binds to two or more different epitopes present on one or more different antigens (e.g., proteins) at the same time. Thus, whether a binding molecule is "monospecfic" or "multispecific," e.g., "bispecific," refers to the number of different epitopes with which the binding molecule reacts. Multispecific antibodies may be specific for different epitopes of an Fn14 protein, or may be specific for Fn14 as well as for a heterologous epitope, such as a heterologous polypeptide or solid support material.

As used herein the term "valent" (as used in "multivalent antibody") refers to the number of potential binding domains, e.g., antigen binding domains, present in a binding molecule. Each binding domain specifically binds one epitope. When a binding molecule comprises more than one binding domain, each binding domain may specifically bind the same epitope (for an antibody with two binding domains, termed "bivalent monospecific") or to different epitopes (for an antibody with two binding domains, termed "bivalent bispecific"). An antibody may also be bispecific and bivalent for each specificity (termed "bispecific tetravalent antibodies"). In another embodiment, tetravalent minibodies or domain deleted antibodies can be made. Bispecific bivalent antibodies, and methods of making them, are described, for instance in U.S. Pat. Nos. 5,731,168; 5,807,706; 5,821,333; and U.S. Application Publication Nos. 2003/020734 and 2002/0155537, the disclosures of all of which are incorporated by reference herein. Bispecific tetravalent antibodies, and methods of making them, are described, for instance, in WO 02/096948 and WO 00/44788, the disclosures of both of which are incorporated by reference herein. See generally, PCT publications WO 93/17715; WO 92/08802; WO 91/00360; W 92/05793; WO 2007/109254; U.S. Pat. Nos. 4,474,893; 4,714,681; 4,925,648; 5,573,920; 5,601,819). These references are all incorporated by reference herein.

In certain embodiments, an anti-Fn14 antibody, e.g., one or the two heavy chains of the antibody, is linked to one or more scFv to form a bispecific antibody. In other embodiments, an anti-Fn14 antibody is in the form of an scFv that is linked to an antibody to form a bispecific molecule. Antibody-scFv constructs are described, e.g., in WO 2007/109254.

The heavy and light chains of the antibody can be substantially full-length. The protein can include at least one, and optionally two, complete heavy chains, and at least one, and optionally two, complete light chains or can include an antigen-binding fragment. In yet other embodiments, the antibody has a heavy chain constant region chosen from, e.g., IgGI, IgG2, IgG3, IgG4, IgM, IgA1, IgA2, IgD, and IgE. Typically, the heavy chain constant region is human or a modified form of a human constant region. In another embodiment, the antibody has a light chain constant region chosen from, e.g., kappa or lambda, particularly, kappa (e.g., human kappa).

In certain embodiments, the binding of antibodies or antigen binding fragments thereof results in cross-linking or clustering of the Fn14 receptor on the cell surface. For example, antibodies or antigen-binding fragments thereof may form a multimer, e.g., by binding to protein A, or may be multivalent. An antibody or antigen-binding fragment described herein can be modified to enhance effector function, e.g., so as to enhance antigen-dependent cell-mediated cytotoxicity (ADCC) and/or complement dependent cytotoxicity (CDC) of the antibody or enhance cross-linking of the target receptor/Fn14. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al., Anti-Cancer Drug Design 3:219-230 (1989). In addition, an antibody can be defucosylated such that the modified antibody exhibits enhanced ADCC as compared to the non-defucosylated form of the antibody. See, e.g., WO2006089232.

This disclosure includes, but is not limited to specific examples of anti-Fn14 antibodies, such as ITEM4, ITEM4-SH, or ITEM4-scFv, or ITEM4 Fab. Particular antibodies, such as these, can be made, for example, by preparing and expressing synthetic genes that encode the recited amino acid sequences or by mutating human germline genes to provide a gene that encodes the recited amino acid sequences. Moreover, these antibodies and other anti-Fn14 antibodies (e.g., ITEM1 or ITEM2) can be produced, e.g., using one or more methods. Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228: 1315-1317; WO 92/18619; WO 91/17271; WO 92/20791; WO 92/15679; WO 93/01288; WO 92/01047; WO 92/09690; and WO 90/02809. The display of Fab' on phage is described, e.g., in U.S. Pat. Nos. 5,658,727; 5,667,988; and 5,885,793, in addition to the use of display libraries, other methods can be used to obtain a Fn14-binding antibody. For example, the Fn14 protein or a peptide thereof can be used as an antigen in a non-human animal, e.g., a rodent, e.g., a mouse, hamster, or rat. In addition, cells transfected with a cDNA encoding Fn14 can be injected into a non-human animal as a means of producing antibodies that effectively bind the cell surface Fn14 protein.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, U.S. 2003-0070185, WO 96/34096, and WO 96/33735. In another embodiment, a monoclonal antibody is obtained from the non-human animal, and then modified, e.g., humanized or deimmunized. Winter describes an exemplary CDR-grafting method that may be used to prepare humanized antibodies described herein (U.S. Pat. No. 5,225, 539). All or some of the CDRs of a particular human antibody may be replaced with at least a portion of a non-human antibody. It may only be necessary to replace the CDRs required for binding or binding determinants of such CDRs to arrive at a useful humanized antibody that binds to Fn14. Humanized antibodies can be generated by replacing sequences of the Fv variable region that are not directly involved in antigen binding with equivalent sequences from human Fv variable regions. General methods for generating humanized antibodies are provided by Morrison, S. L, (1985) Science 229: 1202-1207, by Oi et al. (1986) Bio-Techniques 4:214, and by U.S. Pat. Nos. 5,585,089; 5,693, 761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target, as described above, from germline immunoglobulin genes, or from synthetic constructs. The recombinant DNA encoding the humanized antibody can then be cloned into an appropriate expression vector.

Human germline sequences, for example, are disclosed in Tomlinson, L A, et al. (1992) J Mol. Biol. 227:776-798; Cook, G. P. et al. (1995) Immunol. Today 16: 237-242; Chothia, D. et al. (1992) J Mol. Bio. 227:799-817; and Tomlinson et al. (1995) EMBO J 14:4628-4638. The V BASE directory provides a comprehensive directory of human immunoglobulin variable region sequences (compiled by Tomlinson, L A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

A non-human Fn14-binding antibody may also be modified by specific deletion of human T cell epitopes or "deimmunization" by the methods disclosed in WO 98/52976 and WO 00/34317. Briefly, the heavy and light chain variable regions of an antibody can be analyzed for peptides that bind to MHC Class II. These peptides represent potential T-cell epitopes (as defined in WO 98/52976 and W 00/34317). For detection of potential T-cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable regions, or preferably, by single amino acid substitutions. As far as possible, conservative substitutions are made. Often, but not exclusively, an amino acid common to a position in human germline antibody sequences may be used. After the deimmunizing changes are identified, nucleic acids encoding $V_H$ and VL can be constructed by mutagenesis or other synthetic methods (e.g., de novo synthesis, cassette replacement, and so forth). A mutagenized variable sequence can, optionally, be fused to a human constant region, e.g., human IgG1 or kappa constant regions.

Other methods for humanizing antibodies can also be used. For example, other methods can account for the three dimensional structure of the antibody, framework positions that are in three dimensional proximity to binding determinants, and immunogenic peptide sequences. See, e.g., WO 90/07861; U.S. Pat. Nos. 5,693,762; 5,693,761; 5,585,089; 5,530,101; and U.S. Pat. No. 6,407,213; Tempest et al. (1991) Biotechnology 9:266-271. Still another method is termed "humaneering" and is described, for example, in U.S. 2005-008625. The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies may have mutations in the CH2 region of the heavy chain that reduce or alter effector function, e.g., Fc receptor binding and complement activation. For example, antibodies may have mutations such as chose described in U.S. Pat. Nos. 5,624, 821 and 5,648,260. Antibodies may also have mutations that stabilize the disulfide bond-between the two heavy chains of an immunoglobulin, such as mutations in the hinge region of IgG4, as disclosed in the art (e.g., Angal et al., (1993) Mol. Immunol. 30:105-08). See also, e.g., U.S. 2005-0037000.

In one embodiment, an anti-Fn14 antibody is modified, e.g., by mutagenesis, to provide a pool of modified antibodies. The modified antibodies are then evaluated to identify one or more antibodies which have altered functional properties (e.g., improved binding, improved stability, reduced antigenicity, or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used.

In some implementations, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements, in one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identity an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criteria for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but can include using two germline sequences that separately contribute to the amino-terminal portion and the carboxy-terminal portion. In other implementations, more than one or two germline sequences are used, e.g., to form a consensus sequence.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies may be accomplished chemically or enzymatically as described in the art (Hakimuddin et al. (1987) Arch. Biochem. Biophys. 259:52; Edge et al. (1981) Anal. Biochem, 1 18: 131; and Thotakura et al. (1987) Meth. Enzymol. 138:350). See, e.g., U.S. Pat. No. 5,869,046 for a modification that increases in vivo half-life by providing a salvage receptor binding epitope.

In one embodiment, an antibody has CDR sequences that differ only insubstantially from those of described. Insubstantial differences include minor amino acid changes, such as substitutions of 1 or 2 out of any of typically 5-7 amino acids in the sequence of a CDR, e.g., a Chothia or Kabat CDR. Typically an amino acid is substituted by a related amino acid having similar charge, hydrophobic, or stereochemical characteristics. Such substitutions would be within the ordinary skills of an artisan. Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al. (1991) J Immun. 147:2657-62; Morgan et al. (1995) Immunology 86:319-24), or changing the species from which the constant region is derived. The anti-Fn14 antibodies can be in the form of full length antibodies, or in the form of fragments of antibodies, e.g., Fab, F(ab')$_2$, Fd, dAb, and scFv fragments. A fragment of an antibody can be an antigen-binding fragment, such as a variable region, e.g., VH or VL. Additional forms include a protein that includes a single variable domain, e.g., a camel or camelized domain. See, e.g., U.S. 2005-0079574 and Davies et al. (1996) Protein Eng. 9(6):531-7.

Targeting moieties disclosed herein are typically conjugated to a disclosed polymer or copolymer (e.g. PLA-PEG), and such a polymer conjugate may form part of a disclosed nanoparticle. For example, a disclosed therapeutic nanoparticle may optionally include about 0.2 to about 10 weight percent of a PLA-PEG or PLGA-PEG, wherein the PEG is functionalized with a targeting ligand (e.g. PLA-Fn14 monoclonal antibody). Such a targeting ligand may be, in some embodiments, covalently bound to the PEG, for example, bound to the PEG via a methoxy-PEG5k-amine linker by EDC carbodiimide chemistry.

G. Nanoparticles

Disclosed nanoparticles may have a substantially spherical shape (i.e., the particles generally appear to be spherical), or nonspherical configuration. For instance, the particles, upon swelling or shrinkage, may adopt a non-spherical configuration. In some cases, the particles may include polymeric blends. For instance, a polymer blend may be formed that includes a first polymer comprising a targeting moiety and a biocompatible polymer, and a second polymer comprising a biocompatible polymer but not comprising the targeting moiety. By controlling the ratio of the first and second polymers in the final polymer, the concentration and location of targeting moiety in the final polymer may be readily controlled to any suitable degree.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 200 nm, less than about 150 nm, less than about 100 nm, less than about 50 nm, less than about 30 nm, less than about 10 nm, less than about 3 nm, or less than about 1 nm in some cases. In particular embodiments, the nanoparticle of the present invention has a diameter of about 20 nm-200 nm or about 4 nm-200 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle. In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body will also be isolated from the drug. In certain embodiments, polymer particles having more than one polymer or macromolecule present, and libraries involving such polymers or macromolecules.

For example, in one set of embodiments, particles may contain more than one distinguishable polymers (e.g., copolymers, e.g., block copolymers), and the ratios of the two (or more) polymers may be independently controlled, which allows for the control of properties of the particle. For instance, a first polymer may be a polymeric conjugate comprising a targeting moiety and a biocompatible portion, and a second polymer may comprise a biocompatible portion but not contain the targeting moiety, or the second polymer may contain a distinguishable biocompatible portion from the first polymer. Control of the amounts of these polymers within the polymeric particle may thus be used to control various physical, biological, or chemical properties of the particle, for instance, the size of the particle (e.g., by varying the molecular weights of one or both polymers), the surface charge (e.g., by controlling the ratios of the polymers if the polymers have different charges or terminal groups), the surface hydrophilicity (e.g., if the polymers have different molecular weights and/or hydrophilicities), the surface density of the targeting moiety (e.g., by controlling the ratios of the two or more polymers), etc.

As a specific example, a particle can comprise a first polymer comprising a first biocompatible portion and a targeting moiety, and a second polymer comprising a second biocompatible portion different from the first biocompatible portion (e.g., having a different composition, a substantially different number of repeat units, etc.) and the targeting moiety. As yet another example, a first polymer may comprise a biocompatible portion and a first targeting moiety, and a second polymer may comprise a biocompatible portion and a second targeting moiety different from the first targeting moiety. For example, disclosed herein is a therapeutic polymeric nanoparticle capable of binding to a target, comprising a first non-functionalized polymer; an optional second non-functionalized polymer; a functionalized polymer comprising a targeting moiety; and a biologically active agent; wherein said nanoparticle comprises about 15 to about 300 molecules of functionalized polymer, or about 20 to about 200 molecule, or about 3 to about 100 molecules of functionalized polymer.

In a particular embodiment, the polymer of the first or second macromolecules of the nanoparticle of the invention is PLA, PLGA, or PEG, or copolymers thereof. In a specific embodiment, the polymer of the first macromolecule is a PLGA-PEG copolymer, and the second macromolecule is a PLGA-PEG copolymer, or a PLA-PEG copolymer. For example, exemplary nanoparticle may have a PEG corona with a density of about 0.065 g/cm, or about 0.01 to about 0.10 g/cm. Disclosed nanoparticles may be stable (e.g. retain substantially all biologically active agents) for example in a solution that may contain a saccharide, for at least about 3 days, about 4 days or at least about 5 days at room temperature, or at 25° C.

In some embodiments, disclosed nanoparticles may also include a fatty alcohol, which may increase the rate of drug release. For example, disclosed nanoparticles may include a C8-C30 alcohol such as cetyl alcohol, octanol, stearyl alcohol, arachidyl alcohol, docosonal, or octasonal. Nanoparticles may have controlled release properties, e.g., may be capable of delivering an amount of biologically active agent to a patient, e.g., to specific site in a patient, over an extended period of time, e.g., over 1 day, 1 week, or more. In some embodiments, disclosed nanoparticles substantially immediately release (e.g. over about 1 minute to about 30 minutes) less than about 2%, less than about 5%, or less than about 10% of a biologically active agent (e.g. a therapeutic agent such as taxane), for example when places in a phosphate buffer solution at room temperature and/or at 37° C.

For example, disclosed nanoparticles that include a biologically active agent can, in some embodiments, may release the biologically active agent when placed in an aqueous solution at e.g., 25° C. with a rate substantially corresponding to a) from about 0.01 to about 20% of the total biologically active agent is released after about 1 hour; b) from about 10 to about 60% of the biologically active agent is released after about 8 hours; c) from about 30 to about 80% of the total biologically active agent is released after about 12 hours; and d) not less than about 75% of the total is released after about 24 hours.

In some embodiments, after administration to a subject or patient of a disclosed nanoparticle or a composition that includes a disclosed nanoparticle, the peak plasma concentration ($C_{max}$) of the biologically active agent in the patient substantially higher as compared to a $C_{max}$ of the biologically active agent if administered alone (e.g., not as part of a nanoparticle).

In another embodiment, a disclosed nanoparticle including a biologically active agent, when administered to a subject, may have a $t_{max}$ of biologically active agent substantially longer as compared to a $t_{max}$ of the biologically active agent administered alone. As a specific example, the nanoparticle may contain polymers including a relatively hydrophobic biocompatible polymer and a relatively hydrophilic targeting moiety, such that, during nanoparticle formation, a greater concentration of the hydrophilic targeting moiety is exposed on the surface and a greater concentration of the hydrophobic biocompatible polymer is present within the interior of the particle.

In some embodiments, the biocompatible polymer is a hydrophobic polymer. Non-limiting examples of biocompatible polymers include polylactide, polyglycolide, and/or poly(lactide-co-glycolide). In a different embodiment, this disclosure provides for a nanoparticle comprising 1) a polymeric matrix; 2) optionally, an amphiphilic compound or layer that surrounds or is dispersed within the polymeric matrix forming a continuous or discontinuous shell for the particle; 3) a non-functionalized polymer that may form part of the polymeric matrix, and 4) a low molecular weight PSMA ligand covalently attached to a polymer, which may form part of the polymeric matrix. For example, an amphiphilic layer may reduce water penetration into the nanoparticle, thereby enhancing drug encapsulation efficiency and slowing drug release. As used herein, the term "amphiphilic"

refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the invention, the amphiphilic compound can be, but is not limited to, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-snglycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and .beta.-acyl-y-alkyl phospholipids. Examples of phospholipids include, but are not limited to, phosphatidylcholines such as dioleoylphosphatidylcholine, dimyristoylphosphatidylcholine, ipentadecanoylphosphatidylcholine dilauroylphosphatidylcholine, dipalmitoylphosphatidylcholine (DPPC),distearoylphosphatidylcholine (DSPC), iarachidoylphosphatidylcholine (DAPC), dibehenoylphosphatidylcholine (DBPC), itricosanoylphosphatidylcholine (DTPC), dilignoceroylphatidylcholine (DLPC); ndphosphatidylethanolamines such as dioleoylphosphatidylethanolamine or 1-hexadecyl-2-almitoylglycerophos phoethanolamine.

Synthetic phospholipids with asymmetric acyl chains (e.g., with one acyl chain of 6 carbons and another acyl chain of 12 carbons) may also be used. In a particular embodiment, an amphiphilic component that can be used to form an amphiphilic layer is lecithin, and, in particular, phosphatidylcholine. Lecithin is an amphiphilic lipid and, as such, forms a phospholipid bilayer having the hydrophilic (polar) heads facing their surroundings, which are oftentimes aqueous, and the hydrophobic tails facing each other. Lecithin has an advantage of being a natural lipid that is available from, e.g., soybean, and already has FDA approval for use in other delivery devices. In addition, a mixture of lipids such as lecithin is more advantageous than one single pure lipid. In certain embodiments a disclosed nanoparticle has an amphiphilic monolayer, meaning the layer is not a phospholipid bilayer, but exists as a single continuous or discontinuous layer around, or within, the nanoparticle. The amphiphilic layer is "associated with" the nanoparticle of the invention, meaning it is positioned in some proximity to the polymeric matrix, such as surrounding the outside of the polymeric shell, or dispersed within the polymers that make up the nanoparticle.

PEG density, targeting molecule type and/or density, and polymer type may be altered in certain embodiments to optimize Fn14 binding. Table 1 is an example of a summary of formulation variables for synthesis and screening of Fn14-targeted BPNs. The preferred combination is presented in italics. Table 5 is an example of a summary of formulation variables for synthesis and screening of Fn14-targeted nanoparticles for breast cancer.

TABLE 1

Summary of Formulation Variables.

| Polymers | Therapeutics | Targeting Molecules | Formulation Variables | Characterization Methods |
|---|---|---|---|---|
| PLGA (50:50) | Cisplatin | ITEM4 | Polymer blend composition | Dynamic light scattering (size, ζ-potential) |
| PLGA (75:25) | Doxorubicin | ITEM4 scFv | PEG MW (2 kDa, 5 kDa, 10 kDa) | Electron microscopy (morphology) |
| PLA | Etoposide | ITEM4 Fab | | |
| PGA | Paclitaxel | TWEAK | | |
| PAA | Small molecule drugs | | PEG surface density (PEG:polymer ratio) | NMR & protein assays (quantitation of PEG density and targeting molecule density) |
| | Pathway inhibitors | | Targeting molecule density | |

H. Preparation of Nanoparticles

Another aspect of this disclosure is directed to methods of making the disclosed nanoparticles. In some embodiments, 40-nm to 200-nm red fluorescent COOH-modified polystyrene (PS) particles were covalently modified with methoxy (MeO)-PEG-amine (NH2) (5 kDA MW) by carboxyl amine reaction, following a modified protocol known in the art. These two protocols were combined and optimized to obtain dense PEG coatings, a near-neutral ζ-potential, and low PDI, for 40 nm-200 nm PS particles. In embodiments to formulate brain tissue penetrating coated nanoparticles, 100 nm carboxylate-modified polystyrene (PS-COOH) nanoparticles were covalently modified with methoxy-PEG5k-amine by EDC carbodiimide chemistry, following a modified protocol described previously. In embodiments to formulate nanoparticles preferred for treatment of breast cancer and breast cancer metastasis, coated nanoparticles, 20 nm, 60 nm, and 100 nm carboxylate-modified polystyrene (PS-COOH) nanoparticles were covalently modified with methoxy-PEG5k-amine by EDC carbodiimide chemistry, following a modified protocol described previously.

In other embodiments, coated ITEM4 nanoparticles were prepared using a different proportion of PEG (methoxy-PEG5k-amine to malemide-PEG5k-amine) for initial particle PEGylation. Specifically, 10 mol % and 50 mol % of maleimide-PEG5k-amine was used for CNP-ITEM4 (low) and CNP-ITEM4 (high) nanoparticles, respectively. ITEM 4-SH was conjugated onto the surface of the nanoparticles containing maleimide-functionalized PEG by maleimide-thiol chemistry.

I. Biologically Active Agents

According to the present invention, any biologically active agents including, for example, therapeutic agents (anti-cancer agents, anti-AD agents, anti-PD agents, anti-HD agents, anti-epilepsy agents), diagnostic agents (e.g. contrast agents; radionuclides; and fluorescent, luminescent, and magnetic moieties), prophylactic agents (e.g. vaccines), nutraceutical agents (e.g. vitamins, minerals, etc.), imaging agents (e.g., via magnetic resonance imaging, positron emission imaging, radio-isotope imagining) and/or gene therapy agents (e.g. nucleic acids such as RNA and DNA) may be delivered by the disclosed nanoparticles. Exemplary biologically active agents to be delivered in accordance with the present invention include, but are not limited to, drugs, small molecules (e.g. cytotoxic agents), nucleic acids (e.g., DNA, RNA, siRNA, RNAi, and microRNA agents), proteins (e.g. antibodies), peptides, lipids, carbohydrates, hormones, metals, radioactive elements and compounds, vaccines, immunological agents, etc., and/or combinations thereof. Molecular imaging agents are known in the art and are readily available in the MICAD database developed by the NIH and online. They enable the visualization of phenomena with cellular and subcellular level resolutions and therefore have enormous potential in improving disease diagnosis and therapy assessment and are known in the art. In certain embodiments, the nanoparticle has from a 1% to 100% load capacity for the biologically active agent. In some embodiments, the therapeutic agent to be delivered is a drug useful in the treatment of cancer (e.g., brain cancer, specifically glioblastoma).

In certain embodiments, a targeting moiety, if used, may target or cause the nanoparticle to become localized at specific portions within a subject, and the payload may be delivered to those portions. In a particular embodiment, the drug or other payload may is released in a controlled release manner from the particle and allowed to interact locally with the particular targeting site (e.g., a tumor). Controlled release is defined above, and encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The biologically active agent may be a therapeutic agent such a taxane such as paclitaxel (or its derivatives such as DHA-paclitaxel or PG-paclitaxel) or docetaxel. In one set of embodiments, the payload is a drug or a combination of more than one drug. Such particles may be useful, for example, in embodiments where a targeting moiety may be used to direct a particle containing a drug to a particular localized location within a subject, e.g., to allow localized delivery of the drug to occur. For example, biodegradable NPs may be composed of block copolymers of poly(lactic-co-glycolic acid) (PLGA) and PEG and loaded with 2.5% wt % paclitaxel. Exemplary therapeutic agents include chemotherapeutic agents such as doxorubicin (adriamycin), gemcitabine (gemzar), daunorubicin, procarbazine, mitomycin, cytarabine, etoposide, methotrexate, venorelbine, 5-fluorouracil (5-FU), vinca alkaloids such as vinblastine or vincristine; bleomycin, paclitaxel (taxol), docetaxel (taxotere), aldesleukin, asparaginase, busulfan, carboplatin, cladribine, camptothecin, CPT-11, 1O-hydroxy-7-ethyl-camptothecin (SN38), dacarbazine, S-I capecitabine, ftorafur, 5'deoxyfluorouridine, UFT, eniluracil, deoxycytidine, 5-azacytosine, 5-azadeoxycytosine, allopurinol, 2-chloroadenosine, trimetrexate, aminopterin, methylene-10-deazaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, and combinations thereof. Non-limiting examples of potentially suitable drugs include anticancer agents, including, for example, docetaxel, mitoxantrone, and mitoxantrone hydrochloride.

In another embodiment, the payload may be an anti-cancer drug such as 20-epi-1,25 dihydroxyvitamin D3, 4-ipomeanol, 5-ethynyluracil, 9-dihydrotaxol, abiraterone, acivicin, aclarubicin, acodazole hydrochloride, acronine, acylfiilvene, adecypenol, adozelesin, aldesleukin, all-tk antagonists, altretamine, ambamustine, ambomycin, ametantrone acetate, amidox, amifostine, aminoglutethimide, aminolevulinic acid, amrubicin, amsacrine, anagrelide, anastrozole, andrographolide, angiogenesis inhibitors, antagonist D, antagonist G, antarelix, anthramycin, antidorsalizdng morphogenetic protein-1, antiestrogen, antineoplaston, antisense oligonucleotides, aphidicolin glycinate, apoptosis gene modulators, apoptosis regulators, apurinic acid, ARA-CDP-DLPTBA, arginine deaminase, asparaginase, asperlin, asulacrine, atamestane, atrimustine, axinastatin 1, axinastatin 2, axinastatin 3, azacitidine, azasetron, azatoxin, azatyrosine, azetepa, azotomycin, baccatin III derivatives, balanol, batimastat, benzochlorins, benzodepa, benzoylstaurosporine, beta lactam derivatives, beta-alethine, betaclamycin B, betulinic acid, BFGF inhibitor, bicalutamide, bisantrene, bisantrene hydrochloride, bisazuidinylspermine, bisnafide, bisnafide dimesylate, bistratene A, bizelesin, bleomycin, bleomycin sulfate, BRC/ABL antagonists, breflate, brequinar sodium, bropirimine, budotitane, busulfan, buthionine sulfoximine, cactinomycin, calcipotriol, calphostin C, calusterone, camptothecin derivatives, canarypox IL-2, capecitabine, caraceraide, carbetimer, carboplatin, carboxamide-amino-triazole, carboxyamidotriazole, carest M3, carmustine, earn 700, cartilage derived inhibitor, carubicin hydrochloride, carzelesin, casein kinase inhibitors, castanospermine, cecropin B, cedefingol, cetrorelix, chlorambucil, chlorins, chloroquinoxaline sulfonamide, cicaprost, cirolemycin, cisplatin, cis-porphyrin, cladribine, clomifene analogs, clotrimazole, collismycin A, collismycin B, combretastatin A4, combretastatin analog, conagenin, crambescidin 816, crisnatol, crisnatol mesylate, cryptophycin 8, cryptophycin A derivatives, curacin A, cyclopentanthraquinones, cyclophosphamide, cycloplatam, cypemycin, cytarabine, cytarabine ocfosfate, cytolytic factor, cytostatin, dacarbazine, dacliximab, dactinomycin, daunorubicin hydrochloride, decitabine, dehydrodidemnin B, deslorelin, dexifosfamide, dexormaplatin, dexrazoxane, dexverapamil, dezaguanine, dezaguanine mesylate, diaziquone, didemnin B, didox, diethyhiorspermine, dihydro-5-azacytidine, dioxamycin, diphenyl spiromustine, docetaxel, docosanol, dolasetron, doxifluridine, doxorubicin, doxorubicin hydrochloride, droloxifene, droloxifene citrate, dromostanolone propionate, dronabinol, duazomycin, duocannycin SA, ebselen, ecomustine, edatrexate, edelfosine, edrecolomab, eflomithine, eflomithine hydrochloride, elemene, elsarnitrucin, emitefur, enloplatin, enpromate, epipropidine, epirubicin, epirubicin hydrochloride, epristeride, erbulozole, erythrocyte gene therapy vector system, esorubicin hydrochloride, estramustine, estramustine analog, estramustine phosphate sodium, estrogen agonists, estrogen antagonists, etanidazole, etoposide, etoposide phosphate, etoprine, exemestane, fadrozole, fadrozole hydrochloride, fazarabine, fenretinide, filgrastim, finasteride, flavopiridol, flezelastine, floxuridine, fluasterone, fludarabine, fludarabine phosphate, fluorodaunorunicin hydrochloride, fluorouracil, fluorocitabine, forfenimex, formestane, fosquidone, fostriecin, fostriecin sodium, fotemustine, gadolinium texaphyrin, gallium nitrate, galocitabine, ganirelix, gelatinase inhibitors, gemcitabine, gemcitabine hydrochloride, glutathione inhibitors, hepsulfam, heregulin, hexamethylene bisacetamide, hydroxyurea, hypericin, ibandronic acid, idarubicin, idarubicin hydrochloride, idoxifene, idramantone, ifosfamide, ihnofosine, ilomastat, imidazoacridones, imiquimod, immunostimulant peptides, insulin-like growth factor-1 receptor inhibitor, interferon agonists, interferon alpha-2A, interferon alpha-2B, interferon alpha-N1, interferon alpha-N3, interferon beta-IA, interferon gamma-IB, interferons, interleukins, iobenguane, iodoxorubicin, iproplatm, irinotecan, irinotecan hydrochloride, iroplact, irsogladine, isobengazole, isohomohalicondrin B, itasetron, jasplakinolide, kahalalide F, lamellarin-N triacetate, lanreotide, lanreotide acetate, leinamycin, lenograstim, lentinan sulfate, leptolstatin, letrozole, leukemia inhibiting factor, leukocyte alpha interferon, leuprolide acetate, leuprolide/estrogen/progesterone, leuprorelin, levamisole, liarozole, liarozole hydrochloride, linear polyamine analog, lipophilic disaccharide peptide, lipophilic platinum compounds, lissoclinamide, lobaplatin, lombricine, lometrexol, lometrexol sodium, lomustine, lonidamine, losoxantrone, losoxantrone hydrochloride, lovastatin, loxoribine, lurtotecan, lutetium texaphyrin lysofylline, lytic peptides, maitansine, mannostatin A, marimastat, masoprocol, maspin, matrilysin inhibitors, matrix metalloproteinase inhibitors, maytansine, mechlorethamine hydrochloride, megestrol acetate, melengestrol acetate, melphalan, menogaril, merbarone, mercaptopurine, meterelin, methioninase, methotrexate, methotrexate sodium, metoclopramide, metoprine, meturedepa, microalgal protein kinase C inhibitors, MIF inhibitor, mifepristone, miltefosine, mirimostim, mismatched double stranded RNA, mitindomide, mitocarcin, mitocromin, mitogillin, mitoguazone, mitolactol, mitomalcin, mitomycin, mitomycin analogs, mitonafide, mitosper, mitotane, mitotoxin fibroblast growth factor-saporin, mitoxantrone, mitoxantrone hydrochloride, mofarotene, molgramostim, monoclonal antibody, human chorionic gonadotrophin, monophosphoryl lipid a/myobacterium cell wall SK, mopidamol, multiple drug resistance gene inhibitor, multiple tumor suppressor 1-based therapy, mustard anticancer agent, mycaperoxide B, mycobacterial cell wall extract, mycophenolic acid, myriaporone, n-acetyldinaline, nafarelin, nagrestip, naloxone/pentazocine, napavin, naphterpin, nartograstim, nedaplatin, nemorubicin, neridronic acid, neutral endopeptidase, nilutamide, nisamycin, nitric oxide modulators, nitroxide antioxidant, nitrullyn, nocodazole, nogalamycin, n-substituted benzamides, 06-benzylguanine, octreotide, okicenone, oligonucleotides, onapristone, ondansetron, oracin, oral cytokine inducer, ormaplatin, osaterone, oxaliplatin, oxaunomycin, oxisuran, paclitaxel, paclitaxel analogs, paclitaxel derivatives, palauamine, palmitoylrhizoxin, pamidronic acid, panaxytriol, panomifene, parabactin, pazelliptine, pegaspargase, peldesine, peliomycin, pentamustine, pentosan polysulfate sodium, pentostatin, pentrozole, peplomycin sulfate, perflubron, perfosfamide, perillyl alcohol, phenazinomycin, phenylacetate, phosphatase inhibitors, picibanil, pilocarpine hydrochloride, pipobroman, piposulfan, pirarubicin, piritrexim, piroxantrone hydrochloride, placetin A, placetin B, plasminogen activator inhibitor, platinum complex, platinum compounds, platinum-triamine complex, plicamycin, plomestane, porfimer sodium, porfiromycin, prednimustine, procarbazine hydrochloride, propyl bis-acridone, prostaglandin J2, prostatic carcinoma antiandrogen, proteasome inhibitors, protein A-based immune modulator, protein kinase C inhibitor, protein tyrosine phosphatase inhibitors, purine nucleoside phosphorylase inhibitors, puromycin, puromycin hydrochloride, purpurins, pyrazorurin, pyrazoloacridine, pyridoxylated hemoglobin polyoxyethylene conjugate, RAF antagonists, raltitrexed, ramosetron, RAS farnesyl protein transferase inhibitors, RAS inhibitors, RAS-GAP inhibitor, retelliptine demethylated, rhenium RE 186 etidronate, rhizoxin, riboprine, ribozymes, RH retinamide, RNAi, rogletimide, rohitukine, romurtide, roquinimex, rubiginone Bl, ruboxyl, safingol, safingol hydrochloride, saintopin, sarcnu, sarcophytol A, sargramostim, SDI1 mimetics, semustine, senescence derived inhibitor 1, sense oligonucleotides, signal transduction inhibitors, signal transduction modulators, simtrazene, single chain antigen binding protein, sizofiran, sobuzoxane, sodium borocaptate, sodium phenylacetate, solverol, somatomedin binding protein, sonermin, sparfosate sodium, sparfosic acid, sparsomycin, spicamycin D, spirogermanium hydrochloride, spiromustine, spiroplatin, splenopentin, spongistatin 1, squalamine, stem cell inhibitor, stem-cell division inhibitors, stipiamide, streptonigrin, streptozocin, stromelysin inhibitors, sulfinosine, sulofenur, superactive vasoactive intestinal peptide antagonist, suradista, suramin, swainsonine, synthetic glycosaminoglycans, talisomycin, tallimustine, tamoxifen methiodide, tauromustine, tazarotene, tecogalan sodium, tegafur, tellurapyrylium, telomerase inhibitors, teloxantrone hydrochloride, temoporfin, temozolomide, teniposide, teroxirone, testolactone, tetrachlorodecaoxide, tetrazomine, thaliblastine, thalidomide, thiamiprine, thiocoraline, thioguanine, thiotepa, thrombopoietin, thrombopoietin mimetic, thymalfasin, thymopoietin receptor agonist, thymotrinan, thyroid stimulating hormone, tiazofurin, tin ethyl etiopurpurin, tirapazamine, titanocene dichloride, topotecan hydrochloride, topsentin, toremifene, toremifene citrate, totipotent stem cell factor, translation inhibitors, trestolone acetate, tretinoin, triacetyluridine, triciribine, triciribine phosphate, trimetrexate, trimetrexate glucuronate, triptorelin, tropisetron, tubulozole hydrochloride, turosteride, tyrosine kinase inhibitors, tyrphostins, UBC inhibitors, ubenimex, uracil mustard, uredepa, urogenital sinus-derived growth inhibitory factor, urokinase receptor antagonists, vapreotide, variolin B, velaresol, veramine, verdins, verteporfin, vinblastine sulfate, vincristine sulfate, vindesine, vindesine sulfate, vinepidine sulfate, vinglycinate sulfate, vinleurosine sulfate, vinorelbine or vinorelbine tartrate, vinrosidine sulfate, vinxaltine, vinzolidine sulfate, vitaxin, vorozole, zanoterone, zeniplatin, zilascorb, zinostatin, zinostatin stimalamer, or zorubicin hydrochloride.

When treating breast cancer or metastatic breast cancer, preferred compounds for treatment, i.e., anti-breast cancer drugs, include chemotherapies (e.g., cisplatin, carboplatin, oxaliplatin, doxorubicin, paclitaxel, docetaxel), molecularly targeted therapies, and immunotherapies. Preferred anti-breast cancer drugs are paclitaxel, cisplatin, doxorubicin, and oxaliplatin.

The biologically active agent may be a therapeutic agent such as a drug used to treat Parkinson's disease which include L-dopa, selegiline, apomorphine and anticholinergics. L-dopa (levodihydroxy-phenylalanine) (sinemet) is a dopamine precursor which can cross the blood-brain barrier and be converted todopamine in the brain. Unfortunately, L-dopa has a short half-life in the body and it is typical after long use (i.e. after about 4-5 years) for the effect of L-dopa to become sporadic and unpredictable, resulting in fluctuations in motor function, dyskinesias and psychiatric side effects. Additionally, L-dopa can cause B vitamin deficiencies to arise. Selegiline (Deprenyl®, Eldepryl®) has been used as an alternative to L-dopa, and acts by reducing the breakdown of dopamine in the brain. Unfortunately, Selegiline becomes ineffective after about nine months of use. Apomorphine, a dopamine receptor agonist, has been used to treat Parkinson's disease, although is causes severe vomiting when used on its own, as well as skin reactions, infection, drowsiness and some psychiatric side effects. Systemically administered anticholinergic drugs (such as benzhexol and orphenedrme) have also been used to treat Parkinson's disease and act by reducing the amount of acetylcholine produced in the brain and thereby redress the dopamine/acetylcholine imbalance present in Parkinson's disease. Unfortunately, about 70% of patients taking systemically administered anticholinergics develop serious neuropsychiatric side effects, including hallucinations, as well as dyskinetic movements, and other effects resulting from wide anticholinergic distribution, including vision effects, difficulty swallowing, dry mouth and urine retention.

Biologically active agents such as therapeutic agents that are drugs for treatment of AD cannot cure AD or stop it from progressing, but they may help lessen symptoms, such as memory loss and confusion, for a limited time. The FDA has approved two types of medications—cholinesterase inhibitors (Aricept®, Exelon®, Razadyne®, Cognex®) and memantine (Namenda®)—to treat the cognitive symptoms (memory loss, confusion, and problems with thinking and reasoning) of Alzheimer's disease. As Alzheimer's progresses, brain cells die and connections among cells are lost, causing cognitive symptoms to worsen. While current medications cannot stop the damage Alzheimer's disease causes to brain cells, they may help lessen or stabilize symptoms for a limited time by affecting certain chemicals involved in carrying messages among the brain's nerve cells. Doctors sometimes prescribe both types of medications together. Some doctors also prescribe high doses of vitamin E for cognitive changes of Alzheimer's disease.

No treatments can alter the course of Huntington's disease. But therapeutic agents can lessen some symptoms of movement and psychiatric disorders. And multiple interventions can help a person adapt to changes in his or her abilities for a certain amount of time. Medication management is likely to evolve over the course of the disease, depending on the overall treatment goals. Also, drugs to treat some symptoms may result in side effects that worsen other symptoms. Therefore, the treatment goals and plan will be regularly reviewed and updated.

Drugs to treat movement disorders include the following: Tetrabenazine (Xenazine) is specifically approved by the FDA to suppress the involuntary jerking and writhing movements (chorea) associated with Huntington's disease. Other possible side effects include drowsiness, nausea and restlessness. Antipsychotic drugs, such as haloperidol (Haldol®) and chlorpromazine, have a side effect of suppressing movements. Therefore, they may be beneficial in treating chorea. These drugs may, however, worsen involuntary contractions (dystonia) and muscle rigidity. Newer drugs, such as risperidone (Risperdal®) and quetiapine (Seroquel®), may have fewer side effects but still should be used with caution, as they may also worsen symptoms. Other medications that may help suppress chorea include amantadine, levetiracetam (Keppra®) and clonazepam (Klonopin®). At high doses, amantadine can worsen the cognitive effects of Huntington's disease. It may also cause leg swelling and skin discoloration. Side effects of levetiracetam include nausea, stomach upset and mood swings. Clonazepam may worsen the cognitive side effects of Huntington's disease and cause drowsiness. It also has a high risk of dependence and abuse.

In certain embodiments, it will be appreciated that the exact dosage of the biologically active agent (e.g., therapeutic agent) is chosen by the individual physician in view of the patient to be treated, in general, dosage and administration are adjusted to provide an effective amount of the therapeutic agent to the patient being treated. The effective amount of a therapeutic agent refers to the amount necessary to elicit the desired biological response. As will be appreciated by those of ordinary skill in this art, the effective amount of a therapeutic agent may vary depending on such factors as the desired biological endpoint, the drug to be delivered, the target tissue, the route of administration, etc. In certain embodiments, the nanoparticle releases an effective amount of the biologically active agent over a period of at least 10 minutes, 20 minutes, 30 minutes, one hour, two hours, four hours, six hours, ten hours, one day, three days, seven days, ten days, two weeks, one month, or longer. The effective amount of an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. It will be understood, however, that the total daily usage of the therapeutic agents in the delivery system of the present invention will be decided by the attending physician within the scope of sound medical judgment. Such information can then be used to determine useful doses and routes for administration in humans.

J. Pharmaceutical Formulations

Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including but not limited to stereotaxic, sonogram-guided, or other direct injection into the tumor site or around the area of the tumor. The pharmaceutical compositions of the present invention may be prepared for administration by injection to the target area or systemic injection as discussed above. Further, within other embodiments the compounds or compositions provided herein may be admixed with other carriers (e.g., polymers), imaging agents (e.g. via magnetic resonance imaging, optical imaging, positron emission tomography, X-ray computed tomography, and ultrasound imaging) and implanted on or contained within devices which are designed to release such compounds. Within further embodiments, the compounds may be delivered under radioscopic or other visual guidance to a desired site.

Pharmaceutical compositions of the present invention may be placed within containers, or kits, along with packaging material which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

Sterile injectable solutions can be prepared by incorporating the nanoparticle in the required amount in an appropriate solvent with one or a combination of the ingredients known in the art, as required, followed by filter sterilization. These injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In certain embodiments, it will be appreciated that the exact dosage of the Fn14 protein targeted nanoparticle is chosen by the individual physician in view of the patient to be treated. In general, dosage and administration are adjusted to provide an effective amount of the nanoparticle to the patient being treated. As used herein, the "effective amount" of an Fn14 protein-targeted nanoparticle refers to the amount necessary to elicit the desired biological response, in one or more doses, or in a course of treatment consisting of several doses, as is known in the art for treatment of cancer. As will be appreciated by those of ordinary skill in this art, the effective amount of Fn14 protein-targeted particle may vary depending on such factors as the desired biological endpoint, the drug to be delivered, the target tissue, the route of administration, etc. For example, the effective amount of Fn14 protein-targeted particle containing an anti-cancer drug might be the amount that results in a reduction in tumor size by a desired amount over a desired period of time. Additional factors which may be taken into account include the severity of the disease state; age, weight and gender of the patient being treated; diet, time and frequency of administration; drug combinations; reaction sensitivities; and tolerance/response to therapy. The nanoparticles of the invention may be formulated in dosage unit form for ease of administration and uniformity of dosage. In certain embodiments, the Fn14 targeted nanoparticle releases an effective amount of the biologically active agent over a period of at least 10 minutes, 20 minutes, 30 minutes, one hour, two hours, four hours, six hours, ten hours, one day, three days, seven days, ten days, two weeks, one month, or longer. The expression "dosage unit form" as used herein refers to a physically discrete unit of nanoparticle appropriate for the patient to be treated. It will be understood, however, that the total daily usage of the compositions of the present invention will be decided by the attending physician within the scope of sound medical judgement. For any nanoparticle, the therapeutically effective dose can be estimated initially either in cell culture assays or in animal models, usually mice, rabbits, dogs, or pigs. The animal model is also used to achieve a desirable concentration range and route of administration. Such information can then be used to determine effective doses, dose frequencies, and routes for administration in humans, and is well within the skill of the artisan.

Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an exemplary embodiment, a pharmaceutical composition is disclosed that includes a plurality of nanoparticles each comprising a biologically active agent; about 0.1 to about 30 mole percent of the total polymer content, or about 0.1 to about 20 mole percent, or about 0.1 to about 10 mole percent, or about 1 to about 5 mole percent of the total polymer content of a nanoparticle, that is conjugated to Fn14 monoclonal antibody having a molecular weight between about 100 g/mol and 500 g/mol; and a pharmaceutically acceptable excipient. For example, the polymer may have about 0.001 and 5 weight percent of the Fn14 antibody with respect to total polymer content. In some embodiments, a composition suitable for freezing is contemplated, including nanoparticles disclosed herein and a solution suitable for freezing, e.g. a sucrose solution is added to the nanoparticle suspension. The sucrose may e.g., as a cryoprotectant to prevent the particles from aggregating upon freezing. For example, provided herein is a nanoparticle formulation comprising a plurality of disclosed nanoparticles, sucrose and water; wherein the nanoparticles/sucrose/water is about 3-30%/10-30%/50-90% (w/w/w) or about 5-10%/10-15%/80-90% (w/w/w).

K. Methods of Treatment

In some embodiments, targeted structure-specific particulate-based delivery systems in accordance with the present invention may be used to treat, alleviate, ameliorate, relieve, delay onset of, inhibit progression of, reduce severity of and/or reduce incidence of one or more symptoms or features of breast cancer, including metastatic breast cancer, or glioblastoma. The inventive nanoparticles preferably are used to treat solid tumors, metastatic tumors, and individual cancer cells. In certain embodiments, inventive targeted particles may be used to treat any cancer wherein Fn14 is expressed on the surface of cancer cells or in the tumor neovasculature in a subject in need thereof, including brain cancers, breast cancer tumors, breast cancer metastases, and the neovasculature of breast cancer or brain cancer.

In one aspect of the invention, a method for the treatment of a disease or disorder, specifically, cancer (e.g. of the brain, glioblastoma, of the lung, or the breast) is provided. In some embodiments, the treatment of cancer comprises administering a therapeutically effective amount of targeted nanoparticles to a subject in need thereof, in such amounts and for such time as is necessary to achieve the desired result. In one aspect of the invention, a method for administering inventive compositions to a subject suffering from cancer (e.g. glioblastoma or breast cancer) is provided. In some embodiments, particles are administered to a subject in such amounts and for such time as is necessary to achieve the desired result (i.e. treatment of cancer). Inventive therapeutic protocols involve administering a therapeutically effective amount of an inventive targeted particle to a healthy individual (i.e., a subject who does not display any symptoms of cancer and/or who has not been diagnosed with cancer) or a subject who is suspected of suffering from cancer or is susceptible to the cancer. For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, the nanoparticles of the present invention can be used to inhibit the growth of cancer cells, e.g., glioblastoma cells or breast cancer cells. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited. Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

Also provided herein are methods of administering to a patient a nanoparticle disclosed herein including an active agent, wherein, upon administration to a patient, such nanoparticles substantially reduces the volume of distribution and/or substantially reduces free $C_{max}$, as compared to administration of the agent alone (i.e. not as a disclosed nanoparticle).

L. Gene Therapy

Complex genetic mutations are common in brain cancer, making gene therapy an attractive approach to repair or modulate altered genes and cellular pathways. Gene therapy is the administration of a gene encoding a protein of interest as a pharmaceutical agent to treat disease. It derives its name from the idea that a gene can be administered to supplement or alter other genes within an individual's cells as a therapy to treat disease. Scientists first took the logical step of trying to introduce genes directly into human cells, focusing on diseases caused by single-gene defects, such as cystic fibrosis, hemophilia, muscular dystrophy and sickle cell anemia. However, this has proven more difficult than modifying bacteria, primarily because of the problems involved in carrying large sections of DNA and delivering them to the correct site on the comparatively large target genome. Today, most gene therapy studies are aimed at cancer and hereditary diseases linked to a genetic defect. There are a variety of different methods to replace or repair the genes targeted in gene therapy. A normal gene may be inserted into a nonspecific location within the genome to replace a nonfunctional gene. Or an abnormal gene could be swapped for a normal gene through homologous recombination. On the other hand, the abnormal gene could be repaired through selective reverse mutation, which returns the gene to its normal function. The regulation (the degree to which a gene is turned on or off) of a particular gene could be altered.

The most common form of gene therapy involves using DNA that encodes a functional, therapeutic gene in order to replace a mutated gene. Other forms involve directly correcting a mutation, or using DNA that encodes a therapeutic protein drug (rather than a natural human gene) to provide treatment. In gene therapy, the gene is packaged within a "vector," which is used to transfer the gene to the targeted cells within the body. Once inside, the DNA is expressed by the cell machinery, resulting in the production of therapeutic protein, which in turn treats the patient's disease. Gene therapy utilizes the delivery of DNA into cells, which can be accomplished by a number of methods, summarized below.

The majority of current gene therapy-based clinical trials have used viruses to deliver therapeutic DNA. While some viruses can provide safe gene transfer in humans, Phase III clinical trials have failed to show therapeutic efficacy due in part to significant host immune responses, limited therapeutic distribution, and rapid clearance. Non-viral gene vectors can offer DNA delivery without the risk of immunogenicity and/or insertional mutagenesis that are common with viral vectors and have emerged as an alternative to viral strategies. Benefits of non-viral vectors include reduced immunogenicity, ease of manufacturing, lack of risk of vector replication and insertion, and ability to accommodate larger plasmid DNA compared to commonly tested viruses such as adeno-associated viruses. The clinical development of non-viral vectors has been hindered in part by relatively low gene transfer efficiencies compared to viral vectors. This may be due to the inability to overcome various biological barriers. A particularly challenging barrier involves endo-lysosomal trafficking within cells, where therapeutic DNA is often degraded in the acidic and enzyme-rick late-endosomes and lysosomes before reaching the nucleus. A common strategy to overcome this barrier is to incorporate functional groups with acid-base buffering capacity between pH 5.1-7.4, which presumably mediates escape from lower pH endo-lysosomal degradation.

In certain embodiments, the invention comprises highly compacted DNA nanoparticles, composed of 30-mer lysine, conjugated to polyethylene glycol via a single cysteine moiety ($CK_{30}PEG$) and represent a promising non-viral technology that has demonstrated remarkable effectiveness in delivering genes to the brain, eyes and lungs, with minimal toxicity and immunogenicity. These are gene therapy carriers made of polypeptide. The cargo here is either siRNA, miRNA, or plasmid. A pH-responsive DNA nanoparticle, was developed by inserting a poly-L-histidine segment between PEG and poly-L-lysine to engineer a triblock copolymer. In vitro gene transfer efficiency of $CH_{12}K_{18}PEG_5K$ DNA nanoparticles was evaluated in GL261 cells using the reporter plasmid, pRNAT-H1.3/Hygro/siFlu. Highly compacted DNA nanoparticles tested in brain tumor gene delivery studies also showed efficient gene transfer to brain tumor cells in vivo and effectively silenced a tumor-specific transgene (firefly luciferase) following direct injection into mouse intracranial GBM. Simply, $CH_{12}K_{18}PEG_{SK}$ DNA nanoparticles were able to knockdown luciferase in an intracranial GL261 mouse glioma model. These results demonstrate the utility of using this DNA nanoparticle-based technology for delivering genes to tumor cells as a possible therapeutic approach for patients with brain cancer, breast cancer, and other cancers.

It is further contemplated that in other embodiments, any potential non-specific binding of these DNA nanoparticles to the brain or tissue surrounding a tumor, can be minimized by enabling active targeting of Fn14-positive cancer cells by incorporating a targeting moiety onto the highly compacted DNA nanoparticle having the gene construct of interest. Achieving effective distribution of therapies to the complete extent of invasive gliomas and delivering those therapies as directly as possible to the tumor cells, while having minimal bystander effects on adjacent neurons and glia, it a major goal of advanced delivery systems for this disease. Therefore, targeting of therapeutics to tumor cells and/or the close microenvironment represents a critical next step. Previous studies exploring this approach for GBM have included: targeting tumor cell surface molecules such as epidermal growth factor receptor and interleukin 13 receptor, and targeting tumor-associated extracellular matrix components such as Tenascin C21. These targeting moieties have been limited by three major problems: (1) adhesive interactions with non-target structures, (2) targets which are present on only a relatively small percentage of tumor cells or regions, and (3) targets that are not specific to the undesirable invading cells. To address these problems, the DNA nanoparticles can be further developed to be coupled with tumor cell targeting molecules to specifically adhere to the structure(s) of interest.

To deliver the DNA nanoparticle specifically to a particular region and/or to a particular population of cells, the vector may be administered by stereotaxic microinjection or any direct injection into or near the tumor. For example, brain cancer patients have the stereotactic frame base fixed in place (screwed into the skull or other body part). The brain with stereotactic frame base (MRI compatible with fiducial markings) is imaged using high resolution MRI. The MRI images are then transferred to a computer which runs stereotactic software. A series of coronal, sagittal and axial images are used to determine the target (site of nanoparticle injection) and trajectory. The software directly translates the trajectory into 3 dimensional coordinates appropriate for the stereotactic frame. Burr holes are drilled above the entry site and the stereotactic apparatus positioned with the needle implanted at the given depth. The nanoparticle is then injected at the target sites. Since the nanoparticle integrates into the target cells, rather than producing viral particles, the subsequent spread of the vector is minor, and mainly a function of passive diffusion from the site of injection and of course the desired transsynaptic transport, prior to integration. The degree of diffusion may be controlled by adjusting the ratio of vector to fluid carrier.

For breast cancer and metastatic breast cancer patients, nanoparticles preferably are delivered intravascularly.

The target cells of the nanoparticles of the present invention preferably are breast cancer cells, including metastatic breast cancer cells, and also may include glioblastoma cells in brain cancer patients, and cells of the central nervous systems of a subject afflicted a neurodegenerative disease such as Parkinson's disease, Alzheimer's disease, or Huntington's disease, preferably neural cells. Preferably the subject is a human being, generally an adult.

However the invention encompasses delivering the DNA nanoparticle to biological models of the disease. In that case, the biological model may be any mammal at any stage of development at the time of delivery, e.g., embryonic, fetal, infantile, juvenile or adult, preferably it is an adult. Furthermore, the target CNS cells may be essentially from any source, especially nonhuman primates and mammals of the orders Rodenta (mice, rats, rabbit, hamsters), Carnivora (cats, dogs), and Arteriodactyla (cows, pigs, sheep, goats, horses) as well as any other non-human system (e.g. zebrafish model system).

Biodegradable polymeric nanoparticles facilitate nonviral gene transfer to human embryonic stem cells (hESCs). Small (approximately 200 nm), positively charged (approximately 10 mV) particles are formed by the self-assembly of cationic, hydrolytically degradable poly(beta-amino esters) and plasmid DNA.

Some embodiments of the invention relate to an optimized polymer nano-drug formulation to improve therapeutic delivery and efficacy for cancer treatment, with a focus on TNBC. The DART nanoparticle surface characteristics were modified in such a manner that minimized non-specific binding to the blood serum proteins and tumor tissue components, and maintained the Fn14-specific targeting in vivo. The optimized DART formulation provides improved blood circulation time and dispersion, drug distribution, and tumor cell-specific uptake, leading to more effective delivery of PTX in both orthotopic mammary fat pad and brain metastasis TNBC animal models.

Furthermore, optimized PTX-loaded DART nanoparticles exhibited improved therapeutic activity, demonstrated by substantial tumor growth suppression and increased animal survival compared to the FDA-approved PTX nanoformulation Abraxane™. Collectively, these results and methods offer new strategies to engineer therapeutic nano-carriers for improving drug delivery and treatment for primary and metastatic TNBC as well as other solid tumors.

The surface properties of the DART nanoparticles were optimized in order to discover the ideal balance of the ITEM4 surface density and the PEG surface density that achieves an effective Fn14-specific equilibrium binding affinity ($K_D$) so that treatment is efficacious, and a low non-specific binding to blood serum proteins and tumor tissue components to avoid this interference.

Current FDA-approved nanoparticle formulations and other targeted nanoparticles developed for clinical applications have not been shown to significantly improve tumor growth suppression or patient survival for TNBC and other solid tumors. This is likely due to several drug delivery limitations related to selectively targeting tumor cells within the tumor microenvironment, including (i) adhesive interactions with non-target structures, (ii) targets that are present on only a relatively small percentage of tumor cells or regions, (iii) targets that are not specific for TNBC cells, and (iv) target changes in the context of treatment(s) and/or disease progression. The optimized DART formulations with 10% PEG (14.1 PEG molecules/100 $nm^2$) and 1% ITEM4 (0.022 ITEM4 molecules/100 $nm^2$) surface densities (PEG to ITEM4 ratio of 632) displayed prolonged systemic circulation time, indicating that this amount of ITEM4 can be conjugated to the PEG chains without effecting the "stealth" effects normally conferred by a PEG coating. The "stealth" effect of PEG coating on nanoparticles for drug and gene delivery have been widely reported in the literature, including resistance to degradation by nucleases, provide increased colloidal stability, and evade the reticuloendothelial system for long circulation in the bloodstream. Furthermore, eliminating the non-specific binding of nanoparticles by adding a dense PEG coating enables larger than expected particles to rapidly penetrate in various biological environments, including brain tissue and breast tumor tissues.

These particular surface densities above are greatly preferred, but surface densities for PEG in the range of about 1% (3 PEG molecules/100 nm$^2$) to about 20% (30 PEG molecules/100 nm$^2$), preferably about 2.5% to about 15%, and most preferably 5% to about 10%. For ITEM4 of about 0.1% (0.006 ITEM4 molecules/100 nm$^2$) to about 10% (0.075 ITEM4 molecules/100 nm$^2$), preferably about 0.25% to about 5.0%, and most preferably about 0.5% to about 2.0%. In contrast to the inventive DART nanoparticles, Abraxane™ is rapidly cleared from the circulation following systemic administration.

The inventive DART particles retained their Fn14-specific binding after incubation with blood serum incubation. This result is particularly encouraging, since other targeted nanoparticles have been reported to lose their targeting capabilities when place in a biological environment. For example, transferrin receptor-targeted nanoparticles as reported in Salvati et al., Nat, Nanotechnol. 8(2):137-143, 2013. Other nanoparticle formulations with lower surface PEG densities were limited by higher non-specific binding to the blood serum proteins, where the formation of "protein coronas" are believed to initiate rapid RES clearance and/or prevent ITEM4 molecules from efficiently binding to the Fn14 protein due to steric hindrance or related spatial constraints. Id. Similarly, other nanoparticle formulations with 0.1% or 10% ITEM4 density did not bind to Fn14 with sufficient binding affinity or displayed significantly higher accumulation in the spleen, which may be due to particle aggregation or rapid clearance from the blood following systemic administration. These results indicate that achieving the optimal surface properties of DART nanoparticles is likely an important or rate-limiting step for improving nanoparticle-enabled drug delivery for TNBC and other solid tumors.

The beneficial effect of tumor penetration and retention of DART nanoparticles was evident after their direct intratumoral injection into orthotopic mammary fat pad tumors, where they were able to effectively suppress tumor growth. This finding indicated that even if all treatment groups (PLGA-PEG nanoparticles, Fn14-targeted DART nanoparticles, and Abraxane™) are capable of reaching the tumor core and delivering an equivalent dosage of paclitaxel, they will not achieve the same therapeutic effect, due to their tumor penetrative capacities and retention rates. The tumor doubling time for both PLGA-PEG and DART nanoparticle formulations was increased significantly longer than saline, with DART nanoparticles exhibiting the longest time to tumor volume doubling. Abraxane™ did reduce the average tumor volume compared to saline-treated mice; however, the average tumor doubling time for Abraxane™ was not significantly longer than saline. Although the difference in tumor doubling time between DART nanoparticles and Abraxane™ was not statistically significant, this difference may further improve if the dose and administration schedule are modified. We previously reported that Abraxane™ displayed strong non-specific binding to the tumor ECM proteins, suggesting their hindered diffusion in tumor tissues ex vivo and in vivo. Indeed, it has been shown that Abraxane™ does not penetrate tumor tissue following systemic administration. In contrast, the optimized DART nanoparticles displayed rapid tumor penetration in ex vivo breast tumor tissue and minimal non-specific binding to the tumor ECM proteins.

We observed significant therapeutic efficacy of DART nanoparticles following systemic administration in both orthotopic mammary fat pad and in intracranial brain metastasis TNBC tumor models. In the 231-Luc mammary fat pad model, the DART nanoparticles had significantly higher antitumor activity compared to Abraxane™ and PLGA-PEG-IgG nanoparticles used at the equivalent PTX dosage. In addition, DART nanoparticles showed effective antitumor activity on 231-Br-Luc tumors growing in the brain. Similar to the orthotopic tumor model, the PTX-DART nanoparticles outperformed Abraxane™ and PLGA-PEG-IgG-PTX particles. Nanoparticle efficacy in the 231-Br-Luc intracranial model after systemic delivery is consistent with a study demonstrating that 231-Br cell growth within the brain microenvironment promotes blood-brain barrier disruption. While chemotherapy is routinely used to control peripheral metastasis of breast cancer, this modality is largely ineffective at treating metastatic lesions in the brain, due to poor drug penetration and retention at the blood-tumor barrier. The improved therapeutic effects of PTX-DART nanoparticles in both primary and brain metastasis TNBC tumor models are likely due to a combination of prolonged systemic circulation in the blood, enhanced tumor penetration and accumulation at sites of impaired blood-tumor vasculature, and sustained release of paclitaxel from the nanoparticles that reached the tumor site.

One of the potential concerns regarding clinical translation of nanoparticle-based therapies is their eventual accumulation in the liver and spleen and clearance by mononuclear phagocytes. From RBC and WBC counts and the liver and kidney toxicity analyses, the DART nanoparticles did not produce any detectable adverse effects when given systemically as a single dose of 10 mg/kg PTX. In addition, the liver and spleen of the mice treated with DART nanoparticles did not show significant tissue damage or increase in immune cell infiltration, compared to the controls. No significant reduction in the weight of tumor-bearing mice was observed following the treatment, suggesting minimal systemic toxicity from nanoparticle administrations. Although potential toxicity associated with multiple dosing of DART nanoparticles was not tested because since PLGA-based polymers are biodegradable and have a long track-record of safety, the systemic toxicity of DART nanoparticles should be tolerable even with multiple injections.

The TNFR family member, Fn14, was chosen as the cancer cell target for the present series of experiments regarding breast cancer. Fn14 is not expressed in normal breast tissue but is highly expressed in TNBC primary tumors and in disseminated breast cancer metastases. Fn14 undergoes constitutive receptor internalization and resynthesis, which can facilitate efficient cellular uptake of Fn14-targeted therapeutics. In addition, Fn14-targeted cytotoxic agents can overcome the drug resistance noted in cell lines that overexpress multidrug resistance pumps. Using a brief drug exposure paradigm, the optimized PTX-DART nanoparticles induced significantly enhanced cytotoxicity on 231-Luc cells, compared to free PTX, Abraxane™, and non-targeted PLGA-PEG nanoparticles, which is likely due to the increased Fn14 receptor-mediated binding and cellular uptake of PTX-DART nanoparticles. When ITEM4, an Fn14 targeting moiety, is added to cancer cells it is rapidly internalized, a process that is required for effective drug delivery by targeted nanotherapeutics. Fn14 can serve as a more robust target than other cell surface molecules previously tested for targeted nanoparticle delivery for TNBC (e.g., uPAR; folate receptor; EGFR; CD44; integrin αvβ3). The successful development of effective PTX-DART nanoparticle therapeutics for TNBC should be extended to treatment of numerous other Fn14-positive tumor types, including lung, pancreatic, prostate, ovarian, and brain cancers.

Preferred drug delivery nanoparticles for treatment of breast cancer and metastatic breast cancer comprise a) a nanoparticle having a hydrodynamic diameter of about 4 nm to about 200 nm or about 20 nm to about 200 nm or about 100 nm;

b) a coating of polyethylene glycol with a surface density of at least 3 polyethylene glycol molecules per 100 nm$^2$;

c) an Fn14 targeting moiety that specifically binds to the cell surface of a breast cancer cell or metastatic breast cancer cell, where the surface density of the Fn14 targeting moiety is about 0.5% to about 15%, or about 0.1% to about 10%, or about 1% to about 10%, or about 2% to about 8%; and d) a therapeutic agent.

5. EXAMPLES

The invention is illustrated herein by the experiments described by the following examples, which should not be construed as limiting. This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

In this study, we examined if (1) Fn14 could be used as a portal for TNBC nanotherapeutic delivery, (2) surface properties of DARTs could be engineered to optimize Fn14 receptor-mediated interaction while minimizing non-specific binding to blood serum proteins and tumor tissue components, and (3) PTX-loaded DART nanoparticles provided enhanced therapeutic effects compared to non-targeted nanoparticles, including Abraxane™. We formulated PTX-loaded DART nanoparticles using biodegradable poly(lactic-co-glycolic acid)-poly(ethylene glycol) (PLGA-PEG) polymers and conjugated an Fn14 monoclonal antibody to specifically target Fn14-positive TNBC cells. We assessed the physicochemical characteristics and optimized the DART surface properties using multiple particle tracking (MPT), confocal microscopy, surface plasmon resonance (SPR) binding analyses, and in vivo imaging. Finally, the therapeutic efficacy and safety of DART nanoparticles was evaluated in orthotopic mammary fat pad and brain metastasis models of TNBC.

Example 1: Materials and Methods

A. Materials

Five kDa MW PEG, methoxy-PEG5k-amine and thiol reactive malemide-PEG5k-amine, were purchased from Creative PEGWorks™ (Winston Salem, N.C.). Lab-Tek™ glass-bottom tissue culture plates and Zeba™ Spin Columns (7 kDa MW cut-off) were purchased from ThermoFisher Scientific™. ITEM4 monoclonal antibody was purchased from eBioscience™ (San Diego, Calif.). Red (0.1 μm, 540/590 excitation/emission) and Blue (0.1 μm, 350/440 excitation/emission) carboxylate-modified FluoSpheres™ and Hoechst™ 34580 were purchased from Invitrogen™ (Carlsbad, Calif.). Non-fluorescent carboxyl microspheres (0.1 μm) were purchased from Bang's Laboratories™ (Fishers, Ind.). D-Luciferin was obtained from Promega™ (Madison, Wis.). Thiol Quantification Assay Kit (Fluorometric™) was from Abeam™ (Cambridge, Mass.). 1-Ethyl-3-[3-dimethylaminopropyl]carbodiimide hydrochloride (EDC), N-hydroxysulfosuccinimide (sulfo-NHS), Phosphate Buffer, 2-iminothilane hydrochloride, and all other chemicals were purchased from Sigma-Aldrich™ (St. Louis, Mo.).

Methoxy terminated poly(lactic-co-glycolic acid)-polyethylene glycol (PLGA-PEG, 10:5 kDa), PLGA-PEG with maleimide end group (PLGA-PEG-Mal, 10:5 kDa), and PLGA-rhodamine B (PLGA-Rhod, 10:30 kDa) were purchased from Polyscitech™. Poly vinyl alcohol (PVA, 25 kDa) was purchased from Polysciences™. 5 kDa MW polyethylene glycol (PEG), methoxy-PEG5k-amine and thiol reactive malemided-PEG5k-amine were purchased from Creative PEGWorks™. Near infrared 40 nm carboxyl (COOH)-modified PS FluoSpheres (PS-COOH) were purchased from Invitrogen™. Paclitaxel (>99.5%) (PTX was purchased from LC Laboratories™. Clinical-grade Abraxane™ was purchased from the University of Maryland Medical Center Outpatient Pharmacy. The ITEM4 mAb was provided by Dr. Hideo Yagita (Juntendo University School of Medicine, Tokyo, Japan). Lab-Tek™ glass-bottom tissue culture plates and Zeba™ Spin Columns (7 kDa cut-off) were purchased from ThermoFisher™ Scientific. The ITEM4 scFv protein was provided by Dr. Michael Rosenblum (University of Texas MD Anderson Cancer Center). The thiol-modified Fn14 ligand peptide sequence was custom synthesized by GenScript™ Inc. The mouse IgG isotype control antibody and Hoechst™ 33342 trihydrochloride were purchased from Invitrogen™. D-Luciferin was purchased from Promega™. Matrigel™ basement membrane matrix was purchased from BD Biosciences™. Cell culture materials, including Dulbecco's modified Eagles's medium (DMEM), 0.25% trypsin, fetal bovine serum and penicillin-streptomycin, were purchased from Corning™. All Biacore™ materials, including sensor chips and running buffers, were purchased from GE Healthcare Life Sciences™. PLGA (7-17 kDa, 50:50), dichloromethane (DCM), chloroform-d (CDC13), phosphate buffer solution (PBS), 2-iminothiolane hydrochloride, and all other chemicals were purchased from Sigma-Aldrich™ and used without further purification.

B. Preparation of Thiol-Modified Target Molecules

ITEM4 was thiol-modified via reaction of free amines with 2-iminothiolane. Briefly, ITEM4 (0.5 mg/mL) was mixed with 2-iminothiolane (400× molar excess to ITEM4) in 100 mM phosphate buffer with EDTA (pH 7.2, 150 mM NaCl, 5 mM EDTA) in a siliconized tube. The reaction was allowed to proceed for 2 hours at room temperature to yield thiolated ITEM4 (ITEM4-SH). After the reaction, resulting solution was purified with Zeba™ Spin Columns (7 kDa MW cutoff) and frozen immediately to avoid potential disulfide bond formation (S—S) between newly generated thiol groups. The degree of thiolation of ITEM 4-SH was determined using the Thiol Quantification Assay Kit (Fluorometric assay, Abeam™, Cambridge, Mass.) as per the manufacturer's recommendations. Gluathione (GSH) standard was used to generate a standard curve to determine the number of thiol groups per ITEM4.

In other cases, the Fab portion of the ITEM mAb were prepared using Fab fragmentation kit (ThermoFisher Scientific™) following manufacturer's instructions. Then the IgG, ITEM mAb, ITEM4 Fab and ITEM4 scFv were thiol-modified via reaction of free amines with 2-iminothiolane as described. Briefly, the targeting moieties were mixed with 2-iminothiolane (140× molar excess) in 100 mM phosphate buffer with EDTA (pH 7.2, 150 mM NaCl, 5 mM EDTA). The reaction was allowed to proceed for 2 hours at room temperature to yield thiolated targeting moieties. After the reaction, the resulting solution was purified with Zeba™ Spin Columns (7 kDa MW cut-off) and frozen immediately to avoid potential disulfide bond formation between newly generated thiol groups.

C. Nanoparticle Preparation

The detailed methods below are the main formulation methods used for generation of tissue penetrating nanoparticles (TPN). However, there are a wide variety of formulation methods, polymers, ligands, and chemistries that can be used to achieve targeted, tissue penetrating nanoparticles as described in U.S. Patent Application No. 2013/0183244A.

1. Non-Biodegradable Nanoparticles

Nanoparticles were synthesized from COOH-modified polystyrene (PS) NP (PS-COOH). First, PS-COOH nanoparticles were added to a siliconized microcentrifuge tube (Sigma™) and completed to a volume of 500 µL with phosphate buffer (50 mM NaCl, 100 mM Na(PO3)4, pH 7.2). PEG (a mixture of NHrPEGsk-OCH3 and NHr PEGsk-maleimide or of NHrPEG5k-OCH3 and NHrPEG5k-N3) was dissolved directly (10× equivalent to COOH groups on surface of PS-COOH spheres), followed by excess sulfo-NHS (~5-6 mg), and excess EDC (~3-4 mg). The reaction was allowed to proceed for 4 hours at 25° C. Nanoparticles were purified by ultracentrifugation through a 100 kDa AmiconUltra 15 mL ultrafiltration device (Millipore™) and washing with 15 ml of ultrapure water (3 washes total).

Maleimide-thiol or N3-alkyne chemistry was performed to conjugate a thiol-modified or alkyne-modified ligand to the surface of the nanoparticle. Briefly, purified nanoparticles were mixed with modified ligand in phosphate buffer and allowed to react overnight under stirring at 4° C. Nanoparticles were purified from unreacted ligand via dialysis over 5 days using Float-a-Lyzer™ dialysis cassettes (1000 kDa MWCO, Spectrum™ Labs).

2. Biodegradable Polymers

The methods described below are ones using one polymer (poly(lactic-co-glycolic acid; PLGA). This method can be used to generate ligand modified, brain penetrating particles with a variety of different hydrophobic polymers (e.g. other polyesters such as poly(lactic acid), polycaprolactone, as well as polyanhydrides and many others). Further, in certain embodiments, several other standard hydrophobic particle formulation techniques (e.g. single emulsion, double emulsion, salting-out, etc.) can be used. The ligand used could be a small molecule, antibody, antibody fragment, protein, nucleic acid, etc. The coupling chemistry between the particle/polymer and ligand can also be modified as needed based on the ligand.

In some embodiments, synthesis of empty, rhodamine-labeled, maleimide-terminated, or PTX-loaded PLGA-PEG biodegradable PLGA-based nanoparticles was achieved using a single emulsion solvent evaporation technique. Briefly, the polymers and drugs were dissolved in 2 mL DCM to form organic/oil phase. PVA (5% w/v) was dissolved in water and passed through a 0.2 µm filter to form a water phase. The oil phase was added to 12 mL of the water phase to form an oil-in-water emulsion. All the emulsions were sonicated in an ice bath using ultrasonication probe at 30% amplitude for 3 minutes with the 20 second on-off pulser. The sonicated emulsions were immediately transferred to magnetic stirring for 4 hours at room temperature to evaporate the organic solvent. The formed nanoparticles were washed by microcentrifugation at 21,100×g for 10 minutes with ultrapure water (4 washes total). The nanoparticles were resuspended in ultrapure water and used fresh for experiments. In addition, adhesive PLGA nanoparticles were formulated following the same method, but using TWEEN 20 (2% w/v) surfactants instead of PVA.

3. Direct Conjugation to Polymer Prior to Particle Formulation (for Organic Solvent Soluble and Stable Ligands)

PLGA, PLGA-PEG, and PLGA-PEG-ligand were dissolved at 25 mg/mL in tetrahydrofuran (THF), along with a quantity of drug/therapeutic. Nanoparticles were formed by nanoprecipitation upon the addition of the THF solutions to stirred ultrapure water (or appropriate buffer to ensure ligand stability). Solvent (THF) was allowed to evaporate under stirring for two hours and nanoparticles were subsequently concentrated and washed three times with UP water via ultrafiltration with 100 kDa centrifugal filter units (Millipore™).

4. Conjugation of Ligand to Particles after Particle Formulation (for Ligands that are not Soluble or Stable in Organic Solvents)

PLGA, PLGA-PEG, and PLGA-PEG-maleimide (or PLGA-PEG-azide) were dissolved at 25 mg/mL in tetrahydrofuran (THF), along with a quantity of drug/therapeutic. Nanoparticles were formed by nanoprecipitation upon the addition of the THF solutions to stirred ultrapure water (or appropriate buffer to ensure ligand stability). Solvent (THF) was allowed to evaporate under stirring for two hours and nanoparticles were subsequently concentrated and washed three times with UP water via ultrafiltration with 100 kDa centrifugal filter units (Millipore™).

Maleimide-thiol or N3-alkyne chemistry was performed to conjugate a thiol-modified or alkyne-modified ligand to the surface of the NP. Briefly, purified NP are mixed with modified ligand in phosphate buffer and allowed to react overnight under stirring at 4° C. Nanoparticles were purified from unreacted ligand via dialysis over 5 days using Float-a-Lyzer™ dialysis cassettes (1000 kDa MWCO, Spectrum Labs™)

5. Antibody Conjugation to PLGA-PEG Nanoparticles

To formulate targeted PLGA-PEG nanoparticles, IgG-SH, ITEM4 mAb-SH, ITEM4 Fab-SH, ITEM4 scFv-SH, or thiolated Fn14 peptide was conjugated onto the surface of PLGA-PEG nanoparticles containing maleimide functional groups (PLGA-PEG-Mal) by maleimide-thiol chemistry as described previously. Briefly, PLGA-PEG-Mal nanoparticles were mixed with thiol-modified targeting moieties (1.2× excess SH to maleimide) in 100 mM phosphate buffer (pH 7.2, 150 mM NaCl) and allowed to react overnight at 4° C. This reaction was performed immediately following PLGA-PEG-Mal formulation to avoid hydrolysis of the maleimide groups due to longer incubation times. After the reaction, targeted nanoparticles were purified from unconjugated free targeting moieties via microcentrifugation at 21,100×g for 10 minutes with ultrapure water (3 washes total). The nanoparticles were resuspended in ultrapure water and used fresh for experiments.

For IgG- and ITEM4-conjugated PS-PEG nanoparticles, a different proportion of PEG (10% methoxy-PEG5k-amine to 1% malemide-PEG5k-amine) was used for particle PEGylation. IgG-SH or ITEM4-SH was conjugated onto the surface of the nanoparticles containing maleimide-functionalized PEG by maleimide-thiol chemistry. Briefly, purified PS-PEG-Mal nanoparticles were mixed with IgG-SH or ITEM4-SH in 100 mM phosphate buffer (pH 7.2, 150 mM NaCl) and allowed to react overnight at 4° C. This reaction was performed immediately following nanoparticle PEGylation, as longer incubation times result in increased hydrolysis of the maleimide groups. After the reaction, nanoparticles were purified from free IgG-SH or ITEM4-SH via dialysis (1000 kDa Float-a-Lyzer™ dialysis cassettes) against 1×PBS for 3 days.

5. Details Concerning Targeted, Biodegradable TPNs-Hydrophilic Polymers Via Chelation The detailed method below uses one specific polymer (PGA) and one specific chelating agent/drug (cisplatin or CDDP). This method can be used to generate ligand modified, brain penetrating particles with a variety of different hydrophilic polymers with a high density of carboxyl acid side chains (e.g. hyaluronic acid and polyaspartic acid).

Polymer stock solutions were created by dissolving polymers in nuclease-free water (PGA, PGA-PEG, and PGA-PEG-azide). Nanoparticles were made by mixing an equal volume of polymer stock solutions with cisplatin (CDDP), or other chelating drug/molecule, stock solution (1.5 mg/ml CDDP in nuclease free water). After mixing, particles were allowed to self-assemble for 3+ days under continuous stirring at 45° C. After particle formation, particles were washed three times in ultrapure water and concentrated by ultrafiltration with 100 kDa centrifugal filters (Amicon® Ultra, Millipore™)

N3-alkyne chemistry was performed to conjugate an alkyne-modified ligand to the surface of the nanoparticle. Purified nanoparticles were mixed with modified ligand in dilute phosphate buffer and allowed to react overnight under stirring at 4° C. Nanoparticles were purified from unreacted ligand via dialysis over 5 days using Float-a-Lyzer™ dialysis cassettes (1000 kDa MWCO, Spectrum Labs™).

6. Detailed Formulation of Targeted, Lipid- and Amphiphilic Block Copolymer-Based TPNs The detailed method below uses one specific phospholipid (DSPE) and one specific diblock copolymer (PBD-PEO). This method can be used to generate ligand modified, brain penetrating particles with a variety of different lipids or amphiphilic block copolymers. Further, several other standard drug encapsulation techniques (e.g., pH gradient, hydration, etc.) can be used to encapsulate different drugs/therapeutics. The ligand used could be a small molecule, antibody, antibody fragment, protein, nucleic acid, etc. The coupling chemistry between the particle/polymer and ligand can also be modified as needed based on the ligand.

a. Liposome-Based Formulation 1,2-distearoyl-sn-glycero-3-phosphoethanolamine (DSPE) lipid was blended with DSPE-polyethylene glycol (DSPE-PEG-malemide or DSPE-PEG-azide; 5-10 wt %) in methylene chloride. Liposomes were formed by hydration/sonication in IX PBS along with a quantity of drug/therapeutic at 65° C. for 1 hour. A narrow size distribution of nanosized polymersomes was achieved with serial extrusion using a Liposofast™ Basic hand-held extruder equipped with 400, 200, 100, and 50 nm polycarbonate membranes (Avestin™ Inc., Ottawa, Ontario).

Maleimide-thiol or N3-alkyne chemistry was performed to conjugate a thiol-modified or alkyne-modified ligand to the surface of the liposomes. Purified liposomes were mixed with modified ligand in phosphate buffer and allowed to react overnight under stirring at 4° C. Liposomes were purified from unreacted ligand via dialysis over 5 days using Float-a-Lyzer™ dialysis cassettes (1000 kDa MWCO, Spectrum Labs™)

b. Polymersome-Based Formulation

The PEO terminal hydroxyl end of the copolymer (PEO-b-PBD (PEO=polyethyleneoxide; PBD=polybutadiene); Polymer Source™, Inc., Montreal, Quebec) was first modified with 4-fluoro-3-nitrobenzoic acid, succinimidyl carbonate, or carboxylic acid through an esterification procedure. The activated polymer was then precipitated using diethyl ether and purified using high performance liquid chromatography (HPLC). Targeting ligands were attached to the modified polymer through a nucleophilic aromatic substitution and/or via EDC/NHS reaction. Nonconjugated Tat was removed following polymersome formation by extensive dialysis in isotonic phosphate buffered saline (PBS), pH 7.4.

The selected polymer and drug/therapeutic (hydrophobic) were dissolved in methylene chloride and then deposited onto a roughened Teflon™ square and dried overnight under vacuum. IX PBS along with a quantity of drug/therapeutic (hydrophilic) was then added to a glass vial containing the film; the vial was then sealed and allowed to sonicate at 65° C. for 1 hour. A narrow size distribution of nanosized polymersomes was achieved with serial extrusion using a Liposofast™ Basic hand-held extruder equipped with 400, 200, 100, and 50 nm polycarbonate membranes (Avestin™ Inc., Ottawa, Ontario).

To formulate brain tissue penetrating 'coated nanoparticles' (CNPs), 100 nm carboxylate-modified polystyrene (PS-COOH) nanoparticles were covalently modified with methoxy-PEG5k-amine by EDC carbodiimide chemistry, following a modified protocol described previously. For a protein quantification assay, CNPs were made with 100 nm non-fluorescent PS-COOH nanoparticles. For all other experiments, 100 nm red or blue fluorescent PS-COOH 'uncoated nanoparticles' (UNP) were used. Briefly, PS-COOH nanoparticles (1 mg) were mixed with methoxy-PEG5k-amine (10× equivalent to total COOH groups on surface of PS-COOH particles) in 100 mM phosphate buffer (pH 7.2, 150 mM NaCl), followed by addition of excess sulfo-NHS (~5-6 mg), and EDC (~3-4 mg) to a volume of 500 μL. Particle suspensions were placed on a rotary incubator and the reaction was allowed to proceed for 4 hours at 25° C. After the reaction, particles were purified by ultracentrifugation (Amicon Ultra™ 15 mL 100 kDa MW cutoff) with ultrapure water (3 washes total). CNPs were resuspended in ultrapure water and stored at 4° C. until use.

For CNP-ITEM4 nanoparticles, a different proportion of PEG (methoxy-PEG5k-amine to malemide-PEG5k-amine) was used for initial particle PEGylation. Specifically, 10 mol % and 50 mol % of maleimide-PEG5k-amine was used for CNP-rfEM4 (low) and CNP-rfEM4 (high) nanoparticles, respectively. ITEM4-SH was conjugated onto the surface of the nanoparticles containing maleimide-functionalized PEG by maleimide-thiol chemistry. Briefly, purified CNP-maleimide particles were mixed with ITEM4-SH (1.2× excess ITEM4-SH to maleimide) in 100 mM phosphate buffer (pH 7.2, 150 mM NaCl) and allowed to react overnight at 4° C. This reaction was performed immediately following nanoparticle PEGylation, as longer incubation times resulted in increased hydrolysis of the maleimide groups. After the reaction, nanoparticles were purified from unconjugated free ITEM4-SH via dialysis (1000 kDa Float-a-Lyzer™ dialysis cassettes) against IX PBS for 5 days. The amount of ITEM4 molecules conjugated on CNP-ITEM4 nanoparticles was quantitated via the LavaPep™ protein assay (Gel Company™ San Francisco, Calif.) using ITEM4 as a standard. Nanoparticle samples were diluted to a concentration of 100 μg/mL and assayed as per the manufacturer's protocol.

7. PEGylation of PS Nanoparticles

PEG-coated PS nanoparticles were formulated as follows. Briefly, 1 mg PS-COOH was mixed with methoxy-PEG5k-amine (10× equivalent to total COOH groups on surface of PS-COOH particles) in 100 mM phosphate buffer (pH 7.2, 150 mM NaCl), followed by addition of excess sulfo-NHS (~5-6 mg) and EDC (~3-4 mg) to a volume of 500 μL. Particle suspensions were placed on a rotary incubator and the reaction was allowed to proceed for 4 hours at 25° C. After the reaction, particles were purified by ultracentrifugation (Amicon™ Ultra-15 mL 100 kDa MW cut-off) with ultrapure water (3 washes total). Nanoparticles were resuspended in ultrapure water and stored at 4° C. until use.

8. PEG Density Measurements

The PEG density on nanoparticle surface (# of PEG chains/100 nm$^2$) and $\Gamma/\Gamma^*$, where $\Gamma$ is the PEG surface coverage over the total surface area ($\Gamma^*$), were calculated from the 1H integrals of the ethylene oxide peak of PEG using known methods. Briefly, nanoparticles were lyophilized, weighed and dissolved in CDCl3 containing 0.1% (v/v) trimethylsilane as an internal standard. Nuclear magnetic resonance (NMR) spectra were obtained at 500 MHz using Agilent™ DD2 500 MHz Spectrometer. A calibration curve was obtained by plotting the 1H NMR integrals of various concentrations of 5 kDa PEG (~3.6 ppm) in CDCl3 solvent containing 0.1% (v/v) trimethylsilane. The average PEG density (# of PEG chains/100 nm$^2$) on the nanoparticle surface was calculated by taking the total quantity of PEG detected by NMR and the total nanoparticle surface area. The nanoparticle surface area was calculated assuming that the particles are made of individual particles of diameter equal to that measured by the Zetasizer™ and using PLGA density of 1.34 g/cm$^3$.

9. Antibody Density Measurements

The density of ITEM4 or IgG on nanoparticle surface (# of ITEM4 or IgG molecules/particle) was quantitated via the LavaPep™ protein assay (Gel Company™). A calibration curve was generated by plotting the fluorescence from different concentrations of free antibody molecules. The average surface density of antibodies on the nanoparticle surface was calculated by taking the total quantity of ITEM4 or IgG measured by the LavaPep™ protein assay and the total number of nanoparticles in 1 mL solution. The number of nanoparticles in the sample was calculated assuming that the nanoparticles are made of individual nanoparticles of diameter equal to that measured by the Zetasizer™ and using PLGA density of 1.34 g/cm$^3$.

D. Physicochemical Characterization of Nanoparticles

The physicochemical characteristics of nanoparticles were measured in 15× diluted PBS (~10 mM NaCl, pH 7.4) at 25° C. Hydrodynamic diameter and -potential (surface charge) were determined by dynamic light scattering and laser Doppler anemometry, respectively, using a Zetasizer™ NanoZS™ (Malvern Instruments™). Particle size measurement was performed at 25° C. at a scattering angle of 173° and is reported as the number-average mean. The zeta-potential values were calculated using the Smoluchowski equation and is reported as the mean zeta-potential. Nanoparticle structure and morphology was assessed using FEI Tecnai™ T12 TEM (FEI™) operated at 80 kV.

E. Determination of PTX Loading in Nanoparticles

For PTX loading measurements, lyophilized nanoparticles were dissolved in acetonitrile (1 mg/mL) and passed through 0.2 μm filter to separate drugs from polymers. The filtered solution was analyzed at UV absorption peak of 228 nm on high performance liquid chromatography (HPLC, Waters™, 2690) equipped with a reverse phase C18 column (150 mm×4.6 mm, Supelco™). The pump was set for isocratic flow with mobile phase A (0.4 mL/min) consisting of acetonitrile/DI water/trifluoroacetic acid (2/98/0.05, v/v/v) and mobile phase B (0.6 ml/min) consisting of acetonitrile/DI water/trifluoroacetic acid (99/1/0.05, v/v/v). The PTX retention time was found to be 7 minutes. A PTX standard curve was established by plotting peak areas with respect to known PTX concentrations. The drug loading (DL) % was calculated from following equation:

DL (%)=(Weight of PTX in the NPs/Total weight of NPs)×100.

F. Determination of PTX Release from Nanoparticles

In vitro release of PTX from nanoparticles was performed using the dialysis method over 28 days. A known amount of nanoparticles in PBS (pH 7.4, 1 ml) was placed in Float-A-Lyzer™ dialysis tubes (3.5-5 kDa cut-off, Spectrum Labs™) and dialyzed against PBS on an orbital shaker at 37° C. At predetermined time intervals, 1 mL dialysate was collected and an equal volume was replenished with fresh PBS incubated at 37° C. All the collected PTX release samples were analyzed by HPLC with the setting mentioned above to get the PTX peak areas. The drug release (DR) % was calculated from following equation:

DR (%)=Amount of drug in dialysate×100/Amount of drug in NP in dialysis tube.

G. Flow Cytometry

Fn14 expression analysis by flow cytometry. To examine Fn14 surface expression by 231-Luc and 231-Br-Luc cell lines, flow cytometry analysis was performed. Briefly, cells were seeded in 24-well plates at a density of 10$^5$ cells per well and allowed to attach overnight. The media then was replaced with serum-free DMEM along with no antibody, IgG-PE, or ITEM4-PE. After 1 hour incubation, cells were washed 3 times with PBS, detached with trypsin, and diluted in cold PBS for flow cytometry analysis. Mean fluorescence intensity was analyzed using a FACSCalibur™ flow cytometer (Becton Dickinson™). Data from 104 events were gated using forward and side scatter parameters to exclude dying cells and debris.

Nanoparticle cellular association analysis by flow cytometry. Cellular association of rhodamine-labeled nanoparticles with Fn14-positive 231-Luc cells was determined by flow cytometry. Briefly, cells were seeded in 24-well plates at a density of 10$^5$ cells/well and allowed to attach overnight. The media was then replaced with serum-free DMEM containing nanoparticles (100 μg per well). In addition, to confirm the specific interaction between ITEM4 and Fn14, the cells were incubated with free ITEM4 (500 μg/ml) for 30 minutes to block Fn14 binding sites before adding Fn14-targeted PLGA-PEG-ITEM4. After 1 hour incubation, cells were washed 3 times with PBS, detached with trypsin, and diluted in cold PBS. Mean fluorescence intensity was analyzed using a FACSCalibur™ flow cytometer.

H. Nanoparticle Binding to Fn14 Extracellular Domain

Nanoparticle binding affinities to Fn14 extracellular domain was evaluated by SPR using a Biacore™ 3000 instrument at 25° C. The Fn14 extracellular domain (Cell Sciences™, Canton, Mass.) was conjugated to a CM5 Biacore™ chip, with three different Fn14 ligand RU values ranging from 50 to 300. The first flow path (Fc1) was activated and blocked with ethanolamine to serve as a reference for each binding run, as suggested per manufacturer's protocol. The running buffer was degassed 10 mM HEPES buffer (pH 7.4) containing 150 mM NaCl, 0.05% surfactant P-20 with 50 μM EDTA (HBS-P+). For surface plasmon resonance (SPR) experiments, samples were run at a flow rate of 20 μL/min with an injection time of 3 minutes followed by a 2.5 minute wait time for dissociation, before chip regeneration with either 100 mM phosphoric acid, pH 3 or 10 mM glycine, pH 1.75 (GE Healthcare™). IgG isotype (25 nM) was used as a negative control and ITEM4 (25 nM) as a positive control. Nanoparticle binding was assayed with particle concentrations ranging between 1 μg/mL and 200 μg/mL diluted in running buffer. Data were analyzed using Biacore™ 3000 Evaluation Software, where data from Fc1 was subtracted from the Fc2, Fc3, and Fc4 data to give the final sensorgrams. Equilibrium binding affinities ($K_D$) were calculated as previously described.

I. Nanoparticle Binding to Brain Extracellular Matrix Proteins

Brain extracellular matrix (ECM) proteins were isolated from freshly collected mouse brain as previously described. Briefly, resected whole mouse brain was frozen for at least 24 hours at −80° C. and subsequently thawed and decellularized in a series of steps: ultrapure water (16 hours at 4° C.), 0.02% trypsin/0.05% EDTA (1 hour at 37° C.), 3% Triton-X 100 (1 h), 1.0 M sucrose (15 minutes), ultrapure water (15 minutes), 4% deoxycholate (1 hour), 0.1% periacetic acid in 4% ethanol (2 hours), IX PBS (15 minutes), ultrapure water (15 minutes), and IX PBS (15 minutes). The decellularized proteins were filtered (0.2 μm filter) to remove insoluble proteins and then frozen and stored at −80° C. until use.

The isolated mouse brain ECM proteins were conjugated to the second flow channel (Fc2) of a CMS Biacore™ chip with ligand RU values ranging from 140 to 250. The first flow path was activated and blocked with ethanolamine to serve as a reference for each binding run. For binding experiments, samples were assayed at a flow rate of 20 μL/min with an injection time of 3 minutes followed by a 2.5 minute wait time for dissociation, before chip regeneration with either 100 mM phosphoric acid, pH 3 or 10 mM glycine, pH 1.75 (GE Healthcare™) Nanoparticle binding was assayed with particle concentrations ranging between 1 μg/mL and 200 μg/mL, diluted in running buffer.

J. Non-Specific and Fn14-Specific Binding Analysis of Nanoparticles

Non-specific binding of nanoparticles was analyzed on a tumor ECM preparation (Matrigel™), whereas Fn14-specific binding of nanoparticles was analyzed on recombinant Fn14 extracellular domain (Cell Sciences™) using a high throughput SPR-based Biacore™ 3000 instrument (GE Healthcare™) at 25° C. Matrigel™ or Fn14 extracellular domain was diluted in acetate buffer (pH 4.0) and conjugated to a CMS Biacore™ chip with response units (RU) value of approximately 5000 and approximately 1700, respectively. The first flow path (Fc1) was activated and blocked with ethanolamine to serve as a reference for each binding run, as suggested per manufacturer's protocol. The running buffer, 10 mM HEPES buffer (pH 7.4) containing 150 mM NaCl and 50 μM EDTA (HBS-N), was degassed prior to use. For binding experiments, free antibody or nanoparticle samples were assayed at a flow rate of 20 μL/min with an injection time of 3 minutes followed by a 2.5 minute wait for dissociation, before chip regeneration with 10 mM glycine (pH 1.75).

Nanoparticle binding was assayed at concentrations of 1 mg/ml diluted in running buffer. Data were analyzed using Biacore™ 3000 Evaluation Software, where data from Fc1 were subtracted from the Fc2, Fc3, and Fc4 data to give the final sensorgrams. In addition, binding isotherms for the nanoparticle were generated by analyzing kinetic binding of nanoparticles to the Fn14 chip at serially diluted nanoparticle concentrations. The data were analyzed by fitting to a pseudo-first order process to determine the maximum change in response units (RUeq). RUeq values were then plotted versus nanoparticle concentrations and the equilibrium binding affinities (KD) were calculated by fitting the binding isotherm data into a single class of binding sites using non-linear regression analysis employing GraphPad™ Prism 7.03 software (GraphPad™ Software Inc.).

K. Cell Culture

Human U87 glioblastoma cells that constitutively express firefly luciferase (U87-Luc) were provided by Dr. Andrew Kung (Columbia University Medical Center). In order to generate a GFP-positive U87-Luc cell line, pGIPZ lentiviral particles encoding TurboGFP (provided by Dr. Nhan Tran, TGen) were mixed with 8 μg/mL polybrene and added to subconfluent cultures of U87-Luc cells. Positively transduced cells were enriched by mass sorting the GFP-positive cells using a MoFlo™ flow cytometer (Dako™). U87-Luc/GFP cells were cultured at 37° C. and 5% $CO_2$ in DMEM (Invitrogen™ Corp., Carlsbad, Calif.) supplemented with 10% fetal bovine serum (FBS, Invitrogen™ Corp.), 0.5 mg/mL G418, and 1% penicillin/streptomycin (Invitrogen™ Corp.). A mouse embryonic fibroblast (MEF) cell line generated from Fn14-null mice (MEF 3.5−/−) and a derivative stably transfected MEF 3.5−/− cell line expressing human Fn14 (MEF Fn14-V5) were provided by Dr. Matthew Hayden (Columbia University Medical Center). Both cell lines were maintained at 37° C. and 5% $CO_2$ in DMEM supplemented with 10% FBS and 1% penicillin/streptomycin; the Fn14-V5 cell media also contained 10 ug/ml blasticidin.

The 231-Luc cell line was provided by Dr. Stuart Martin (University of Maryland School of Medicine, Baltimore, Md.). The 231-Br-Luc "brain seeking" cell line was provided by Dr. Suyun Huang (University of Texas MD Anderson Cancer Center, Houston, Tex.). This is a brain-seeking clone of the parental cell line MDA-MB-231 that was established to study breast cancer metastasis to the brain as previously described. The cell lines were cultured at 37° C. in a humidified incubator (95% air, 5% $CO_2$) in DMEM supplemented with 10% fetal bovine serum and 1% penicillin-streptomycin (1000 units/1). The culture media for 231-Luc and 231-Br-Luc cells was additionally supplemented with 0.25 mg/ml G418 sulfate and 0.5 mg/ml hygromycin B (Corning™). The cell line identities and the absence of *mycoplasma* infection were confirmed by PCR-based assays.

L. Fn14 Expression Analysis by Western Blotting

Cells were harvested by scraping and lysed in RIPA buffer (150 mM NaCl, 0.5% sodium deoxycholate, 0.1% SDS, 50 mM Tris, and 1% Triton X-100) supplemented with a protease/phosphatase inhibitor cocktail (Cell Signaling Techology™). Mouse tissues were lysed in a similar manner. The protein concentration of each lysate was determined by BCA protein assay (Pierce Protein Biology™). Equal amounts of protein were subjected to SDS-PAGE (Life Technologies™) and electrotransferred to PVDF membranes (Thermo Scientific Pierce™) Immunoblotting was performed using Fn14 and glyceraldehyde-3-phosphate dehydrogenase (GAPDH) antibodies.

M. Evaluation of Fn14 Expression in Cells

To examine Fn14 surface expression in the U87-Luc/GFP cell line, we performed flow cytometry analysis. Briefly, cells (about 10$^6$) were incubated with no antibody, IgG isotype, or ITEM4 for 30 minutes on ice. Next, cells were washed 3 times with FACS buffer and a fluorescent secondary antibody (anti-mouse IgG-APC) was added and allowed to incubate for 15 minutes. After washing 3 times in FACS buffer, cells were assayed for APC mean fluorescence intensity using a FACSCalibur™ flow cytometer (Becton Dickinson™, Franklin Lake, N.J.). Data from 10,000 events were gated using forward and side scatter parameters to exclude dying cells and debris.

Fn14 expression in the two MEF cell lines, MEF 3.5−/− and MEF Fn14-V5, was determined using both western blot and flow cytometry analyses. For western blotting, cells were harvested by scraping and lysed in 20 mM HEPES, 150 mM NaCl, 1.5 mM MgCl$_2$, 10% glycerol, and 1% Triton X-100 supplemented with a protease inhibitor cocktail (Sigma Aldrich™, St. Louis, Mo.) and two phosphatase inhibitor cocktails (Calbiochem™, Billerica, Mass.). The protein concentration of each lysate was determined by BCA protein assay (Pierce Protein Biology™, Rockford, Ill.). Equal amounts of protein were subjected to SDS-PAGE (Life Technologies™, Grand Island, N.Y.) and electrotransferred to PVDF membranes (Millipore™, Billerica, Mass.). Membranes were blocked in 5% non-fat dry milk (NFDM) in TBST buffer and then sequentially incubated with either an anti-Fn14 antibody (Cell Signaling Technology™, Danvers, Mass.) or an anti-tubulin antibody (Sigma Aldrich™, St. Louis, Mo.) and then horseradish peroxidase (HRP)-conjugated secondary antibody (Cell Signaling Technology™, Danvers, Mass.). The membranes were washed in TBST and then immunoreactive proteins were detected using the Amersham™ Enhanced Chemiluminescence Plus kit (GE Healthcare™ Piscataway, N.J.) according to the manufacturer's instructions. For flow cytometry, MEFs (about 10$^6$) were incubated with Mouse Fc Bloc (BD Biosciences™, San Jose, Calif.) for 15 minutes and then incubated with: no antibody, IgG isotype-APC, or ITEM4-APC for 30 minutes on ice. Cells were then washed 3 times with FACS buffer and then assayed for APC mean fluorescence intensity by flow cytometry as described above.

N. Nanoparticle Uptake in Fn14-Positive and Fn14-Negative Cells

Nanoparticle uptake in the MEF 3.5−/−, MEF Fn14-V5, and U87-Luc/GFP cell lines was determined via flow cytometry. Briefly, cells were plated in 24-well plates at a seeding density of 10$^5$ cells per well. Cells were allowed to attach overnight and the following day the media was replaced with serum-free DMEM along with nanoparticles (2 μg per well). Cells were incubated with nanoparticles for 1 hour, washed 3 times with IX PBS, detached with trypsin, and diluted in cold IX PBS for flow cytometry analysis. Mean fluorescence intensity was analyzed using a BD LSR Fortessa™ flow cytometer (Becton Dickinson™, Franklin Lake, N.J.). Data from 10,000 events were gated using forward and side scatter parameters to exclude dying cells and debris.

O. Nanoparticle Internalization in Fn14-Positive GBM Cells

The internalization of CNP-ITEM4 in U87-Luc/GFP cells was confirmed by live-cell confocal microscopy at 37° C. and 5% CO$_2$. Briefly, cells were seeded between 2.0 to 2.5×10$^3$ cells per plate onto Lab-Tek™ glass-bottom culture plates and incubated overnight at 37° C. After overnight incubation, culture medium was replaced with fresh media before nanoparticles (2 μg per well) were added. Prior to imaging, the U87-Luc/GFP cells were treated for 15 minutes with Hoechst™ 34580 (5 μg/mL) to stain the nucleus. Following incubation, cells were washed 3 times with 1×PBS and replaced with Opti-MEM™ (Invitrogen™ Corp., Carlsbad, Calif.). Cells and nanoparticles were then imaged under a Zeiss™ LSM510 Meta confocal microscope (Carl Zeiss™ Inc., Thornwood, N.Y.) using a 63× Plan-Apo/1.4 NA oil-immersion lens. For multi-color microscopy, samples were excited with 405, 488, 543 and 633 nm laser lines, and images were captured by multi-tracking to avoid bleed-through between fluorophores.

P. Nanoparticle Transport in Rat Brain Slices

The diffusion of individual fluorescent nanoparticles in rat brain slices was quantitated via multiple particle tracking (MPT) as previously described. Briefly, Sprague-Dawley rats (6-8 weeks) were euthanized, the brain was harvested and incubated in artificial cerebrospinal fluid (aCSF, Tocris Bioscience™, Bristol, UK) for 10 minutes on ice. Brain was sliced into 1.5 mm coronal sections using a Zivic™ brain matrix slicer (Zivic Instruments™, Pittsburgh, Pa.). Slices were added to custom microscope slide chambers and fluorescent nanoparticles were injected (0.5 μL of 20 μg/mL stocks) into the middle of cortical tissue. Slides were sealed with super glue and allowed to incubate at room temperature for a minimum of 15 minutes before imaging. The movement of individual nanoparticles in brain slices was imaged, at a frame rate of 15 frames/sec for a total of 300 frames (20 seconds), using an inverted epi-fluorescent microscope (Axiovert™ D1, Zeiss™, Thornwood, N.Y.) with a 100×/1.46 NA oil-immersion objective equipped with an Evolve™ 512 EMCCD camera (Photometries™, Tucson, Ariz.). Movies were analyzed using a custom written MATLAB automated tracking code to extract x-, y-coordinates of nanoparticles over time, as previously described. At least three rat brains were imaged per each nanoparticle type with at least 100 particles tracked per sample. The geometric mean of the mean squared displacement (MSD) was calculated per sample and the average of different rodent brains was calculated as a function of time scale.

Q. Intracranial Implantation of U87-Luc/GFP Tumors

All animal procedures were approved by the University of Maryland Institutional Animal Care and Use Committee (IACUC) and the Office of Animal Welfare Assurance (OAWA). Athymic nude mice (age, 6-8 weeks) were purchased from the University of Maryland School of Medicine Veterinary Resources. For the tumor implantation procedure, animals were anesthetized via continuous flow of 2 to 3% isoflurane through a nose cone. Using a stereotactic frame and sterile technique, about 4.0×10$^5$ U87-Luc/GFP GBM cells were injected at a rate of 1 μL/min over 5 minutes into the left frontal lobe of the brain through a burr hole; drilled 2 mm lateral to the sagittal suture and 1 mm anterior to the coronal suture at a depth of 3 mm below the dura. Mice were given the analgesic buprenorphine (Buprenex, 0.05 mg/kg, subcutaneously) after the surgery. Animals were observed daily for any signs of deterioration or neurological dysfunction. If the symptoms persisted and resulted in debilitation, animals were euthanized according to protocol.

R. In Vivo Bioluminescence Imaging

Intracranial U87-Luc/GFP mouse tumors were imaged using a Xenogen™ IVIS system (Caliper Life Sciences™, Hopkinton, Mass.). Anesthesia was induced in an induction chamber with 2.5% isoflurane in 100% oxygen at a flow rate of 1 L/min and maintained in the IVIS system with a 2.0% mixture at 0.5 L/min. The mice were injected with D-luciferin (150 mg/kg, intraperitoneally; dissolved in PBS) and returned to their home cages. Ten minutes following the D-luciferin injection, anesthesia was induced with isoflurane in an induction chamber. The animal was moved to the IVIS imaging chamber and maintained on 2 to 3% isoflurane.

Photons emitted from live mice were acquired as photons/s/cm 2/steradian (p/s/cm 2/cm 2/sr) and analyzed using LivingImage™ software (PerkinElmer™, MA).

S. Bioluminescence Imaging

For the BLI of the tumors, animals were anesthetized in an induction chamber with 2.5% isoflurane and injected with D-luciferin (150 mg/kg, dissolved in PBS) intraperitoneally. After 10 minutes, animals were moved to the Xenogen™ IVIS system maintained at 2.5% isoflurane and imaged for tumor bioluminescence. Photons emitted from live mice were acquired as photons/s/cm2/steradian (p/s/cm2/cm2/sr) and analyzed using LivingImage™ software.

T. Nanoparticle Cellular Internalization Analysis by Confocal Microscopy

Cellular internalization of rhodamine-labeled nanoparticles in 231-Luc cells was confirmed by live-cell confocal microscopy. Briefly, 231-Luc cells were seeded onto Lab-Tek™ glass-bottom culture plates at a density of $10^5$ cells per plate and allowed to attach overnight. The media then was replaced with fresh media containing nanoparticles (100 µg per well). After a 1 hour incubation, cells were treated for 15 minutes with Hoechst™ 33342 (5 µg/mL) to stain the nuclei and then washed 3 times with PBS. Clear Opti-MEM™ (Invitrogen™ Corp.) media was added to the plates and the cells and nanoparticles were imaged under a LSMS Duo slit scanning confocal microscope (Carl Zeiss™ Inc.) with a 63× Plan-Apo/1.4 NA oil-immersion objective.

U. Intracranial Injection of Nanoparticles

At day 7 after the implantation of U87-Luc/GFP tumor cells, bioluminescent signal from the engrafted brain tumors was confirmed in each animal. Once tumor signal was confirmed, the animals were anesthetized as described above and nanoparticles suspended in normal saline were administered sterilely into mouse brain (n=3) through the same burr hole using a stereotactic frame. CNP and CNP-ITEM4 (high) nanoparticles in normal saline were loaded into a sterile 30-gauge Hamilton syringe needle, lowered to a depth of 3.5 mm, and injected slowly: 5 µL (0.1 mg/ml nanoparticles) at a rate of 1 µL/min over 5 minutes.

V. Nanoparticle Distribution in the Brain and Intracranial Human GBM Xenograft

The distribution and co-localization of fluorescent nanoparticles with U87-Luc/GFP tumors in the brain was evaluated by imaging brain cryosections. The animals were euthanized with an overdose of isoflurane 24 hours after the injection of nanoparticles. The euthanized animals were perfused with 30 mL of IX PBS after which the brains were carefully removed, embedded in Optimal Cutting Temperature™ (OCT), and stored at −80° C. A cryostat (Leica™ CM3050 S) was used to cut serial 10 µm sagittal brain sections and mounted on positively charged microscope slides. The brain sections were stained with Prolong Gold™ antifade with or without DAPI (Invitrogen™, Carlsbad, Calif.), sealed with coverslips, and imaged for cell nuclei (dark blue), CNPs (light blue), GFP-positive U87 tumors (green), and CNP-rfEM4 (high) nanoparticles (red) using a Nikon™ epifluorescence microscope under 10× and 20× magnification. High resolution stitched images (6×6) were obtained by using the montage imaging feature in the Nikon™ NX 2 software. Microscope settings were carefully optimized to avoid background fluorescence based on non-injected control mouse brains, where the exposure time for each channels were kept constant throughout the study.

W. Nanoparticle Biodistribution and Tumor-Specific Targeting to Breast Tumor Xenograft Following Systemic Administration Individual female Nu/Nu mice (6-8 weeks old) were injected with MDA-MB-231/Luc Ctrl and MDA-MB-231/Luc Fn14 shRNA 448 cells in the left and right flank, respectively ($1\times10^6$ cells each). Tumor growth was monitored by bioluminescence imaging (BLI) and caliper measurements. When each tumor reached about 100 mm in volume, near infrared (NIR)-labeled non-targeted coated nanoparticles (CNPs) or ITEM4-CNPs were administrated via the tail vein. At 72 hours after injection, the mice were euthanized and dissected. Blood, organs (heart, liver, spleen, kidney, lung, stomach, intestine, uterus, skin, muscle, bone, brain), and tumors were isolated and placed on a petri dish and assessed for biodistribution and tumor targeting capabilities by quantitative optical imaging.

X. In Vitro Cytotoxicity Assays

For cytotoxicity assays, 231-Luc cells were cultured in 96-well plates at $5\times10^3$ cells/well for 24 hours. Culture media was removed and replaced with media containing various treatment groups. First, the cytotoxicity of PTX and Abraxane™ were confirmed by treating cells with PTX and Abraxane™ and measuring cell viability after 24 hours of treatment exposure using the MTS assays (CellTiter 96® Aqueous One, Promega™). Further, to assess the cytotoxicity of nanoparticles as a result of nanoparticle uptake and clearance by the cells, PTX, Abraxane™, or non-targeted and Fn14-targeted PTX-loaded nanoparticles were added to the cells. The culture media was removed after 2 hours of incubation to mimic the clearance mechanism and replaced with fresh culture media. Cell viability was then measured after 24 hours with percent viability calculated as absorbance relative to control wells (cell with culture media). A total of 3 wells were used per treatment per concentration for each experiment.

Y. In Vivo Safety Profile

For in vivo safety studies, 200 µL of saline, Abraxane™, PLGA-PEG-IgG-PTX or PLGA-PEG-ITEM4-PTX (n=9) were injected at a concentration of 10 mg/kg PTX via the tail vein of tumor bearing mice. Care was taken to avoid delivery of air bubbles that can produce embolism. At 96 hours after injection, mice were euthanized as previously described and organs were isolated and fixed in paraformaldehyde for H&E staining. Blood and blood serum were also collected for whole blood cell and hepatic enzyme analyses, respectively (VRL Laboratories™)

Z. Intravenous Injection of Fluorescent Nanoparticles for Systemic Circulation and Tumor Accumulation Analysis Individual mice were restrained briefly in a Tailveiner® apparatus (Braintree Scientific™), which is specially designed for tail vein injections. The tail was then prepared aseptically by Betadine™ scrub, followed by 70% ethanol rinse. For systemic circulation studies, 200 µL of NIR PS-based nanoparticles (1 mg/mL) or rhodamine-labeled PLGA-based nanoparticles (10 mg/mL) were injected in non-tumor bearing mice via the tail vein using a 32-gauge needle. Care was taken to avoid delivery of air bubbles that can produce embolism. At designated time points mice were anesthetized as previously described and NIR signal of PS-based particles was detected using the Xenogen™ IVIS system. For PLGA-based particles the mice were euthanized and livers, spleens, and kidneys were isolated. The organs were placed on a petri dish and rhodamine signal was detected using a Xenogen™ IVIS system.

Identical imaging acquisition settings (time, 2-30 seconds; ex/em, 710/760; F-stop, 1; binning, medium) and the same area of regions of interest (ROI) were used to obtain total radiance (photons/sec/cm2/sr) of the fluorescence signals. Images were processed using the LivingImage™ Software (IVIS Spectrum™, Perkin Elmer™). The total radiance from the fluorescence readings was used for signal quantification. Similarly, for tumor accumulation studies, 200 µL of rhodamine-labeled PLGA-based nanoparticles (10 mg/mL) were injected in mice bearing 231-Luc mammary fat pad tumors (>500 mm³ in volume) as well as 231-Br-Luc intracranial tumors via the tail vein. After 24 hours of injections, the mice were euthanized and tumors were isolated, placed on a petri dish, and imaged for rhodamine signal using Xenogen™ IVIS system.

AA. Implantation of 231-Luc Cells in Mammary Fat Pad

All animal procedures were approved by the University of Maryland Institutional Animal Care and Use Committee (IACUC) and the Office of Animal Welfare Assurance (OAWA). For the tumor implantation procedure, athymic nude female mice (age 6-8 weeks, Taconic Biosciences™) were anesthetized via continuous flow of 2-3% isoflurane through an induction chamber followed by a nose cone. 231-Luc cells (1×10⁶) were suspended in 50% Matrigel™ and implanted subcutaneously proximal to the mammary fat pad of mice. Every 2 to 3 days, perpendicular tumor diameters were measured by digital caliper and used to calculate tumor volume according to the formula:

$$\text{volume} = L \times W \times W/2,$$

where L indicates the larger diameter and W indicates the smaller diameter.

BB. Intracranial Implantation of 231-Br-Luc Cells

Mice were anesthetized via continuous flow of 2.5% isoflurane through a nose cone and were secured to a stereotactic frame. Using a handheld drill, a burr hole was drilled into the left frontal lobe of the brain 2 mm lateral to the sagittal suture and 1 mm anterior to the coronal suture at a depth of 3 mm below the dura of all animals. Using a Hamilton syringe attached to the stereotactic frame, 231-Br-Luc (3×10⁵) cells were injected at a rate of 1 μL/min over 5 minutes through the burr hole. Mice were given the analgesic Rimadyl™ (Carpofen™, 3 mg/kg) subcutaneously after the surgery. Animals were observed daily for any signs of deterioration or neurological dysfunction. If the symptoms persisted and resulted in debilitation, animals were euthanized according to protocol.

CC. Nanoparticle Penetration in Breast Tumor Slices

The diffusion of individual nanoparticle was analyzed using MPT assays in ex vivo breast tumor slices. Mice bearing 231-Luc xenografts (approximately 100 mm3 in volume) were euthanized and the tumors were harvested and sliced into 2 mm sections using a Zivic™ matrix slicer (Zivic™ Instruments). Slices were added to custom microscope slide chambers and rhodamine-labeled nanoparticles were injected (0.5 μL of 100 μg/mL) into tumor slices using a Hamilton™ syringe aided by a stereotactic frame. Cover slips were placed on the slide chambers and sealed with super glue. Slices were incubated at 37° C. for a minimum of 15 minutes before imaging to allow tissue recovery and convection dissipation. Diffusion of nanoparticles was imaged at a frame rate of 20 frames/sec for a total of 400 frames (20 seconds) using LSMS Duo slit scanning confocal microscope with 63× Plan-Apo/1.4 NA oil-immersion objective. Particle movement movies were analyzed using a custom written MATLAB automated tracking code to extract x, y-coordinates of the nanoparticles over time. The geometric mean of the MSD was calculated per sample and the average MSD was plotted as a function of time scale. The theoretical MSD values of nanoparticles in water were calculated from the Stokes-Einstein equation using the mean particle diameters, measured by dynamic light scattering.

DD. In Vivo Efficacy Experiments Using 231-Luc Orthotopic Tumor Model

Mice bearing orthotopic 231-Luc tumors (100-200 mm³) were randomized into four groups, each containing either 5 mice for intratumoral delivery or 9 mice for systemic delivery of therapeutics. For the intratumoral delivery experiment, mice received 10 μL of saline, Abraxane™, PLGA-PEG-PTX, or PLGA-PEG-ITEM4-PTX at a single dose of 1 mg/kg of PTX. The rate of change of tumor volumes were measured and compared between the groups. For the systemic efficacy experiment, three groups of mice were given Abraxane™, PLGA-PEG-IgG-PTX, or PLGA-PEG-ITEM4-PTX intravenously via tail vein at a single dose of 10 mg/kg PTX. The control group received saline (200 μL) injected intravenously on the same day as the PTX treatments. Mouse body weight and tumor sizes (see above) were monitored every 2-3 days. Mice were euthanized when tumor volumes reached 1800 mm³. Survival comparisons between groups were analyzed by Kaplan-Meier and the log-rank test.

EE. In Vivo Efficacy Experiments Using 231-Br-Luc Intracranial Tumor Model

Mice bearing 231-Br-Luc intracranial tumors were randomized into four groups (n=9/group) 7 days post-tumor cell implantation based on BLI measurements. Three groups of mice were given Abraxane™, PLGA-PEG-IgG-PTX, or PLGA-PEG-ITEM4-PTX intravenously via tail vein at a single dose of 10 mg/kg PTX. The control group received saline (200 μL) injected intravenously on the same days as the PTX treatments. Post-drug administration, mouse body weight and tumor growth were monitored every 2-3 days. Tumor growth was evaluated via BLI monitoring as described above. Mice were euthanized when body weight dropped more than 20% and/or if animals showed any signs of discomfort or neurological abnormalities. Survival comparisons between groups were analyzed by Kaplan-Meier and the log-rank test.

FF. Statistical Analysis

Statistical analysis of data was performed by a two-tailed Student's t test assuming unequal variances or one-way analysis of variance (ANOVA) followed by Tukey HSD or Games-Howell tests using SPSS 18.0 software (SPSS Inc., Chicago, Ill.) unless otherwise indicated. In some cases, the tests used are indicated in the examples or figure legends. Differences were considered to be statistically significant at a level of $P<0.05$. GraphPad™ software was used.

Example 2: Brain Penetrating Nanoparticles (BPN)

Figure 1B:
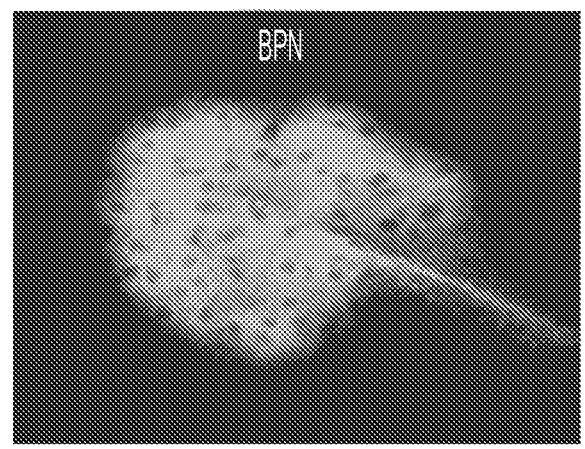

Previous studies had suggested that the mesh spacing in brain ECS is no larger than about 20-40 nm, and a restricted movement of 35 nm polyethylene glycol (PEG)-coated quantum dots (QD) has been shown in rat brain. It was hypothesized that poor penetration of PEG-coated QD was due to adhesive interactions between the QDs and the ECM owing to inadequate coating of PEG on the QD surfaces. However, drawing on experience with mucus-penetrating particles [28], densely coated 40-200 nm polystyrene (PS) particles with low molecular weight PEG, were injected into rat brains, and then visualized particle spread. Uncoated PS nanoparticles did not penetrate, whereas dense PEG-coated PS penetrated >100 μm beyond the injection site within just 1 hour. (FIG. 1). These highly dense PEG coated particles are referred to as "brain-penetrating nanoparticles" (BPN) and the non-coated counterparts "uncoated nanoparticles" (UCN).

Example 3: Fn14 Expression by Invading GBM Cells

Fn14 is minimally expressed in normal human brain but highly expressed in high-grade gliomas with more malignant and invasive characteristics. Furthermore, high Fn14 expression correlates with poor patient outcome. These findings suggest a major role for Fn14 in the pathobiology of GBM. Fn14 is overexpressed in GBM cells invading the normal brain parenchyma (FIG. 2). In FIG. 2A, hematoxylin and eosin staining of the edge of a malignant glioma biopsy specimen shows the dense cellular tumor core and the infiltrating tumor cells at the rim of the tumor. Laser capture microdissection at the tumor edge in FIG. 2B followed by RNA isolation and quantification of Fn14 mRNA levels using real time quantitative polymerase chain reaction [rtPCR] shows significantly increased expression in the invasive cells. Forced Fn14 overexpression in glioma cells stimulated both cell migration and invasion, suggesting that tumor cells with the highest levels of Fn14 on their surface may also have the greatest invasive capacity. These findings differentiate Fn14 from other GBM targets (i.e., EGFR, IL13R, Tenascin C) and indicate that Fn14 may be an ideal surface molecule for targeting invasive, malignant glioma cells.

Example 4. Specific and Non-Specific Binding of Fn14-Targeted BPNs in Glioblastoma Data demonstrate that BPNs conjugated to the anti-Fn14 monoclonal antibody ITEM4 bind to immobilized Fn14 but not brain ECM components. In FIG. 3A, SPR analysis measures the binding to the Fn14 receptor: free ITEM4 monoclonal antibody, BPNs with varying surface densities of ITEM4, and non-targeted BPNs. In FIG. 3B, SPR analysis measures the binding of uncoated polystyrene NPs and BPNs with varying surface densities of ITEM4 to mouse brain ECM. The brain ECM SPR chip was validated using monoclonal antibodies recognizing several common brain ECM components. FIG. 3C illustrates human U87 glioma cells treated with fluorescent BPN or ITEM 4 conjugated BNP.

ITEM4 conjugation (high density) resulted in a ~4.5-fold increase in BPN binding to glioma cells in culture as measured by multiple particle tracking (MPT), a method that was developed to quantify the non-convective movement of hundreds of individual nanoparticles in brain ECS using in vivo imaging (FIG. 3C). Most importantly, ITEM4 conjugation to the BPN surface does not appear to inhibit the movement of BPNs in brain tissue (FIG. 3D). Therefore, in summary, Fn14-targeted nanoparticles according to the invention bind strongly to Fn14, bind minimally to ECM in brain, show improved glioblastoma cell uptake, and unchanged brain diffusion.

Figure 4A:
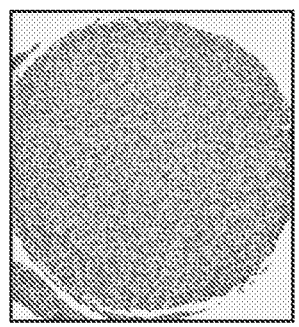
FIG. 4A and FIG. 4B are photographs illustrating the Fn14+ GBM44 PDX model.
Figure 4B:
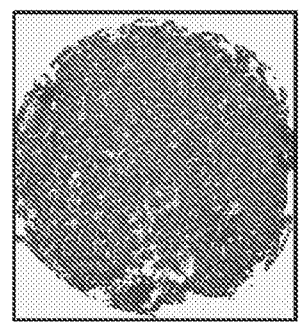
Figure 4C:
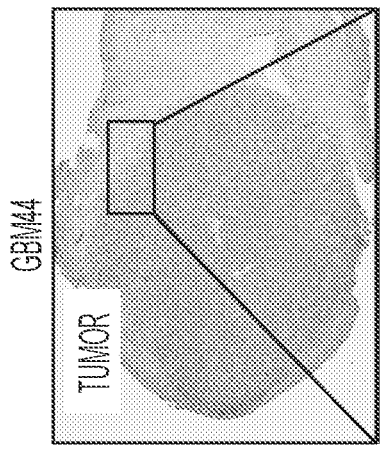
FIG. 4C shows a coronal brain section of GBM44 tumor with FIG. 4D showing an enlarged view of the invasive rim showing invading human GBM cells.
Figure 4D:
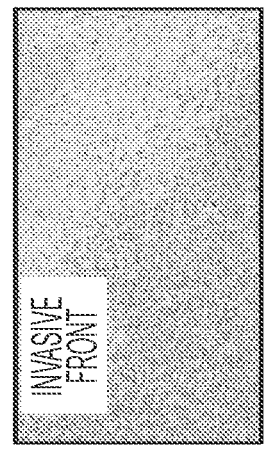
FIG. 4E is a graph showing some efficacy of TMZ in GBM44 PDX model.
Figure 4E:
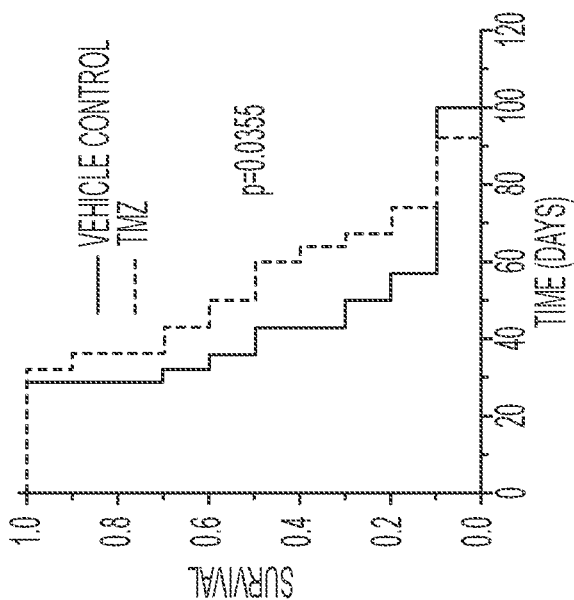

Example 5. Patient-Derived GBM44 Cells Show High Fn14 Expression, BrainI, and TMZ Sensitivity To assess if BPNs (with or without Fn14 targeting) will enable improved delivery and efficacy in a translationally-relevant human GBM model, a well-characterized Fn14+, patient-derived GBM cell line, GBM44, was used. This PDX model was initially generated by the immediate transfer of tumor tissue into immunodeficient mice and has been passaged over time as a subcutaneous tumor. GBM PDX models maintain histologic and genetic characteristics of the original patient tumor during in vivo passaging. Furthermore, the invasive nature of human GBM cells is recapitulated in PDX xenograft models. The GBM44 PDX line expresses high levels of Fn14 (FIG. 4A) and after intracranial injection it invades the normal brain parenchyma (FIG. 4B). The Fn14+ GBM44 PDX tumor is also susceptible to treatment with temozolomide (TMZ) (FIG. 4C), suggesting that the model system has significant translational relevance.

Example 6: Analysis of Fn14 Expression in Human Glial Tumors

Figure 5B:
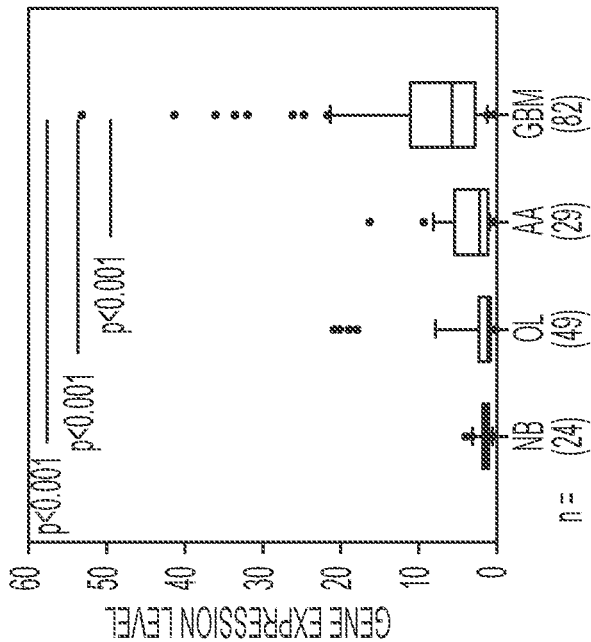
FIG. 5A and FIG. 5B are graphs illustrating analysis of Fn14 mRNA expression in human glial tumors.
Figure 5A:
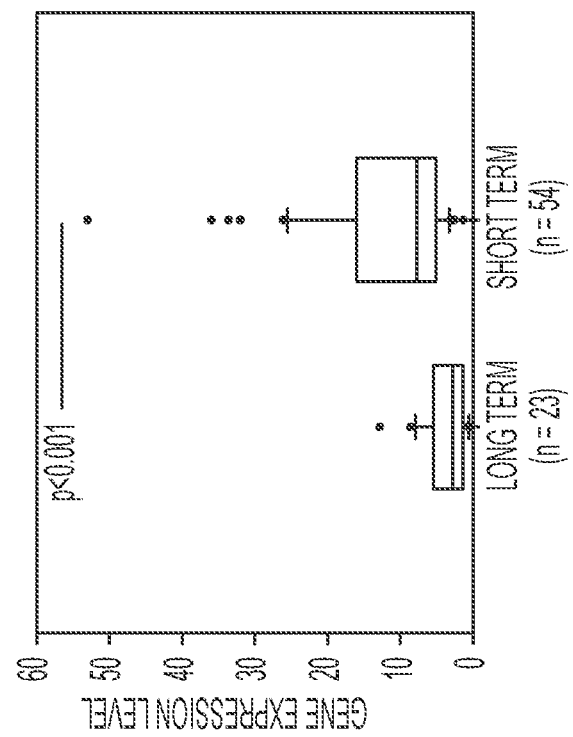

Increasing Fn14 expression correlates with higher glioma grade and shorter survival time. The Fn14 transcript levels were analyzed in the glioma specimens and normal tissue from epilepsy cases. The data were also compared based on survival times by categorizing patients into two groups: short term and long-term survival. This analysis showed the patients with high Fn14 expression GBMs did not live as long. The results also confirmed the hypothesis that increasing Fn14 expression is found in higher grade gliomas with more malignant and invasive characteristics. In FIG. 5A and FIG. 5B, analysis of Fn14 expression in human glial tumors revealed expression levels of Fn14 mRNA in 184 normal and brain tumor specimens (FIG. 5A). GBM showed significantly higher Fn14 expression levels compared to either nonneoplastic brain (NB), oligoastrocytoma (OL), or anaplastic astrocytoma (AA). FIG. 5B shows the expression values of Fn14 mRNA were analyzed in two clusters. Cluster One had a survival mean of 401 days (short-term survival) and Cluster Two had a survival mean of 952 days (long-term survival). Fn14 expression levels were significantly higher in the short-term survival cluster.

Figure 6D:
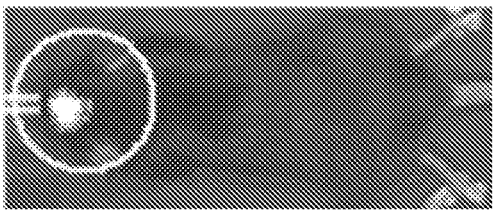
FIG. 6D AND FIG. 6E are photographs showing this decrease.
Figure 6C:
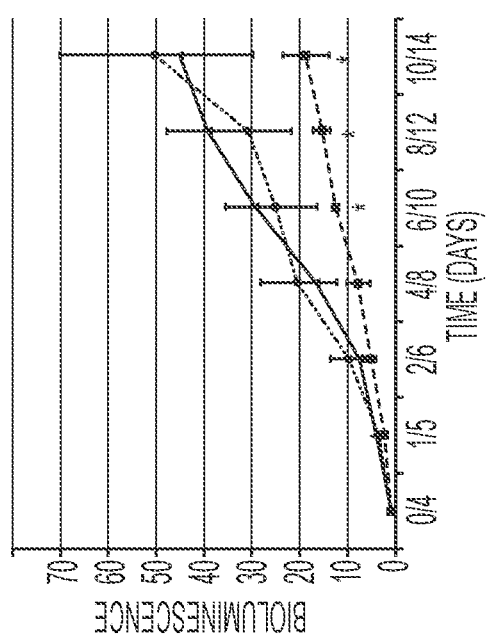
FIG. 6C is a graph which presents bio-luminescent imaging (BLI) of GL261L cells in vivo showing a decrease in BLI signal over time in animals treated with nanovectors carrying shLuc plasmid.
Figure 6E:
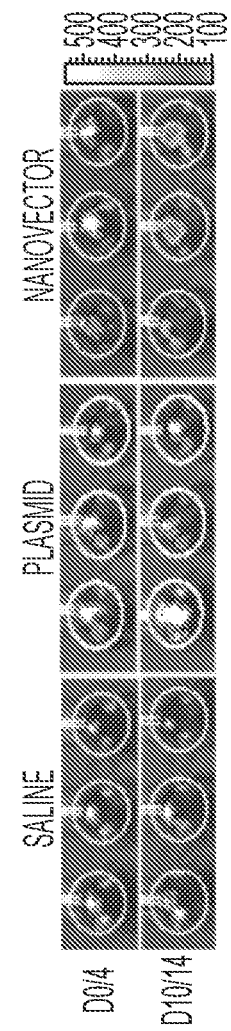
Figure 6A:
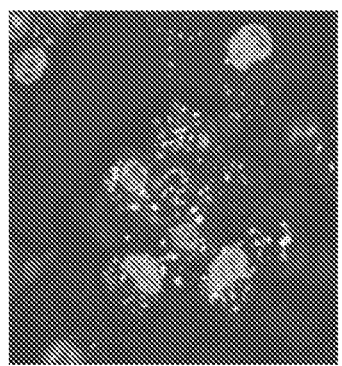
FIG. 6A and FIG. 6B are photographs illustrating nanoparticle-based delivery systems comprising polymeric nanovectors modulating mouse glioma.
Figure 6B:
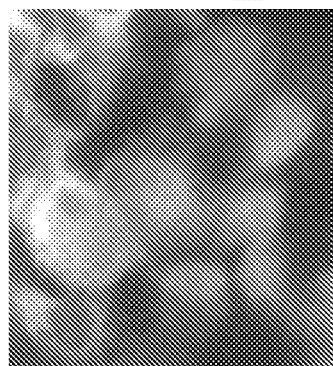

Example 7. Delivery Systems Including Polymeric Nanovectors Mediate Efficient Gene Transfer to Glioma Cells and Tumors Polymeric nanogene vectors designed to protect DNA in vivo were engineered to enable efficient cellular trafficking and transgene expression. The ability to knockdown a model gene in brain tumors was tested. Nanovectors containing luciferase shRNA plasmid were directly applied to luciferase-expressing glioma cells in culture and to intracranial tumors (FIG. 6A, FIG. 6B, and FIG. 6C). Nanovectors efficiently entered cells and silenced the tumor-specific transgene (luciferase) in vitro and in vivo. Specifically, nanovectors efficiently entered mouse glioma cells [GL261] (FIG. 6A) and after entering the cells, nanovectors effectively delivered a plasmid gene construct with green fluorescent reporter and inhibitory RNA for luciferase (shLuc) to GL261 cells that constitutively express luciferase GL261L (FIG. 6B). In FIG. 6C, data show that BLI of GL261L cells in vivo have significant BLI silencing using nanovectors carrying shLuc plasmid (dotted line).

Example 8. Fn14 is Highly Expressed on Glioma Cell Lines

To confirm elevated Fn14 gene expression in model glioma cell lines, Fn14 mRNA levels were assessed. See FIG. 7. FIG. 7 is a western blot that illustrates Fn14 is expressed in GBM cell lines. Total cell lysates were prepared from various GBM cell lines and equal amounts of protein were immunoblotted with anti-Fn14 and anti-tubulin antibodies. The highest Fn14 expression occurred in the A172 cell line.

Example 9. Formulation of PEI-Based BPN Gene Vectors

PEG-PEI nanoparticles were formulated as previously described. For PEG-PEI particles with targeting ligands, hetero-bifunctional PEG, Malemide-PEG-Succinimidyl Carboxy Methyl ester was first conjugated to branched PEI, followed by ligand conjugation through the thiol-maleimide linkage. Ligands for this conjugation step may include: TWEAK and Fn14 monoclonal antibody or antibody fragments. Particle types may include PEG-PEI, PEG Dendrimer, and PEG CK30. Formulation variables include polymers (PEI, PEI-PEG, Dendrimer-PEG, and CK3O-PEG. PEG may have a coating density MW of 5 kDa to 10 kDa. Polymer concentrations and solvents and surfactants are readily available and known in the art. Characterization methods can include dynamic light scattering (size and net surface charge), electron microscopy (morphology and size confirmation) and fluorometric binding assays and confocal microscopy (quantification of PEG density).

Particle transport rates were measured by analyzing trajectories of fluorescent particles, recorded by using a silicon-intensified target camera (Strome/Hanes™ Labs) mounted on an inverted epifluorescence microscope. MPT analysis in brain tissue was performed as previously described. Low passage Fn14+U118 glioma cells were grown in glass chambers. Targeted BPN gene vectors containing a GFP reporter plasmid were added to cells and incubated. Confocal microscopy was used to assess cell morphology (toxicity) and count GFP+ cells per high power field (HPF) to compare transfection rates. Cells were trypsinized and flow cytometric analysis used to quantify the percent GFP+ transfection for each treatment group.

Example 10. Distribution and Reporter Gene Transfer Via BPNs to Invading Fn14+ Human Glioma Cells For the organotypic brain slice migration assay, gene vectors were formulated with brain penetrating characteristics using 5K PEG-PEI diblock polymers and fluorescently labeled plasmid DNA. These particles were then co-injected with model BPN in the living mouse brain. See FIG. 8. For FIG. 8A, conventional, uncoated nanoparticles were injected into the living mouse brain showing minimal diffusion or transport. Optimized model BPN in FIG. 8B rapidly distributes within the mouse brain. In FIG. 8C, BPN gene vectors also penetrated well in brain tissue. An overlay in FIG. 8D shows model BPN and BPN gene vectors having a close overlap of the two particle types.

Laser scanning microscopy was used to image the particle spread using an in vivo, closed cranial window mouse system. This showed a nearly exact distribution overlap of the gene vectors and model BPNs. Fluorescently-labeled BPN PEG-PEI gene vectors were also analyzed ex vivo in fresh brain slices using MPT. This analysis correlated well with the in vivo imaging comparison shown here. These preliminary results suggested the ability to successfully make BPN gene vectors using a well-known and characterized polymeric gene vector system.

Example 11. Green Fluorescent Protein Expressing Fn14+ Human Glioma Cells Invade in Fresh Brain Slices An ex vivo brain slice migration assay was developed using GFP+, Fn14+ human glioblastoma cells (U118) and fresh mouse brain in organotypic culture conditions. FIG. 9 shows photographs of U118 GFP+ cells placed on fresh mouse brain slices and incubated for 1, 24, and 48 hours. For this analysis, C57BL/6 mice were euthanized with isoflurane and cervical dislocation. The brain was removed and 400 μm thick slices (6-8/mouse) were cut using a vibratome. The slices were then placed on top of a transwell membrane chamber full of cell culture media (DMEM). GFP+U118 cell suspension was placed on top of each brain slice, then incubated for 24-48 hours. Quantitation involved brief fixation then confocal microscopy using Volocity™ Image software to calculate depth of invasion of GFP+ cells. The above brain slice migration assay was set up and nanoparticles (plasmid dsRED reporter) was mixed with the GFP+U118 cells at the time of placement on the brain slice. Imaging analysis included confocal microscopy with distance measurements and qualitative assessments of particle locations, cell locations, and cell transfection. The tissue was digested to create a signal cell suspension.

Example 12. Synthesis and Characterization of Fn14-Targeted Nanoparticles

Figure 10A:
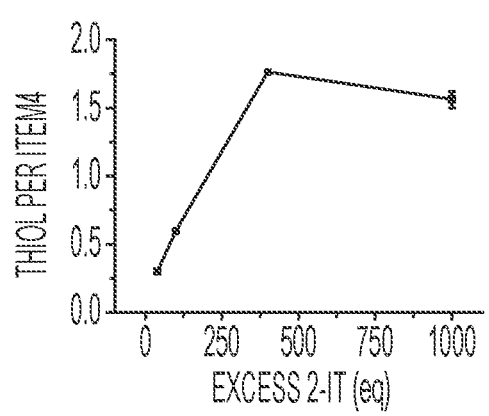
FIG. 10A and FIG. 10B are graphs showing reaction conditions for the optimization of thiol-modification of ITEM4 (FIG. 10A) and surface density of ITEM4 for coated nanoparticles ("CNP") (FIG. 10B).
Figure 10B:
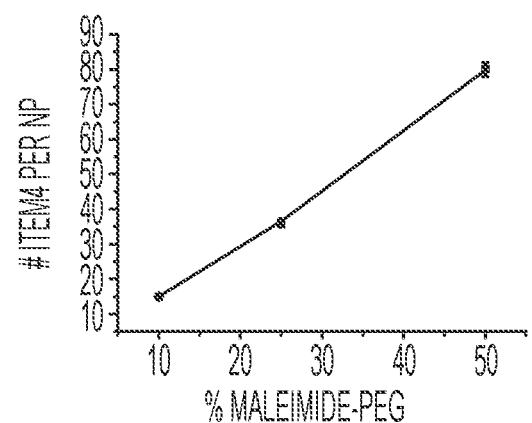

A variety of polystyrene (PS)-based brain tissue penetrating 'coated nanoparticles' (CNPs) that were surface-functionalized were synthesized with a well-characterized antibody, ITEM4, that binds strongly to Fn14. Reaction conditions, including the molar excess of 2-iminothiolane to ITEM4 and the ratio of malemide-PEG5k-amine to methoxy-PEG5k-amine, were optimized to produce CNPs with different surface densities of ITEM4. See FIG. 10A and FIG. 10B. The quantification of ITEM4 thiolation and ITEM4 surface density was measured by thiol quantification assay kit and LavaPep™ Protein Assay, respectively.

Three sets of PEG-coated nanoparticles: no ITEM4 (CNP), decorated with a low density of ITEM4 (CNP-ITEM4 (low)), or decorated with a high density of ITEM4 (CNP-ITEM4 (high)) were compared with conventional, uncoated nanoparticles (UNP) (see Table 2).

TABLE 2

Physicochemical properties of nanoparticles.

| Formulation | Particle Diameter (nm)$^a$ | ζ-Potential (mV)$^b$ | Surface Density of ITEM4 (#/particle)$^c$ |
|---|---|---|---|
| UNP | 95 ± 3 | −54.6 ± 3.0 | — |
| CNP | 113 ± 2 | −7.0 ± 0.2 | — |
| CNP-ITEM4 (low) | 13 ± 3 | −8.7 ± 1.2 | about 11 |
| CNP-ITEM4 (high) | 114 ± 22 | −8.9 ± 0.7 | about 56 |

$^a$Diameter (number mean) measured by dynamic light scattering. Data represents the average of 3 independent experiments +/− SD.
$^b$Measured at 25° C. in 15X diluted PBS, pH 7.4. Data represents the average of 3 independent experiments +/− SD.
$^c$Surface density reported from LavaPep ™ fluorescent protein assay.

CNP, CNP-ITEM4 (low) and CNP-ITEM4 (high) exhibited larger hydrodynamic diameters and more near neutral ζ-potential compared to UNP, as expected for nanoparticles with dense PEG coatings. CNP-ITEM4 (low), and CNP-rfEM4 (high) displayed a slightly more negative surface charge compared to CNP. The number of ITEM4 molecules was quantified on the surface of nanoparticles and it was determined that there were 11 and 56 ITEM4 molecules per particle for CNP-ITEM4 (low) and CNP-ITEM4 (high) nanoparticles, respectively.

Example 13. Biacore™ Screening of Nanoparticles for Fn14 Binding

Figure 11A:
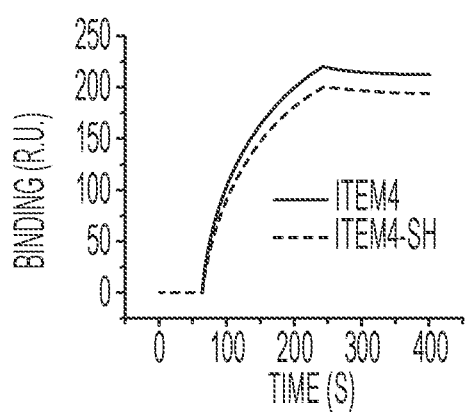
FIG. 11A and FIG. 11B are graphs illustrating SPR analysis measuring ITEM4 antibody and nanoparticle binding to the Fn14 extracellular domain.
Figure 11B:
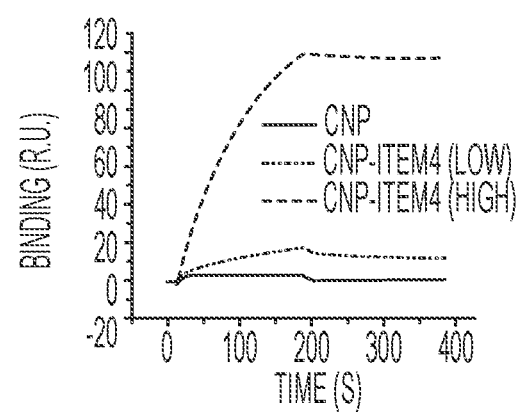

To test the ability of CNP-ITEM4 nanoparticles to bind Fn14, the Fn14 extracellular domain was functionalized to the surface of a Biacore™ chip. SPR analysis was used to measure antibody and nanoparticle binding to the Fn14 extracellular domain. FIG. 11A illustrates free ITEM4 and thiol-modified ITEM4 (ITEM4-SH) and FIG. 11B illustrates CNP and CNP-ITEM4 nanoparticles with two different surface densities of ITEM4. The binding of ITEM4 (unmodified), ITEM4-SH (thiol-modified for surface conjugation to nanoparticles), and CNP formulations was measured with different surface densities of FFEM4. ITEM4 and ITEM4-SH bound similarly, indicating that thiol-modification of ITEM4 does not significantly affect the binding activity of ITEM4 to Fn14. See FIG. 11A. CNP exhibited no appreciable Fn14 binding, whereas both CNP-ITEM4 (low) and CNP-ITEM4 (high) displayed significant Fn14 binding on the chip (FIG. 11B).

Figure 12A:
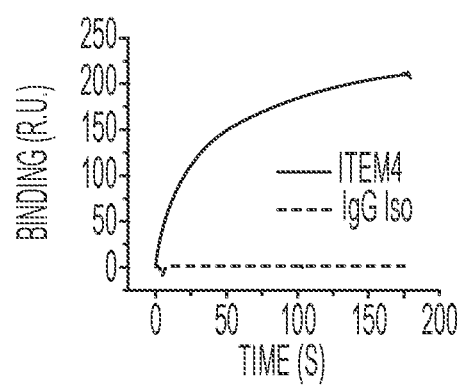
FIG. 12A and FIG. 12B are graphs illustrating specificity of CNP-ITEM4 (high) binding to an Fn14 Biacore™ chip. SPRs show blocking of available Fn14 binding sites with excess (500 nM) ITEM4 (FIG. 12A) and binding of CNP-ITEM4 (high) to Fn14 Biacore™ chips pretreated with either excess IgG isotype control (500 nM) or ITEM4 (500 nM) (FIG. 12B).
Figure 12B:
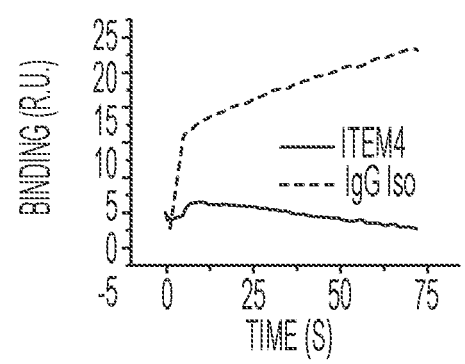
Figure 13C:
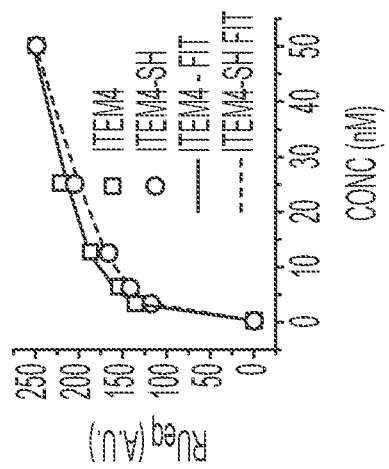
FIG. 13A, FIG. 13B, and FIG. 13C are graphs illustrating SPR analysis of ITEM4 (FIG. 13A), ITEM4-SH (FIG. 13B) binding to Fn14, and KD determination (FIG. 13C).
Figure 13B:
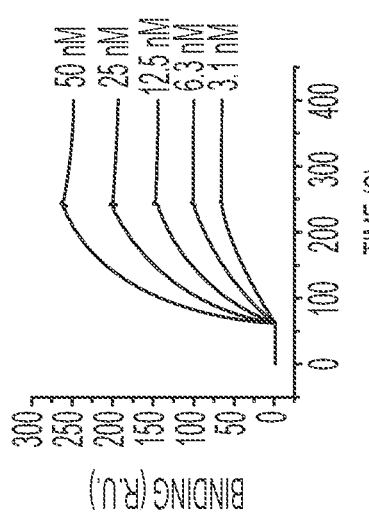
Figure 13A:
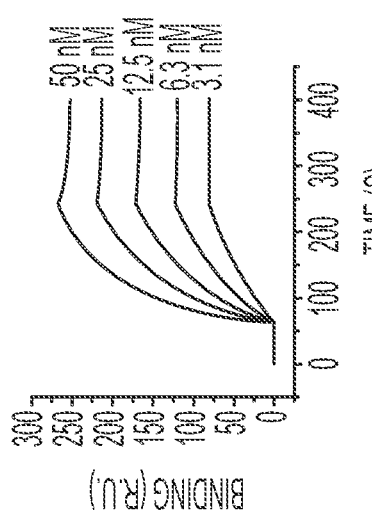

In addition, the binding of CNP-ITEM4 nanoparticles to the chip was proportional to the surface density of ITEM4, as CNP-ITEM4 (high) exhibited stronger binding compared to CNP-ITEM4 (low). To confirm the specificity of CNP-ITEM4 binding to the Fn14 Biacore™ chip, available Fn14 binding sites were first blocked with excess ITEM4 (500 nM) (FIG. 12A), after which CNP-ITEM4 (high) particles were allowed to bind to the chip (FIG. 12B). CNP-ITEM4 (high) bound to the Fn14 Biacore™ chip that was pretreated with control IgG, but not to the chip treated with excess ITEM4 (FIG. 12A and FIG. 12B). To quantify the binding of various CNP-ITEM4 formulations to the Fn14 extracellular domain, their binding affinities ($K_D$) were determined by measuring the binding at various concentrations. The binding data and appropriate fitting procedures for ITEM4 and ITEM4-SH are provided in FIG. 13A, FIG. 13B, and FIG. 13C. These figures are graphs that illustrate characterization of FFEM4 binding to Fn14. SPR analysis in FIG. 13A illustrates ITEM4 and in FIG. 13C ITEM-SH binding at various concentrations. In FIG. 13C, the equilibrium binding affinities for ITEM4 and ITEM4-SH were calculated from fitting SPR data.

Figure 14A:
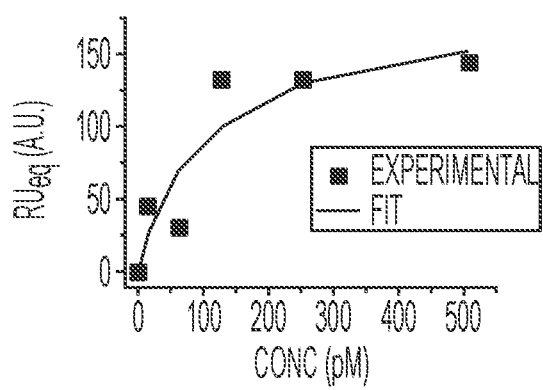
FIG. 14A and FIG. 14B are graphs illustrating SPR analysis of CNP-ITEM4 nanoparticle binding to Fn14.
Figure 14B:
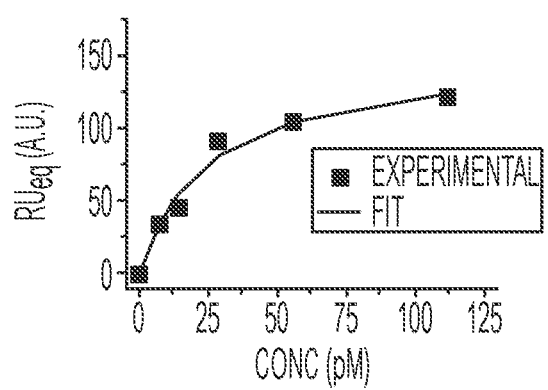

Characterization of CNP-ITEM4 nanoparticle binding to Fn14 is illustrated in FIG. 14A and FIG. 14B. The measured $K_D$ for CNP-ITEM4 (low) and CNP-ITEM4 (high) were 106 pM (FIG. 14A) and 24 pM, (FIG. 14B), respectively. They were about 15- and about 65-fold higher than the binding affinity of ITEM4 alone. Tabulated $K_D$ values for the various ITEM4 and CNP formulations are provided in Table 3.

TABLE 3

Binding Affinities ($K_D$) of Nanoparticles to Fn14 Extracellular Domain.

| Analyte | $K_D$ (nM)$^a$ |
|---|---|
| ITEM4 | 1.62 |
| ITEM4-SH | 1.57 |
| CNP-ITEM4 (low) | 0.106 |
| CNP-ITEM4 (high) | 0.024 |

$^a K_D$ values determined on a per nanoparticle basis from fit of data.

Figure 15A:
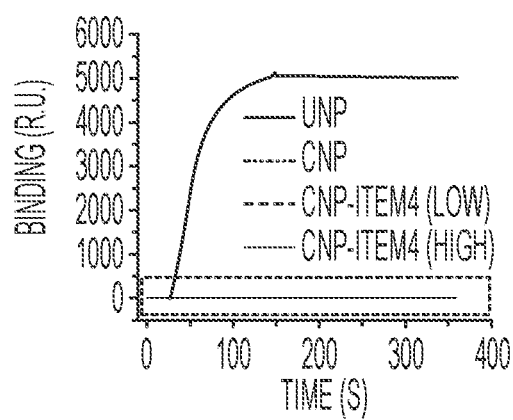
FIG. 15A and FIG. 15B are graphs illustrating SPR analysis measuring the binding of uncoated nanoparticles (UNP), CNP, CNP-ITEM4 (low), and CNP-ITEM4 (high) to mouse brain ECM chip (FIG. 15A) and an expanded view of the boxed region in FIG. 15A (FIG. 15B).
Figure 15B:
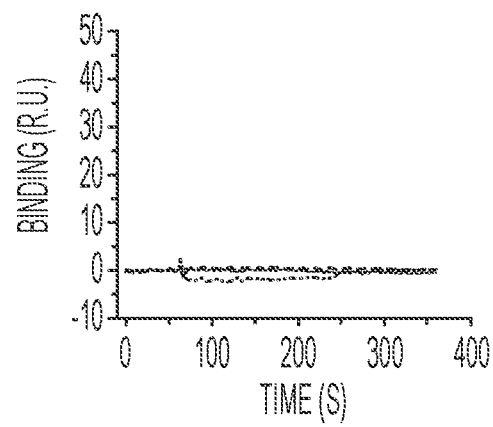

Example 14. Biacore™ Screening of Nanoparticles for Non-Specific Binding to Brain ECM Proteins To screen nanoparticles for non-specific binding to brain ECM, mouse brain ECM components were functionalized to the surface of a Biacore™ chip and the binding of various nanoparticle formulations was evaluated. As a positive control, the non-specific binding of uncoated nanoparticles (UNP) was measured, as these particles have been shown previously to be nearly completely immobilized when delivered into the rodent brain. UNP bound strongly to the surface of the ECM Biacore™ chip (FIG. 15A and FIG. 15B), and these particles did not appreciably desorb from the chip with standard Biacore™ regeneration procedures. Thus, a freshly prepared ECM Biacore™ chip was used for the remainder of the experiments. None of the CNP formulations that we studied (CNP, CNP-ITEM4 (low) and CNP-ITEM4 (high)) bound appreciably to the ECM chip, suggesting minimal non-specific interactions between the nanoparticles and the brain ECM proteins.

Example 15. Nanoparticle Uptake in Fn14-Negative and Fn14-Positive Cells

Figure 16A:
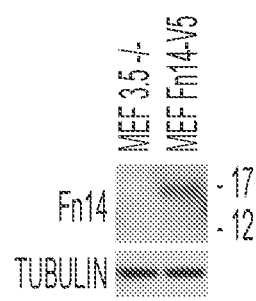
FIG. 16A is a western blot image of Fn14 expression in Fn14-negative and Fn13 lentivirus infected (V5) murine embryonic fibroblast ("MEF") cell lines.
Figure 16B:
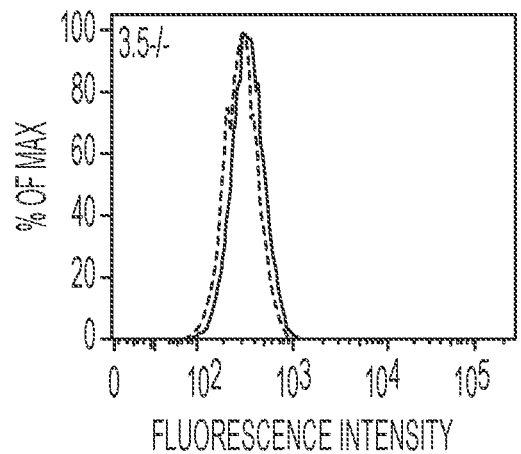
FIG. 16B presents FACS data showing Fn14 expression in the two cell lines.
Figure 16C:
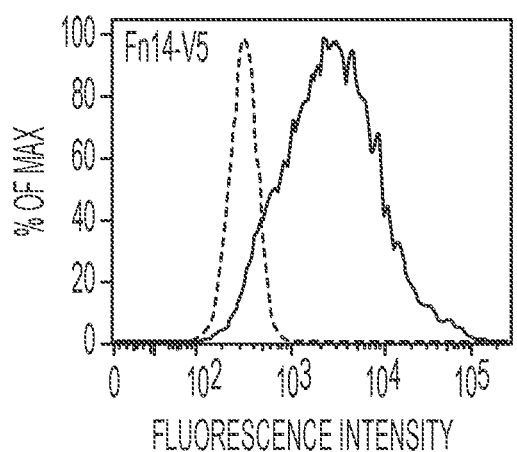
FIG. 16C is a graph illustrating CNP and CNP-ITEM4 nanoparticle uptake in the two cell lines.
Figure 16D:
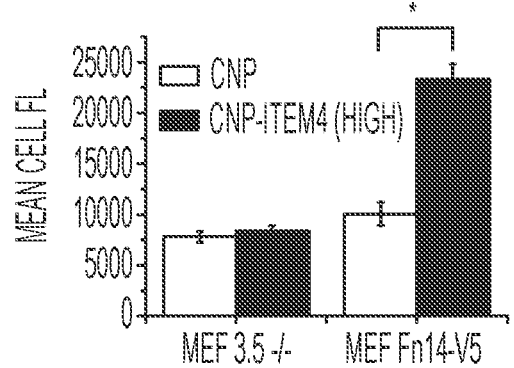
FIG. 16D is a bar graph showing mean cell fluorescence in CNP and CNP-ITEM4.

To confirm CNP-ITEM4 nanoparticle binding results from the Biacore™ assay, the cellular uptake of the CNP formulations was measured via flow cytometry. First, the uptake of CNP-ITEM4 was measured with two mouse embryonic fibroblast (MEF) cell lines: MEF 3.5 7- and MEF Fn14-V5. The MEF 3.5 7-cells were generated from Fn14-null mice and therefore do not express Fn14, as assayed by either western blot analysis (FIG. 16A) or flow cytometry (FIG. 16B). MEF Fn14-V5 cells were produced via infection of the MEF 3.5 7-cell line with a lentivirus encoding human Fn14. Fn14 expression in these cells was confirmed by western blot and flow cytometry assays (FIG. 16A and FIG. 16B). CNP-rfEM4 nanoparticle uptake by the MEF cell lines was determined via flow cytometry. There was no difference in cellular uptake between CNP and CNP-ITEM4 (high) in MEF 3.57-cells. In contrast, CNP-rfEM4 (high) uptake was about 2.5-fold greater than CNP uptake when these nanoparticles were added to the MEF Fn14-V5 cells (FIG. 16C).

Second, nanoparticle uptake was examined in human U87-Luc/GFP GBM cells. These cells express Fn14, as measured by western blotting (data not shown) and flow cytometry (FIG. 17A). A statistically significant increase in CNP uptake was observed in these cells with increasing ITEM4 density (FIG. 17B). Specifically, the cellular uptake efficiency of CNP-ITEM4 (low) and CNP-ITEM4 (high) was about 1.25-fold and about 3.5-fold higher, respectively, compared to CNP alone. To test whether the enhanced CNP-ITEM4 uptake was the result of a specific interaction between ITEM4 and Fn14, a competitive inhibition assay with free ITEM4 antibody was performed. Addition of excess free ITEM4 to cells, prior to particle addition, significantly inhibited the uptake of CNP-ITEM4 (high) to the same levels as that observed for non-targeted CNP (FIG. 17C). In contrast, no inhibition of CNP-ITEM4 uptake was observed when the same amount of IgG isotype control protein was preincubated with U87-Luc/GFP cells. To confirm that CNP-ITEM4 nanoparticles were internalized within cells and not solely associated with Fn14 on the cell surface, live-cell confocal microscopy imaging was performed (see FIG. 17D, FIG. 17E, FIG. 17F, and FIG. 17G). Intracellular localization of CNP-ITEM4 was confirmed via z-stack analysis of cells stained with Hoechst 34580 (FIG. 17G).

Example 16. Nanoparticle Transport in Brain Tissue

Figure 18A:
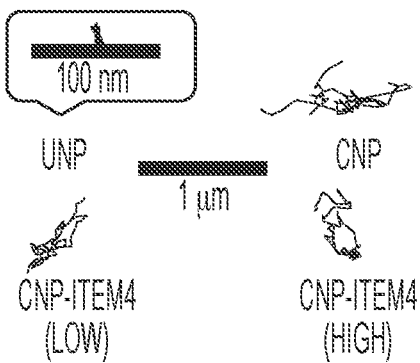
FIG. 18A is a drawing illustrating transport of uncoated nanoparticles (UNP), CNP, CNP-rfEM4 (low), and CNP-ITEM4 (high) nanoparticles in rat brain slices.
Figure 18B:
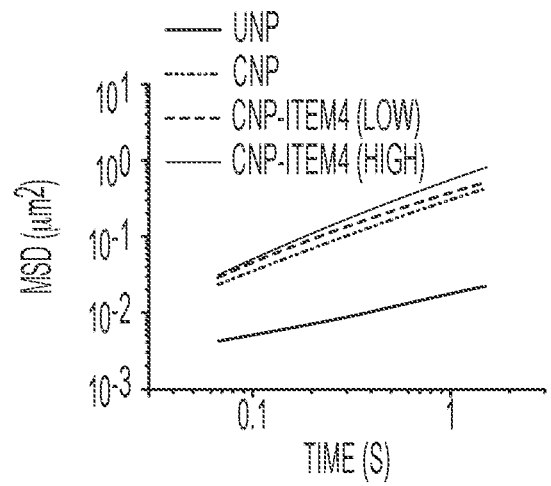
FIG. 18B and FIG. 18C are graphs that show transport measured by MPT analysis.
Figure 18C:
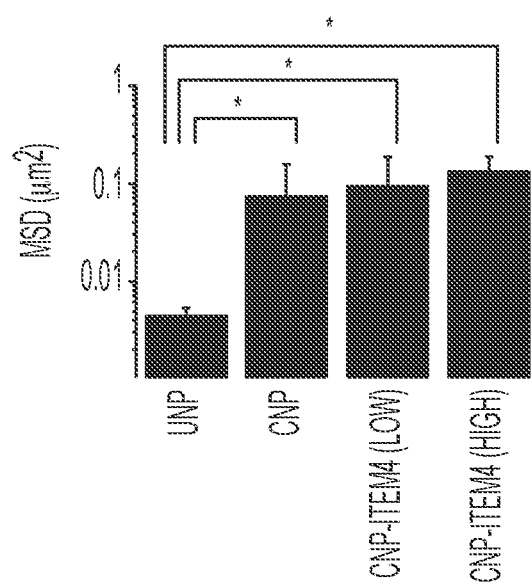
Figure 19:
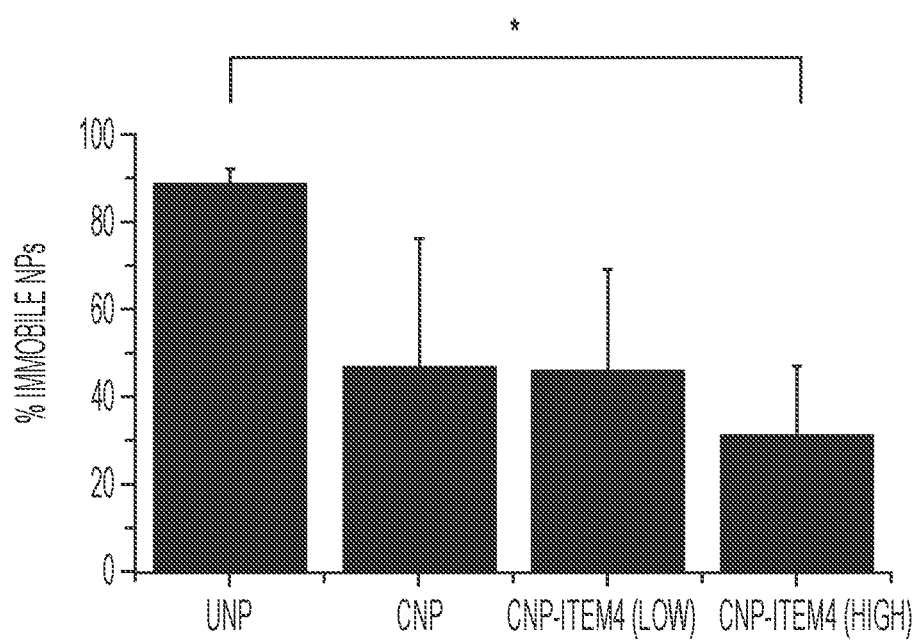
FIG. 19 is a graph illustrating MPT analysis of uncoated nanoparticles (UNP), CNP, CNP-ITEM4 (low), and CNP-ITEM4 (high) nanoparticles in rat brain slices.

MPT was used to test the diffusion rates of individual nanoparticles in ex vivo rat brain slices. Representative trajectories of nanoparticles are shown in FIG. 18A, from which it is clear that UNP were immobilized in brain tissue. In contrast, all three CNP formulations tested, CNP, CNP- ITEM4 (low) and CNP-ITEM4 (high), exhibited more diffusive Brownian-like trajectories. This can be quantitatively observed by the upward shift in the MSD vs time scale ($\tau$) curve for CNP, CNP-ITEM4 (low) and CNP-ITEM4 (high) compared to UNP (FIG. 18B). The calculated MSD at a time scale ($\tau$)=1 s for CNP formulations were more than an order of magnitude greater than UNP (FIG. 18C). The difference in the calculated MSD (at $\tau$=1) between UNP and all CNP formulations was statistically significant; however, there was no statistical difference between CNP, CNP-ITEM4 (low) and CNP-ITEM4 (high). The number of immobilized particles was estimated for each of the nanoparticle formulations based on the MPT transport data (FIG. 19).

The percentage of particles were classified as immobilized if the displayed MSD values at a time scale ($\tau$) of 1 second were less than the MSD for a particle that has moved one particle diameter from its initial position. Nearly ~90% of UNP were effectively immobilized in brain tissue, whereas only 25% to 45% of CNP were immobile depending on the formulation; however, a statistically significant difference was only observed between UNP and CNP-ITEM4 (high).

Figure 20A:
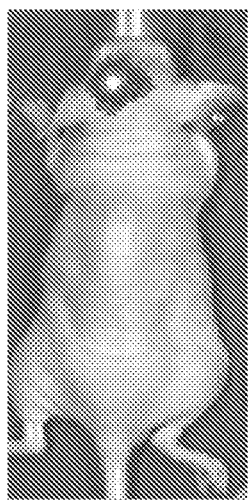
FIG. 20A and FIG. 20B are photographs illustrating BLI signal from a mouse bearing intracranial U87-luciferase glioma tumor (FIG. 20A) and a fluorescent microscopy image of GFP-expressing U87 tumors (FIG. 20B).
Figure 20B:
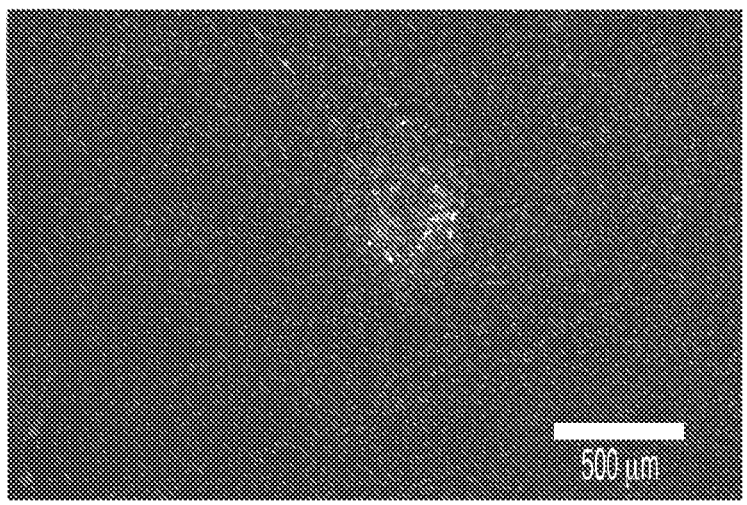
Figure 21A:
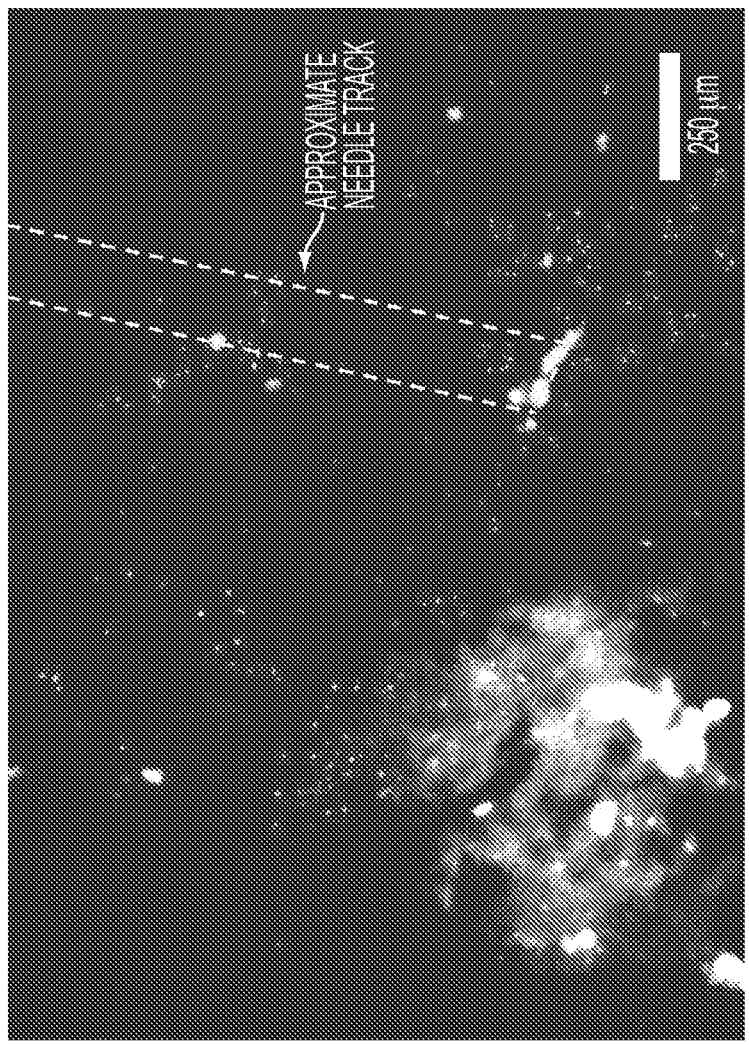
FIG. 21A, FIG. 21B, FIG. 21C and FIG. 21D are photographs illustrating in vivo distribution of untargeted CNPs (FIG. 21A), CNP-ITEM4 nanoparticles (FIG. 21B), GFP-expressing U87 cells (FIG. 21C), and a merged image of FIG. 21B and FIG. 21C 24 hours following intracranial injection of particles at the similar stereotactic coordinates as the U87-Luc/GFP cell tumor implantation (FIG. 21D).
Figure 21B:
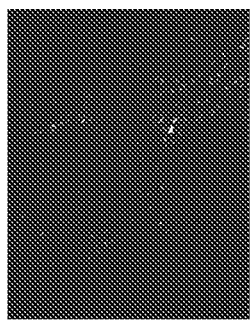
Figure 21C:
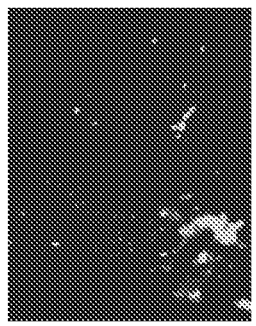
Figure 21D:
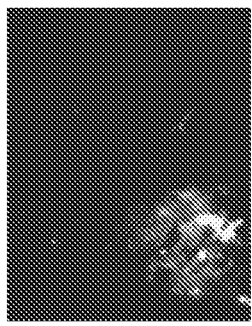

Example 17. Nanoparticle Distribution Following Intracranial Administration into Human GBM Xenografts To test the performance of Fn14-targeted nanoparticles in vivo, fluorescent nanoparticles (CNP and CNP-ITEM4 (high)) were administered to athymic nude mice bearing orthotopic U87-Luc/GFP GBM tumors. Luciferase- and GFP-expressing U87 tumor cells were evident in the brain 7 days after tumor implantation (see FIG. 20A and FIG. 20B). CNP and CNP-ITEM4 (high) nanoparticles were co-injected at the same stereotactic coordinates that were used for the tumor cell implantation. The mice were euthanized at 24 hours after nanoparticle injection and brains were isolated. Cryosections were prepared and imaging conducted to assess tissue distribution of the nanoparticles and co-localization with the GFP-expressing brain tumor cells (see FIG. 21A, FIG. 21B, FIG. 21C, and FIG. 21D). CNP and CNP-ITEM4 (high) nanoparticles were both distributed uniformly in the brain, however, a greater association of CNP-ITEM4 (high) was found with GFP-expressing tumor cells compared to untargeted CNP (FIG. 21D). These results demonstrate that our CNP-ITEM4 can penetrate within brain tissue and selectively target remote experimental GBM tumors.

Example 18. Fn14 is Highly Expressed in TNBC

Figures 22A, 22B, 22C, 22D:
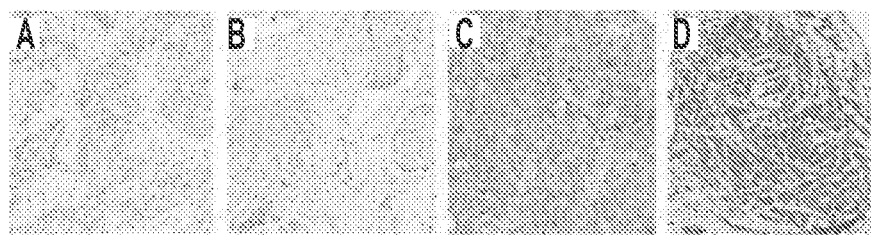
FIG. 22A, FIG. 22B, FIG. 22C and FIG. 22D are photographs of triple-negative breast tumor samples, stained for Fn14 expression, showing low to high Fn14 levels (left to right).

IHC analysis of Fn14 expression in a breast tumor tissue microarray is shown in FIG. 22. TNBC tumor specimens exhibiting Fn14 mAb staining (red color) scores of 0-3 are shown in FIG. 22A, FIG. 22B, FIG. 22C, and FIG. 22D, respectively.

Figure 23:
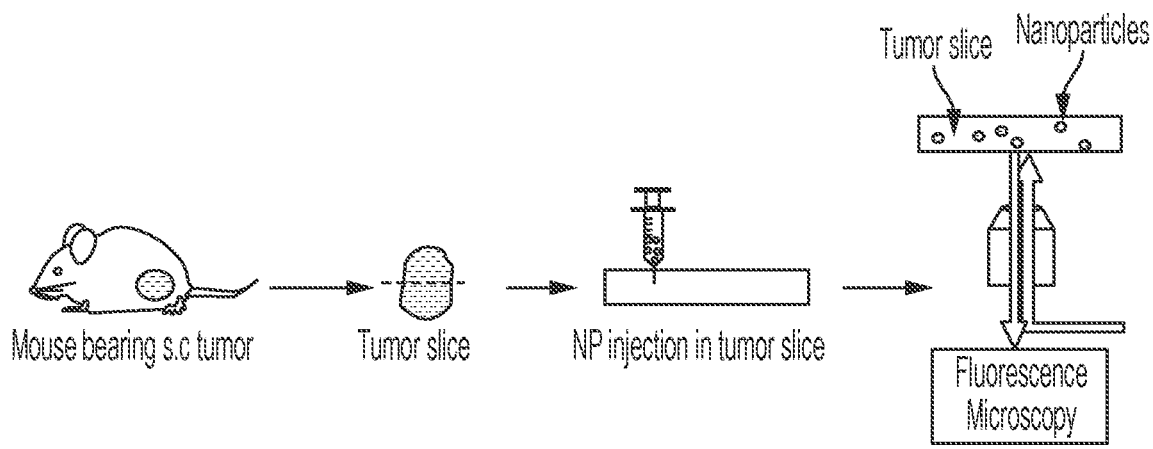
FIG. 23 is a flow chart showing methods used for ex vivo tumor testing of nanoparticle diffusion by MPT analysis.

Example 19. Multiple Particle Tracking (MPT) Analysis of NP Diffusion in Tumor Tissue Ex Vivo Using polystyrene (PS) particles over the size range of 20-100 nm, how particle size impacted NP diffusion was tested, in a tumor ECM preparation (Matrigel™) and in triple-negative breast cancer (TNBC) xenografts, by multiple particle tracking (MPT) (see FIG. 23) and intravital microscopy. Nonspecific binding of the NPs to tumor ECM was determined by a surface plasmon resonance (SPR) binding assay, which was then compared to the NP diffusion results. Biodegradable paclitaxel-loaded poly(lactic-co-glycolic acid)-poly(ethylene glycol) (PLGA-PEG) NPs were formulated and conjugated with an antibody specific to Fn14, a cell surface receptor expressed in TNBC. The diffusion of the PLGA-PEG NPs in tumor slices ex vivo was evaluated. Their specific and non-specific binding to Fn14-coated and tumor ECM proteins-coated surfaces, respectively, also was investigated by SPR. Finally, tumor cell targeting of these NPs was evaluated in vitro and in vivo using MDA-MB-231 TNBC cells.

FIG. 24A and FIG. 24B shows data from the multiple particle tracking (MPT) analysis of NP diffusion in tumor tissue ex vivo. Diffusion of individual fluorescent polystyrene (PS) NPs in ex vivo MDA-MB-231 tumor tissue was quantitated using MPT. FIG. 24A is a diagram of 20, 40, and 100 nm fluorescent PS NPs that were either left uncoated (UNP) or were coated with PEG (CNP) for MPT studies. FIG. 24B shows the ensemble-averaged mean square displacement (MSD) of 20, 40, and 100 nm UNPs and CNPs at a time scale of 1 second in tumor slices.

Example 20. Nanoparticle Penetration of Breast Tumor Tissue In Vivo

Green CNPs and red UNPs were co-injected into MDA-MB-231 flank tumors at a depth of 100-200 μm. Particle penetration within the tumor was assessed by 2-photon confocal microscopy. Images were acquired within 10 minutes after injection. See FIG. 25A, FIG. 25B, and FIG. 25C. Arrows indicate the approximate position of the injection needle. Scale bar is 500 μm. FIG. 25C is a merged image.

Example 21. SPR and MPT Analyses of Biodegradable NPs in Tumor Tissue ECM

Figure 26A:
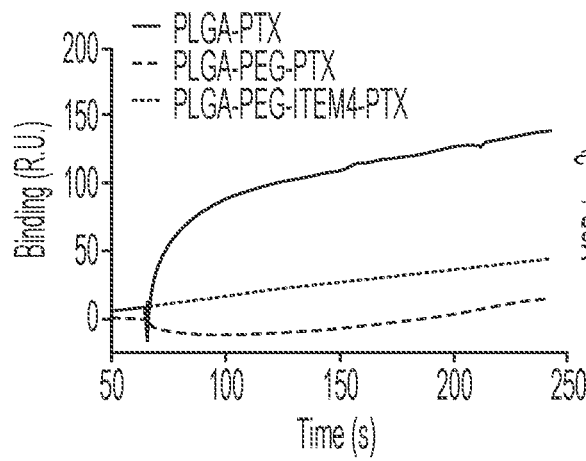
FIG. 26A is a graph showing SPR analysis of binding of Fn14-targeted and non-targeted PTX-loaded nanoparticles to a Matrigel™ chip, simulating ECM.

SPR analysis was performed to measure non-specific binding of paclitaxel-loaded PLGA (non-targeted), PEG-PLGA (non-targeted), and PLGA-PEG-ITEM4 (targeted) NPs to a Matrigel™ chip. NPs were conjugated with or without the monoclonal antibody ITEM4 to detect any differences in targeted versus non-targeted nanoparticles. See FIG. 26A.

Figure 26B:
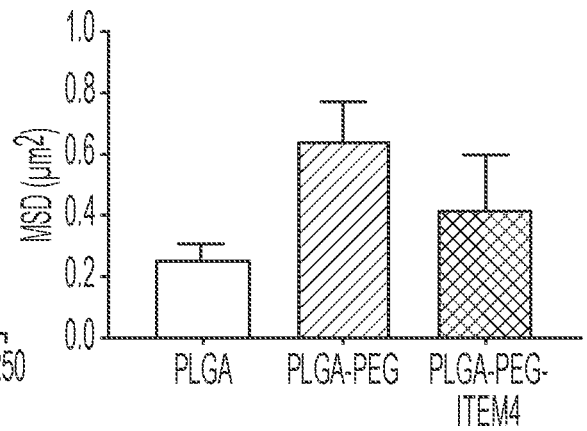
FIG. 26B is a graph presenting data for diffusion of individual fluorescent PLGA nanoparticles in MDA-MB-231 tumor slices.

Diffusion of individual fluorescent PLGA NPs in MDA-MB-231 tumor tissue was quantitated using MPT ensemble-averaged MSD of NPs in tumor slices, at a time scale of 1 second. See FIG. 26B.

Figure 27A:
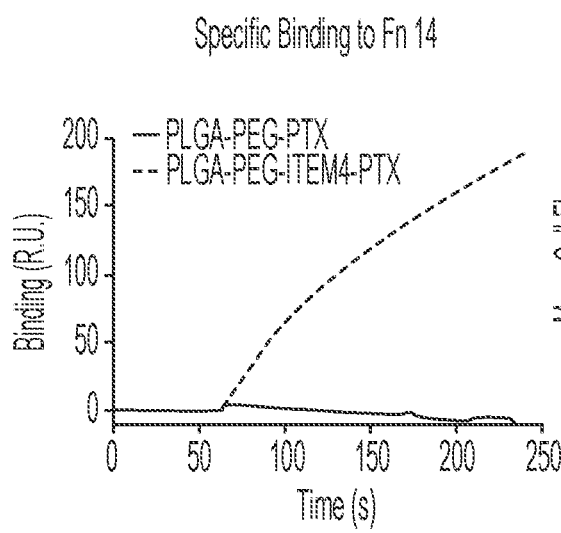
FIG. 27A and FIG. 27B are graphs showing specific binding of Fn14-targeted and non-targeted PTX-loaded nanoparticles to recombinant Fn14-extracellular domain on an SPR chip and uptake of the nanoparticles by MDA-MB-231 cells, respectively.
Figure 27B:
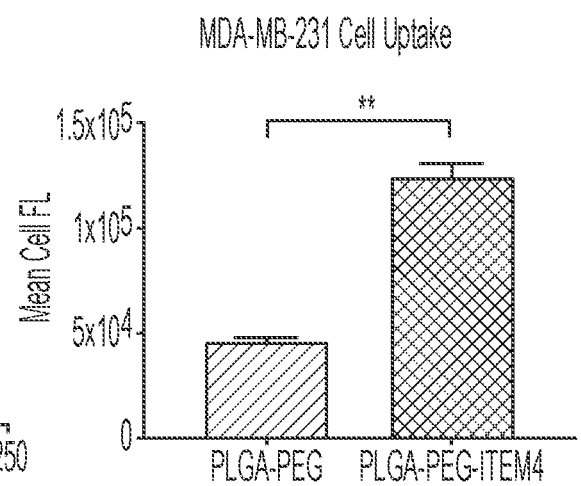

Example 22. Specific Binding Analyses of Non-Targeted and Fn14-Targeted Biodegradable Nanoparticles SPR analysis was used to measure the specific binding of PTX-loaded NPs to the Fn14-extracellular domain. NPs were conjugated with or without the Fn14-specific monoclonal antibody ITEM4. See FIG. 27A. The uptake of fluorescent NPs by Fn14+ MDA-MB-231 cells is shown in FIG. 27B.

Figures 28A, 28B, 28C, 28D:
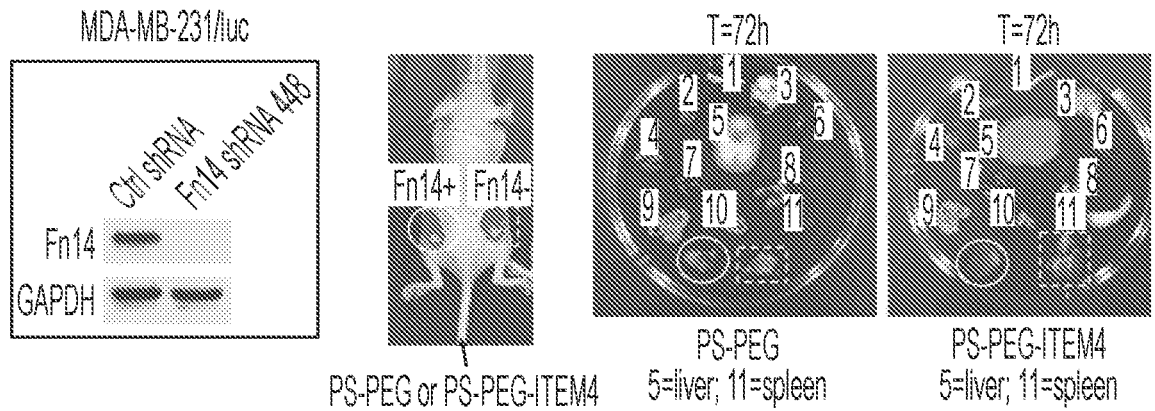
FIG. 28A is a western blot showing Fn14 expression in Fn14⁺ or Fn14⁻ MDA-MB-231 cells.
FIG. 28B is a photograph showing a nude mouse into which Fn14⁺ or Fn14⁻MDA-MB-231/Luc cells were implanted. Fluorescent ITEM4-conjugated NPs were injected via the tail vein.
FIG. 28C and FIG. 28D are photographs of organs and tumors, isolated after 72 hours and analyzed using a Xenogen™ system. Note preferential accumulation of targeted NPs in the Fn14-positive tumor.

Example 23. Biodistribution of NPs in Fn14-Positive and Fn14-Negative Triple Negative Breast Cancer (TNBC) Tumors MDA-MB-231 breast cancer cells engineered to express luciferase were infected with lentiviral vectors encoding either control (Ctrl) non-silencing shRNA or Fn14 shRNA 448. Western blot analysis confirmed Fn14-knockdown (see FIG. 28A). The Fn14-positive or Fn14-negative MDA-MB- 231/Luc cells were implanted in a nude mouse (see FIG. 28B). Fluorescent ITEM4-conjugated NPs were injected via the tail vein. Organs and tumors were isolated after 72 hours and analyzed using a Xenogen™ system. Note preferential accumulation of targeted NPs in the Fn14-positive tumors.

Figures 29A, 29B:
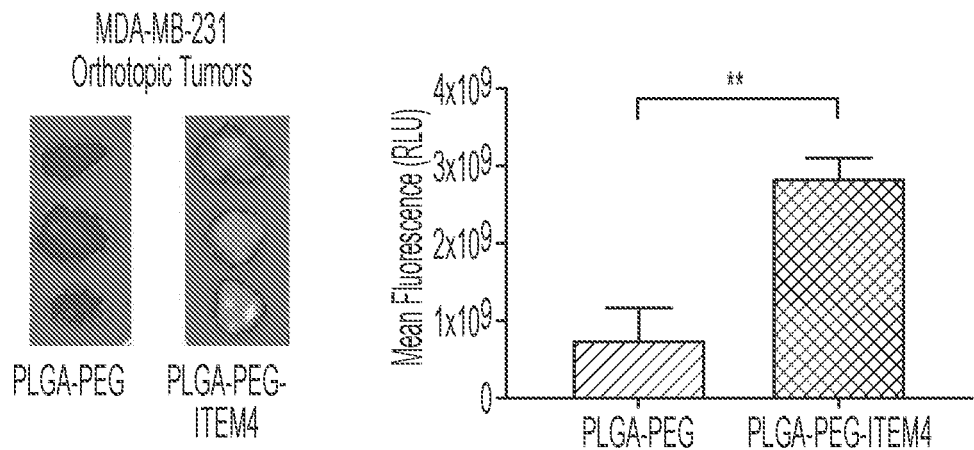
FIG. 29A and FIG. 29B are graphs showing distribution of non-targeted and Fn14-targeted fluorescent nanoparticles after tail vein injection into breast-tumor bearing mice (FIG. 29A) and quantitation of the tumor fluorescence from these data (FIG. 29B).

Example 24. Preferential Accumulation of Targeted NPs in Fn14-Positive TNBC Tumors MDA-MB-231 cells were implanted into the mammary fat pad of nude mice. Fluorescent NPs with and without ITEM4 conjugation were injected via the tail vein. Tumors were isolated after 24 hours and visualized. See FIG. 29A. Quantification of the tumor fluorescence from panel A is shown in FIG. 29B.

Example 25. Drug-Loaded Nanoparticles

Figure 30A:
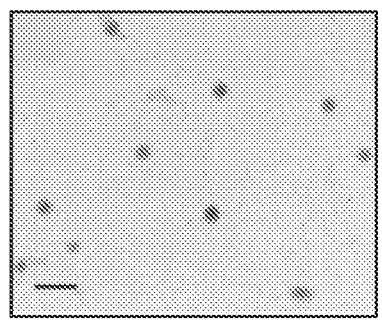
FIG. 30A is a transmission electron microscopy image of drug-loaded biodegradable nanoparticles. Scale bar=200 nm.
Figure 30B:
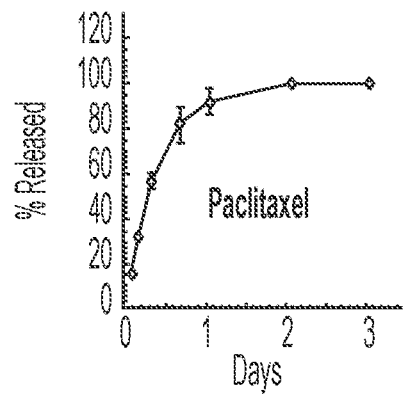
FIG. 30B shows drug release data of PTX loaded into biodegradable PLGA nanoparticles monitored over time.

Drug-loaded biodegradable nanoparticles were imaged using transmission electron microscopy. See FIG. 30A; scale bar=200 nm. PTX was loaded into biodegradable PLGA nanoparticles. FIG. 30B shows release of the drug over time at 37° C. using the dialysis method.

Figure 31A:
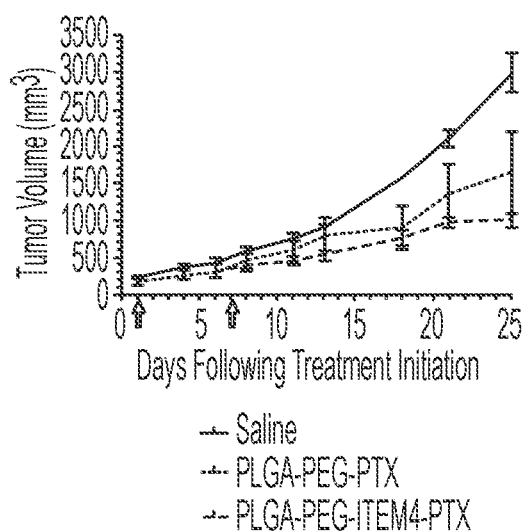
FIG. 31A and FIG. 31B show the average tumor growth (in vivo efficacy in the orthotopic TNBC tumor model) of mice following administration of saline or PTX-loaded PLGA-PEG and PLGA-PEG-ITEM4 nanoparticles (FIG. 31A) and survival comparisons between groups, analyzed by the Kaplan-Meier method (FIG. 31B).
Figure 31B:
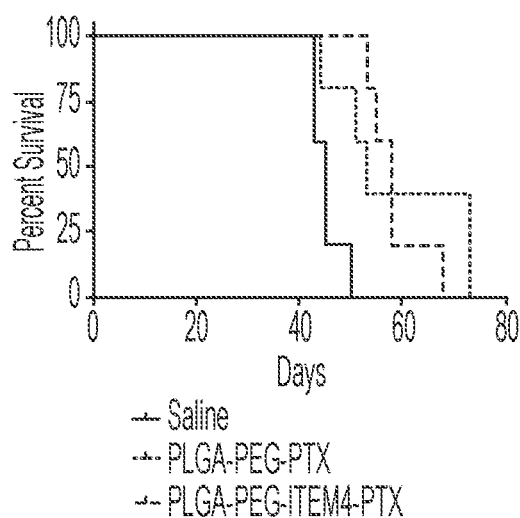

Example 26. Effect of Paclitaxel-Loaded Nanoparticles on Primary TNBC Tumor Growth Saline (control), or PTX-loaded PLGA-PEG and PLGA-PEG-ITEM4 nanoparticles were tested for efficacy in an orthotopic TNBC tumor model. Two and seven days after systemic administration, data was collected. See FIG. 31A, which shows the average tumor growth of mice in each group (n=5 mice per group). Tumor volume was monitored every 2 days by caliper measurements. FIG. 31B presents survival comparisons between groups, analyzed by the Kaplan-Meier method and the log-rank test.

Example 27. Synthesis and Characterization of Nanoparticles with Different Surface Properties Biodegradable PLGA or PLGA-PEG polymeric nanoparticles were synthesized using single emulsion solvent evaporation technique. The hydrodynamic diameters of PLGA and PLGA-PEG nanoparticles were approximately 67 nm and approximately 75 nm, respectively. The PLGA-PEG nanoparticles were then conjugated with either ITEM4, an Fn14 monoclonal antibody (mAb), or the corresponding IgG isotype control protein. Maleimide-thiol chemistry was used, and resulted in PLGA-PEG-ITEM4 and PLGA-PEG-IgG nanoparticles, respectively. PLGA-PEG-IgG nanoparticles had hydrodynamic diameter of approximately 100 nm. For optimization experiments of DART characteristics, PLGA-PEG-ITEM4 nanoparticles were synthesized with varying PEG (1%, 5%, or 10% of total polymer mass) and ITEM4 (0.1%, 1%, or 10% of total polymer mass) densities. The hydrodynamic diameters of these particles varied between approximately 92 nm to approximately 97 nm (see Table 4, below).

The addition of the PEG and ITEM4 or IgG antibodies increased the size of PLGA nanoparticles by 20-25 nm with PLGA-PEG-IgG being approximately 100 nm and PLGA-PEG-ITEM4 being approximately 95 nm regardless of ITEM4 conjugation density (0.1, 1, or 10%) (see Table 5). All the formulations had ζ-potential values close to the neutral surface charge (~1 to −5 mV), due to the PEG coatings and/or use of poly vinyl alcohol (PVA) surfactants in the synthesis procedure (Tables 1 and 2). The number of PEG molecules on the nanoparticle surface was quantitated from nuclear magnetic resonance (NMR) data. Surface PEG density increased with the addition of more PEG molecules in the formulation, ranging from approximately 9, to approximately 19 PEG molecules per 100 $nm^2$ of nanoparticle surface (Tables 1 and 2). The number of ITEM4 and IgG molecules on the nanoparticle surface were estimated from the LavaPep™ protein assay. We found that there were about 4 IgG molecules per particle for PLGA-PEG-IgG and the number of ITEM4 molecules increased from about 2 to about 22 per particle with the addition of more ITEM4 molecules to the conjugation reaction (Tables 4 and 5). Physicochemical characterization data represent the average of 3 independent experiments+/−SD in both tables.

TABLE 4

Effect of PEG and ITEM4 Density on Properties of Fn14-targeted Nanoparticles.

| Formulation | Size (nm)[a] | PDI[b] | ζ-potential (mV)[c] | PEG density (#/100 $nm^2$)[d] | PEG conformation [Γ/Γ*][e] | mAb density (#/particle)[f] | $K_D$ (nM)[g] |
|---|---|---|---|---|---|---|---|
| PLGA-PEG$_{1\%}$-ITEM4$_{1\%}$ | 95.4 ± 5.3 | 0.14 ± 0.05 | −4.2 ± 0.3 | 9.2 | 2.0 | 6.1 | 3.2 |
| PLGA-PEG$_{5\%}$-ITEM4$_{1\%}$ | 93.2 ± 7.2 | 0.12 ± 0.02 | −4.6 ± 0.3 | 10.3 | 2.3 | 6.4 | 2.4 |
| PLGA-PEG$_{10\%}$-ITEM4$_{0.1\%}$ | 92.7 ± 5.4 | 0.10 ± 0.03 | −3.4 ± 0.2 | 13.4 | 2.1 | 1.7 | 26.5 |
| PLGA-PEG$_{10\%}$-ITEM4$_{1\%}$ | 94.8 ± 8.7 | 0.09 ± 0.04 | −3.1 ± 0.1 | 14.1 | 3.2 | 6.3 | 1.9 |
| PLGA-PEG$_{10\%}$-ITEM4$_{10\%}$ | 96.4 ± 5.6 | 0.12 ± 0.04 | −5.1 ± 0.4 | 13.7 | 2.9 | 21.8 | 2.6 |

[a]Hydrodynamic diameter (number mean) measured by dynamic light scattering (DLS); [b]Polydispersity index indicates the distribution of individual molecular masses in a batch of nanoparticles, measured by DLS; [c]Surface charge measured at 25° C. in 15x diluted PBS with ~9 mM NaCl, pH 7.4; [d]PEG surface density determined by NMR; [e]PEG surface coverage/total surface area (value <1 indicates mushroom coverage [low density], whereas ≥1 indicates brush regime [high density]); [f]Surface density reported from LavaPep™ fluorescent protein assay; [g]Equilibrium binding affinity (KD) values determined on a per nanoparticle basis from fit of Fn14-binding Biacore™ data.

TABLE 5

Properties of PTX-loaded nanoparticles.

| Formulation | Size (nm)[a] | PDI[b] | ζ-potential (mV)[c] | Drug loading (%)[d] | PEG density (#/100 nm²)[e] | PEG conformation [Γ/Γ*][f] | mAb density (#/particle)[g] | $MSD_{water}/MSD_{tumor}$[h] |
|---|---|---|---|---|---|---|---|---|
| PLGA | 66.9 ± 5.5 | 0.16 ± 0.02 | −4.3 ± 0.4 | 5.7 ± 1.2 | — | — | — | 124 |
| PLGA-PEG | 75.4 ± 5.1 | 0.03 ± 0.01 | −1.4 ± 0.5 | 7.7 ± 1.0 | 13.0 | 2.9 | — | 17 |
| PLGA-PEG-IgG | 99.7 ± 12.8 | 0.18 ± 0.05 | −4.8 ± 0.4 | 8.2 ± 0.6 | 19.5 | 4.4 | 4.2 | — |
| PLGA-PEG-ITEM4 | 94.8 ± 8.7 | 0.09 ± 0.04 | −3.1 ± 0.1 | 8.7 ± 0.2 | 14.1 | 3.2 | 6.3 | 15 |
| Abraxane ™ | 143.1 ± 4.6 | 0.11 ± 0.01 | −13.5 ± 1.3 | 10 | — | — | — | — |

[a]Hydrodynamic diameter (number mean) measured by dynamic light scattering (DLS); [b]Polydispersity index indicates the distribution of individual molecular masses in a batch of nanoparticles, measured by DLS; [c]Surface charge measured at 25° C. in 15x diluted PBS with ~9 mM NaCl, pH 7.4; [d]Drug loading is the percentage of PTX encapsulated into nanoparticles (% w/w); [e]PEG surface density determined by NMR; [f]PEG surface coverage/total surface area (value <1 indicates mushroom coverage [low density], whereas >1 indicates brush regime [high density]); [g]Surface density reported from LavaPep ™ fluorescent protein assay; [h]Ratio indicates the extent to which diffusion of nanoparticles in breast tumor tissues is reduced compared to their diffusion in water.

Example 28. Specific Binding of Nanoparticle Formulations to the Fn14 Extracellular Domain and Analysis of Nanoparticle Binding to Fn14 Using SPR Assays The binding of different nanoparticle formulations to immobilized Fn14 was assessed using SPR assays. The Fn14 extracellular domain was first conjugated to the surface of a Biacore™ chip. As a positive control for chip quality, ITEM4 mAb, but not control murine IgG, was demonstrated to bind strongly to the Fn14 chip surface, confirming adequate SPR chip preparation (FIG. 32A).

In order to optimize the nanoparticle formulation, the binding of PLGA-PEG-ITEM4 with varying densities of PEG and ITEM4 was analyzed with respect to the Fn14 chip. To determine the equilibrium binding affinity of each nanoparticle formulation, the kinetics of binding was measured using a nanoparticle concentration gradient (FIG. 33). Equilibrium binding (RUeq) values then were obtained and plotted against nanoparticle concentration to calculate binding isotherms. The equilibrium binding affinity (KD) then was calculated by fitting the binding isotherm data to a 'one site specific binding' model equation.

The KD values for nanoparticles with varying PEG density (1%, 5%, and 10%) at constant 1% ITEM4 density were similar (3.2, 2.4, and 1.9 nM, respectively; FIG. 33; Table 4). The measured KD for nanoparticles with varying ITEM4 density at constant 10% PEG density ranged from 26.5 nM for 0.1% ITEM4 to 2.6 nM for 10% ITEM4 (FIG. 33, Table 4). FIG. 33 shows data for schematic representation and kinetic binding analysis of PLGA-PEG1%-ITEM41% (FIG. 33A), PLGA-PEG5%-ITEM41% (FIG. 33B), PLGA-PEG10%-ITEM40.1% (FIG. 33C), PLGA-PEG10%-ITEM41% (FIG. 33D), and PLGA-PEG10%-ITEM410% (FIG. 33E) nanoparticles to an Fn14-coated Biacore™ chip showing binding curves at various concentrations using surface plasmon resonance (SPR) technique (R.U.: Response Units). These curves were fit to a 35 first order process to determine RUeq values at each concentration. Binding isotherms of these nanoparticles showing RUeq values were determined from their respective kinetic binding analysis. The data were fit to a single class of binding sites by non-linear regression analysis using GraphPad™ software (A.U.: Arbitrary Units).

The Fn14-specific binding of ITEM4 mAb, a fragment antigen-binding (Fab) portion of ITEM4, a single-chain variable fragment (scFv) of ITEM4, and a reported D-enantiomeric peptide ligand of Fn14, as well as their nanoparticle counterparts, were examined. The ITEM4 mAb and PLGA-PEG-ITEM4 mAb bound strongly to the Fn14 chip (FIG. 32B). Similarly, the ITEM4 Fab and PLGA-PEG-ITEM4 Fab showed appreciable binding to the Fn14 chip (FIG. 32C). However, this binding was significantly less than their full mAb counterparts. Further, the ITEM4 scFv showed relatively weak binding to the Fn14 chip, whereas PLGA-PEG-ITEM4 scFv showed no significant binding (FIG. 32D). Finally, there was no Fn14 binding observed with the reported Fn14 peptide ligand or the corresponding PLGA-PEG-Fn14 peptide nanoformulation (FIG. 32E).

Example 29. Nanoparticle Surface Properties Alter their Systemic Circulation Time and Tumor Accumulation Near infrared (NIR)-labeled polystyrene (PS) nanoparticles were used in lieu of PLGA nanoparticles for initial blood circulation experiments, since these particles are more easily detected in the Xenogen™ whole-body fluorescence imaging system. The blood circulation time of PS nanoparticles with either no PEG coating or conjugated with comparable surface PEG densities were compared to their PLGA nanoparticle counterparts (noted as 1%, 5%, or 10% PS-PEG). The PS-PEG formulation containing the highest PEG density (10%) displayed the longest blood circulation time (see FIG. 34A). In contrast, PS or PS-PEG with 1% and 5% PEG density accumulated in the liver and spleen, indicating that without sufficient PEG coating, these particles are rapidly cleared from the circulation.

Next, to determine if conjugation of ITEM4 or IgG to the nanoparticle surface affects their systemic circulation, the blood circulation time of PS-PEG-ITEM4 and PS-PEG-IgG were evaluated. Conjugation of 1% ITEM4 or 1% IgG to the surface of PS with 10% PEG did not significantly reduce the circulation time of these particles (see FIG. 34B).

Liver accumulation of non-targeted biodegradable rhodamine-labeled PLGA nanoparticles with 1% or 10% PEG density then was compared. We removed and imaged livers from animals at 24 hours post-nanoparticle administration and found that PLGA with 10% PEG displayed minimal liver accumulation, indicative of a longer systemic circulation time compared to the PLGA with 1% PEG (see FIG. 34C).

In summary, FIG. 34A shows the distribution of PBS, NIR dye-labeled PS and PEG-coated PS nanoparticles at 24 hours after systemic administration into mice as determined using Xenogen™ imaging system. FIG. 34B shows the distribution of PBS, NIR dye-labeled PS, PS-PEG, and IgG- or ITEM4-conjugated PS-PEG nanoparticles after systemic administration into mice as determined using Xenogen™ imaging system. FIG. 34C shows the liver accumulation of NIR dye-labeled PLGA-PEG nanoparticles with 1% PEG or 10% PEG density at 24 hours after systemic administration.

Figure 35C:
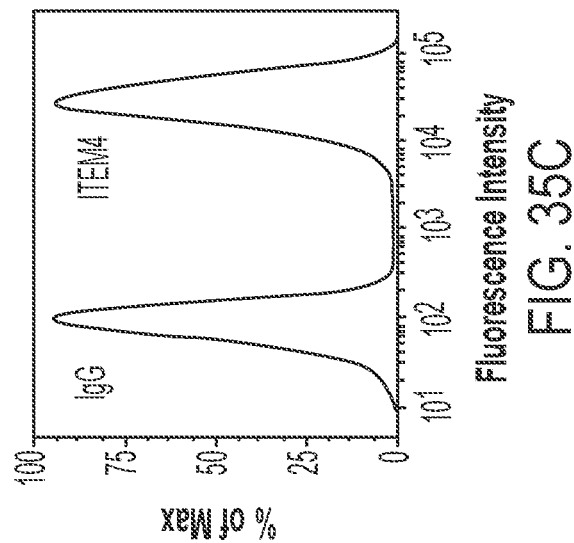
FIG. 35B and FIG. 35C show flow cytometry analysis of 231-Luc cells and 231-Br-Luc cells, respectively, for Fn14 surface expression with PE-labeled mouse IgG isotype control and ITEM4 antibody.
Figure 35B:
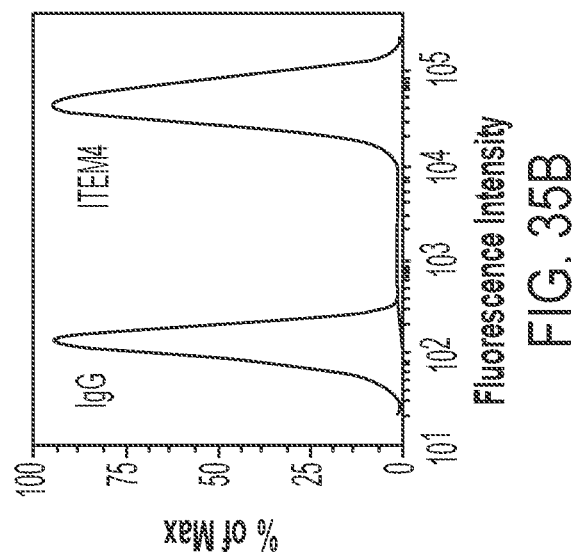
Figure 35A:
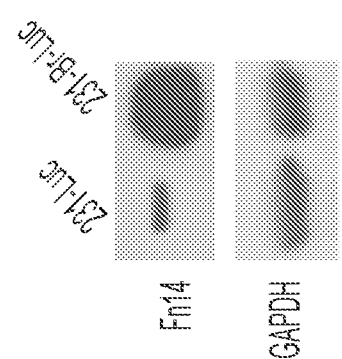
FIG. 35A is a western blot showing Fn14 and GAPDH expression in two triple-negative breast cancer cell line.

Next, the TNBC cell line MDA-MB-231-luc was injected into the mammary fat pad of mice. When tumors were established, the liver and tumor accumulation of rhodamine-labeled PLGA-PEG-ITEM4 nanoparticles was compared with constant 1% ITEM4, but varying PEG density (1%, 5%, or 10%). These 231-luc cells express Fn14, as determined by both western blot analysis (FIG. 35A) and flow cytometry (FIG. 35B).

Mice were euthanized 1 hour post-nanoparticle injection and livers were removed for fluorescence analysis using Xenogen™ imaging system. Nanoparticles with 10% PEG displayed minimal liver accumulation, indicative of a longer systemic circulation time compared to the nanoparticles with 1% and 5% PEG. See FIG. 36A (which presents a fluorescence image of livers from 231-Luc tumor-bearing mice isolated 1 hour after administration of rhodamine-labeled PLGA-PEG-ITEM41% with 1%, 5%, or 10% PEG density) and FIG. 36B (which shows analysis of fluorescence intensity from FIG. 36A. The same area of regions of interest (ROI) were used to obtain total radiance (photons/sec/cm2/sr) of the fluorescent signals. Values shown are mean±SD (n=3). There was no significant difference between groups (Student's t-test).

These results correlated well with tumor accumulation data where the same nanoparticles were injected into the tail vein of mice bearing similarly-sized 231-Luc mammary fat pad tumors. Mice were euthanized 24 hours post-nanoparticle injection and tumors were harvested for fluorescence analysis. Significantly higher tumor fluorescence was observed in mice that received nanoparticles with 10% PEG compared to mice that received nanoparticles with 1% or 5% PEG (see FIG. 36C and FIG. 36D). FIG. 36C is a fluorescence image of 231-Luc tumors isolated from mice 24 hours after administration of rhodamine-labeled PLGA-PEG-ITEM41% with 1%, 5%, or 10% PEG density; FIG. 36D shows analysis of fluorescence intensity from FIG. 36C. The data were obtained as for FIG. 36B. Values shown are mean±SD (n=3). Data were analyzed for significance using Student's t-test (**$P<0.01$).

To study the effect of ITEM4 surface density on nanoparticle circulation and clearance time, rhodamine-labeled PLGA-PEG-ITEM4 nanoparticles with constant 10% PEG but varying ITEM4 density (1% or 10%) were injected into non-tumor bearing mice via the tail vein. Mice were euthanized at 1 hour post-nanoparticle injection and the liver, spleen, and kidneys were removed for fluorescence analysis. No Fn14 expression was detected in these three organs by western blot analysis (see FIG. 37, which shows a western blot analysis of Fn14 and GAPDH levels in mouse CT-2A glioma cells (positive control), liver, spleen, and kidney samples). A significantly higher (~2.5-fold) accumulation of nanoparticles with 10% ITEM4 in spleens was observed compared to the nanoparticles with 1% ITEM4 (FIG. 36E and FIG. 36F). FIG. 36E is a fluorescence image of livers, spleens, and kidneys isolated from non-tumor bearing mice 1 hour after administration of rhodamine-labeled PLGA-PEG10%-ITEM4 with 1% or 10% ITEM4 density; FIG. 36F presents analysis of fluorescence intensity from FIG. 36E. These data were obtained as for FIG. 36B. The values shown are mean±SD (n=3). Data were analyzed for significance using Student's t-test (*$P<0.05$).

The liver and kidneys also exhibited nanoparticle accumulation; however, no significant difference was observed between 1% and 10% ITEM4 density nanoparticles. These results demonstrate that a 10% ITEM4 conjugation density may result in spleen toxicity; however, there was no significant difference observed in the various blood cell counts (WBC, WBC differential, RBC, HGB, etc.) and hepatic enzyme levels between the two groups (data not shown).

Example 30. Optimized Nanoparticles Bind to Fn14 after Serum Incubation, Preferentially Associate with Fn14-Positive 231-Luc Cells, and Exhibit Cytotoxicity In Vitro After establishing the optimal PEG and ITEM4 surface densities for DART nanoparticles (10% and 1%, respectively), PTX-loaded nanoparticles were prepared using a single emulsion solvent evaporation technique (Table 5). Nanoparticle analysis by transmission electron microscope (TEM) imaging showed round morphology and sub-100 nm size of PLGA-PEG and PLEG-PEG-ITEM4 (see FIG. 38A). PTX loading in nanoparticles varied from about 5.7% to about 8.7% (w/w) (Table 5). PLGA-PEG-IgG and PLGA-PEG-ITEM4 had 8.2% and 8.7% (w/w) PTX loading, respectively. The PTX release rate from both these formulations was similar (see FIG. 38B). The PTX release profiles followed a biphasic pattern, with approximately 50% release within 3 days and a sustained release in the following 20 days, reaching about 95%.

Fn14-specific binding of nanoparticles was assessed using SPR Biacore™ assay. PLGA-PEG-ITEM4 bound strongly to the Fn14 chip, however PLGA-PEG did not show any appreciable Fn14 binding (see FIG. 38C). In addition, SPR kinetic binding studies were performed after incubating the DART nanoparticle formulation with mouse blood serum to simulate the Fn14-specific binding ability of the nanoparticles after entering the systemic circulation. The nanoparticles maintained their Fn14 binding ability even in the presence of blood serum proteins (see FIG. 38D and FIG. 38E). The binding curves in FIG. 38D were fit to a first order process to determine $RU_{eq}$ values at each concentration. The measured KD of the DART nanoparticles after blood serum incubation was 6.1 nM.

The ability of fluorescent nanoparticle formulations to bind to 231-Luc cells was measured by flow cytometry. The cellular association efficiency of PLGA-PEG-ITEM4 was bout 2.5-fold higher than the core PLGA-PEG nanoparticle. See FIG. 39A, which presents data on flow cytometry analysis of PLGA-PEG and PLGA-PEG-ITEM4 nanoparticle association with 231-Luc cells.

Figure 39A:
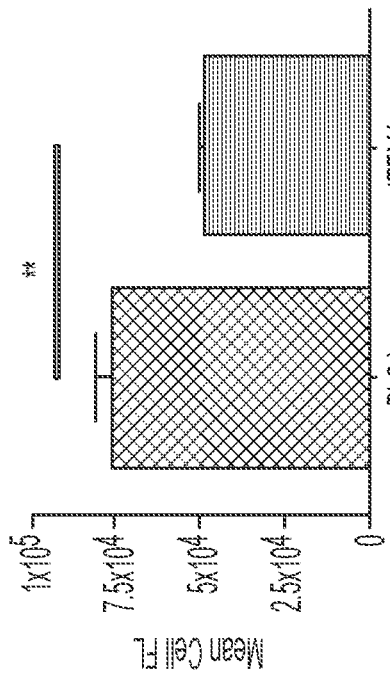
FIG. 39A provides flow cytometry analysis of fluorescent nanoparticle uptake by MDA-MB-231 cells.
Figure 39B:
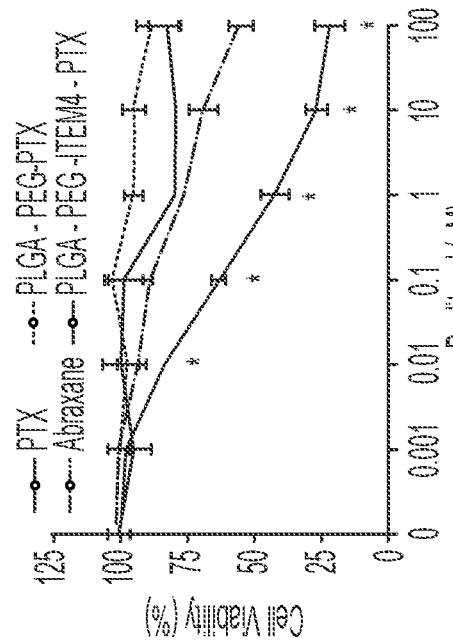
FIG. 39B shows inhibition of nanoparticle uptake/association after pre-incubation with free ITEM4.

To confirm whether the enhanced PLGA-PEG-ITEM4 uptake was the result of specific interaction between ITEM4 and Fn14, a competitive inhibition assay with free ITEM4 was performed. Incubation of cells with free ITEM4 before adding nanoparticles significantly inhibited the cellular association of PLGA-PEG-ITEM4. See FIG. 39B, which presents data regarding inhibition of nanoparticle uptake/association after pre-incubation of free ITEM4. In FIG. 39A and FIG. 39B, values shown are mean±SD (n=3). Data were analyzed for significance using Student's t-test (**$P<0.01$).

Figure 39C:
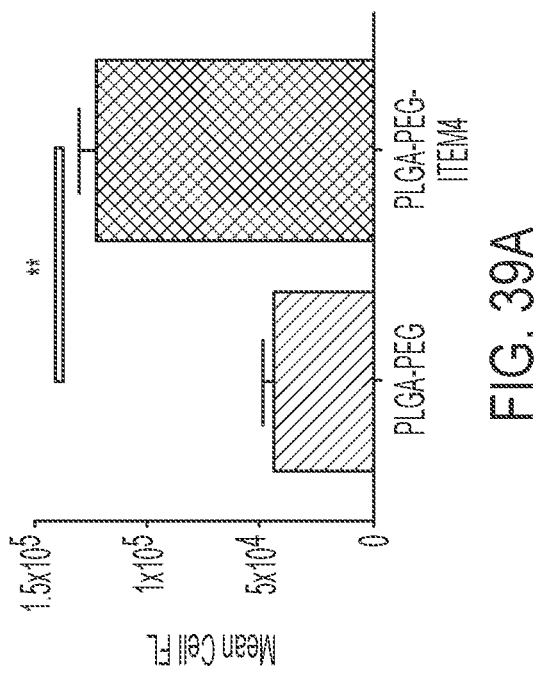
FIG. 39C shows confocal microscopy images of PLGA-PEG or PLGA-PEG-ITEM4 uptake by 231-Luc cells.

To examine nanoparticle internalization within the cells, live cell confocal microscopy was performed. Higher uptake of PLGA-PEG-ITEM4 by 231-Luc cells compared to PLGA-PEG was noted. See FIG. 39C, which provides confocal microscopy images of PLGA-PEG or PLGA-PEG-ITEM4 uptake by 231-Luc cells (scale bars=20 µm).

Figure 40:
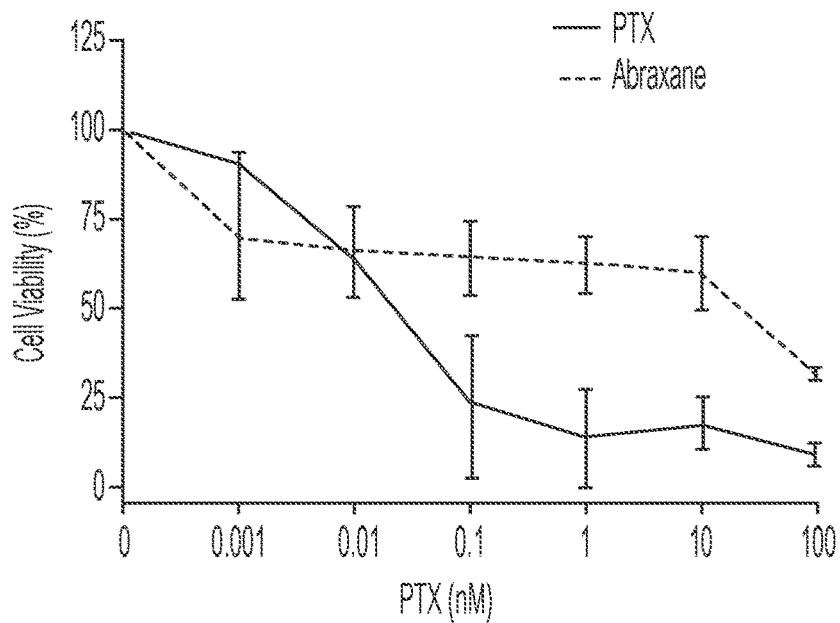
FIG. 40 shows the viability of 231-Luc cells determined by MTS assay after 24 hours of incubation with the indicated concentrations of free PTX or the same amount of PTX in the Abraxane™ formulation.

The relative cytotoxic effects of free PTX, PLGA-PEG-PTX, PLGA-PEG-ITEM4-PTX, and the FDA-approved PTX nanoformulation Abraxane™ on 231-Luc cells were determined by MTS assay. First, various doses of free PTX or Abraxane™ were added to the cells and left in the culture media for 24 hours. Both PTX and Abraxane™ were cytotoxic, but PTX was more potent than Abraxane™ (see FIG. 40). For FI2G. 41, the viability of 231-Luc cells was determined by MTS assay after 24 hours of incubation with the indicated concentrations of free PTX or the same amount of PTX in the Abraxane™ formulation.

Figure 39D:
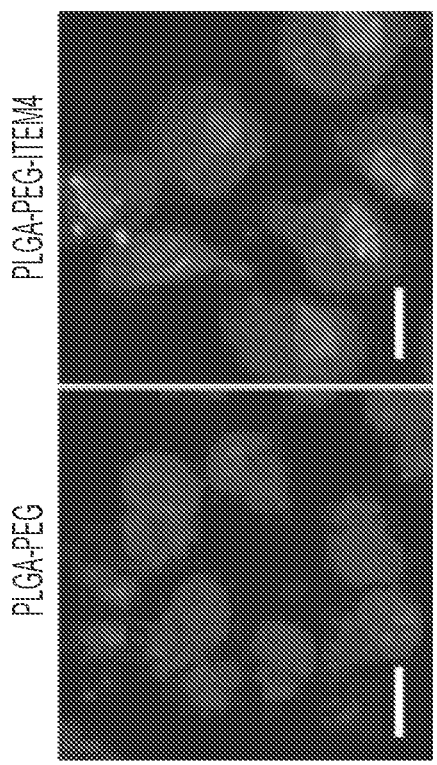
FIG. 39D presents data on the viability of 231-Luc cells determined by MTS assay after a 2-hour incubation with PTX, Abraxane™, PLGA-PEG-PTX, or PLGA-PEG-ITEM4-PTX.

Next, to examine the effect of a short drug exposure on these cells, which should mimic rapid drug clearance in vivo, free PTX, Abraxane™, PLGA-PEG-PTX, or PLGA-PEG-ITEM4-PTX nanoparticles were added to the cells and 2 hours later the culture media was removed and replaced with fresh media for 24 hours. Under these conditions, PTX and Abraxane™ showed only a small effect on cell viability. See FIG. 39D, which provides data on the viability of 231-Luc cells determined by MTS assay after incubation with PTX, Abraxane™, PLGA-PEG-PTX, or PLGA-PEG-ITEM4-PTX. After 2 hours, agents were removed and cells were incubated for an additional 24 hours. Values shown are mean+SD (n=3). Data were analyzed for significance between PLGA-PEG-ITEM4-PTX and all other groups using Student's t-test (*P<0.05).

In comparison, the PLGA-PEG-PTX and PLGA-PEG-ITEM4-PTX nanoparticles were cytotoxic, with the Fn14-targeted DART nanoparticles exhibiting the highest cytotoxic activity. Specifically, the IC50 value for PLGA-PEG-ITEM4-PTX nanoparticles was 0.13 µM in the in vitro clearance study while the IC50 values could not be determined for the other three agents using this dose range.

Figure 41A:
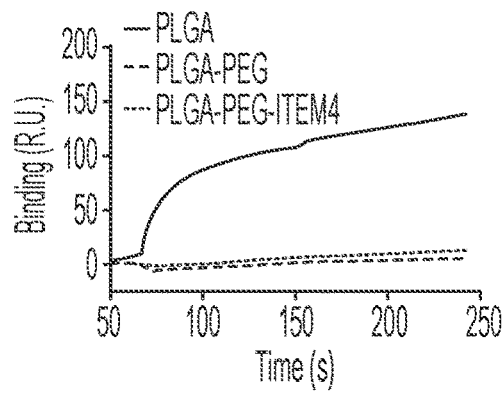
FIG. 41A through FIG. 41D show the properties of PTX-loaded DART nanoparticles and the effect of intratumoral delivery on 231-Luc tumor growth: non-specific binding analysis (FIG. 41A), multiple particle tracking analysis (FIG. 41B), tumor growth curves (FIG. 42C), and tumor doubling time (FIG. 41D)).

Example 31. DART Nanoparticles have Minimal Non-Specific Binding to Tumor ECM Proteins and Rapidly Penetrate TNBC Tumor Tissue Non-specific binding of various nanoparticle formulations to Matrigel™ (a tumor ECM preparation) was assessed using an SPR Biacore™ assay as previously described. PLGA-PEG and PLGA-PEG-ITEM4 did not bind appreciably to the Matrigel™ chip, suggesting minimal non-specific interactions between the nanoparticles and the tumor ECM proteins. See FIG. 41A, which shows non-specific binding analysis of nanoparticles to tumor ECM protein (Matrigel™)-coated Biacore™ chips using the surface plasmon resonance (SPR) technique (R.U.: Response Units). In contrast, PLGA nanoparticles without PEG coating showed some binding to the Matrigel™. PLGA-PEG-IgG nanoparticles were analyzed for their binding to the Matrigel™ Similar to the PLGA-PEG nanoparticles, PLGA-PEG-IgG did not bind to the Matrigel™ chip (FIG. 42). The non-specific binding of PS nanoparticles was assessed on the same Matrigel™ chip as a positive control for chip integrity. Binding of non-targeted PLGA-PEG-IgG nanoparticles to Matrigel™-coated Biacore™ chip compared to PS nanoparticles used as positive control (see FIG. 42).

Figure 41B:
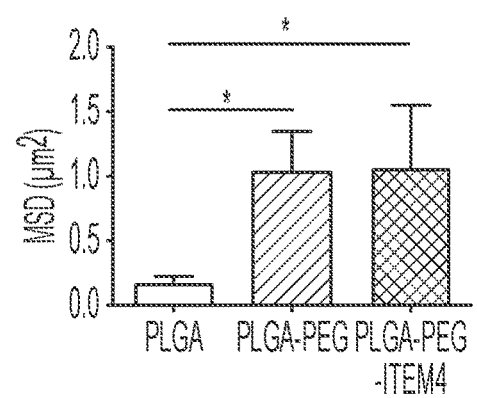

Diffusion rates of individual rhodamine-labeled nanoparticles were then analyzed ex vivo in 231-Luc tumor slices using MPT assays as described previously. The nanoparticle diffusion in terms of mean square displacement (MSD) at a time scale ($\tau$)=1 s for PLGA-PEG and PLGA-PEG-ITEM4 was significantly higher than PLGA nanoparticles without PEG coating. See FIG. 41B, which presents the multiple particle tracking (MPT) analysis of nanoparticles in breast tumor slices ex vivo showing ensemble-averaged mean square displacements (MSD) as a function of time scale at 1 sec time point. Values shown are mean±SD (n=5). Data were analyzed for significance using one-way ANOVA followed by Tukey HSD (*P<0.05). To analyze nanoparticle size effect on their diffusion in tumor slices, we normalized experimental MSD values by theoretical diffusion values of nanoparticles, which takes particle size into account. The diffusion rates of PLGA, PLGA-PEG, and PLGA-PEG-ITEM4 nanoparticles were 124-fold, 17-fold, and 15-fold lower, respectively, compared to their theoretical diffusion rates in water at $\tau$=1 s (Table 5). Although the calculated MSD of PLGA-PEG-ITEM4 nanoparticles was increased slightly compared to PLGA-PEG nanoparticles, there was no statistical difference between these two formulations. The MPT results suggest that dense PEG-coating on nanoparticles reduces the non-specific interactions between PLGA-PEG or PLGA-PEG-ITEM4 and the tumor ECM proteins. Moreover, conjugation of ITEM4 to the PLGA-PEG nanoparticles does not promote binding to the tumor ECM.

Figure 41C:
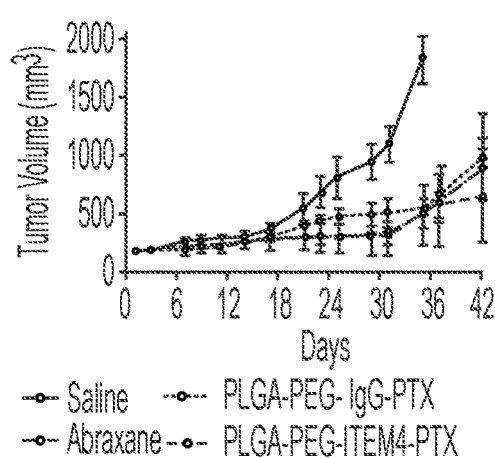

Example 32. Effect of Intra-Tumoral Delivery of PTX-Loaded DART Nanoparticles on 231-Luc Tumor Growth Human 231-Luc cells were implanted above the mammary fad of nude mice and 7 days later either saline, PLGA-PEG-IgG-PTX, PLGA-PEG-ITEM4-PTX, or the equivalent dose of PTX-albumin nanoparticles (Abraxane™) was delivered directly into the tumors. All mice were randomized so that the starting average tumor size was the same among all groups. All three PTX nanoparticle formulations inhibited tumor growth (see FIG. 41C). This figure shows tumor growth curves for mice treated with saline (n=5), Abraxane™ (n=5), PLGA-PEG-PTX (n=6) nanoparticles, or PLGA-PEG-ITEM4-PTX nanoparticles (n=6) by one intra-tumoral injection. Values are mean+SEM.

Figure 41D:
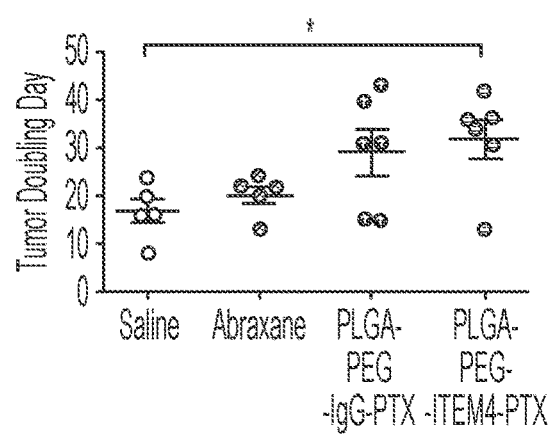

However, the average tumor doubling time in PLGA-PEG-IgG-PTX- or PLGA-PEG-ITEM4-PTX-treated mice was 28 days and 35 days, respectively, compared to 17 days for saline and 20 days for Abraxane™-treated mice (see FIG. 41D). This figure presents the tumor doubling time of individual mice from FIG. 41C, calculated from day 1 following treatment. Each point represents an individual mouse. Black horizontal bars represent mean and SEM. The data were analyzed for significance using one-way ANOVE with Tukey HSD (*P<0.05). In addition, the average tumor tripling time was calculated, there was a significant difference between the saline group and the PLGA-PEG-IgG-PTX or PLGA-PEG-ITEM4-PTX groups (data not shown).

Example 33. Effect of Systemic Delivery of PTX-loaded DART Nanoparticles on 231-Luc Orthotopic Tumor Targeting and Growth To determine if Fn14-targeted DART nanoparticles target and accumulate in Fn14-positive tumor cells in vivo, rhodamine-labeled PLGA-PEG-IgG or PLGA-PEG-ITEM4 DART nanoparticles were injected via the tail vein into mice bearing 231-Luc mammary fat pad tumors. The mice were euthanized 24 hours after nanoparticle injection, tumors were harvested, and fluorescence was analyzed using Xenogen™ imaging system. The tumor accumulation efficiency of PLGA-PEG-ITEM4 nanoparticles was about 2-fold higher than PLGA-PEG-IgG (see FIG. 43A and FIG. 43B). FIG. 43A shows fluorescence images of 231-Luc tumors isolated from mice 24 h after administration of rhodamine-labeled PLGA-PEG-IgG or PLGA-PEG-ITEM4 nanoparticles, while FIG. 43B presents analysis of fluorescence intensity from FIG. 43A. The same area of regions of interest (ROI) were used to obtain total radiance (photons/sec/cm2/sr) of the fluorescent tumor signals. Values shown are mean±SD (n=3). Data analyzed for significance using Student's t-test (**P<0.01).

PTX-loaded nanoparticles then were evaluated for antitumor activity in the orthotopic 231-Luc xenograft model. Mice with established 231-Luc tumors were randomized so that the starting average tumor volume was the same among all groups (150-200 mm3). Mice were treated once intravenously with either saline, Abraxane™, PLGA-PEG-IgG-PTX, or PLGA-PEG-ITEM4-PTX DART nanoparticles at 10 mg/kg of PTX equivalent. The PLGA-PEG-ITEM4-PTX nanoparticles outperformed Abraxane™ and PLGA-PEG-IgG-PTX nanoparticles in reducing tumor growth (FIG. 43C), which correlated with a significant increase in animal survival (FIG. 43D). FIG. 43C provides the tumor growth curves for mice treated with saline (n=9), Abraxane™, PLGA-PEG-IgG-PTX, or PLGA-PEG-ITEM4-PTX (10 mg/kg PTX equivalent, n=9) by one intravenous injection. Values are mean+SEM. FIG. 43D presents data showing the cumulative survival of mice from FIG. 43C (Kaplan-Meier). Arrow indicates injection day.

Specifically, the median survival time for mice treated with saline was 37 days, which increased slightly to 45 days for mice treated with Abraxane™ (Kaplan-Meier, Wilcoxon test, P<0.01). Treatment with PLGA-PEG-IgG-PTX nanoparticles further increased the survival to 52 days (Kaplan-Meier, Wilcoxon test, P<0.001). In contrast, six out of nine mice were alive for up to 55 days after treatment with PLGA-PEG-ITEM4-PTX nanoparticles, and three of nine mice had no residual tumors (P<0.0001). These results demonstrate that treatment with DART nanoparticles (PLGA-PEG-ITEM4-PTX) significantly improved the survival of mice bearing mammary fat pad 231-Luc tumors over Abraxane™ (P<0.05) and PLGA-PEG-IgG-PTX (P<0.05).

Example 34. In Vivo Safety Profile of PTX-Loaded DART Nanoparticles

Concurrently with systemic delivery of PTX-loaded nanoparticles to determine orthotopic tumor growth effect, body weight was monitored for individual mice in each group to examine overt signs of organ toxicity. Mice were weighed on each day that tumor measurements were taken (every 2-3 days). No significant average weight difference was observed between mice in each group (FIG. 44A). On the day of euthanasia, which was predetermined as the day tumors reached a volume of 1800 mm$^3$, blood was collected. Some of the blood was used to prepare serum in order to conduct blood cell and hepatic enzyme analyses.
No significant differences in the various blood cell counts between the four groups (WBC, WBC differential, RBC, HGB, etc.) were observed (data not shown). Aspartate transaminase (AST; see FIG. 44B) and alanine transaminase (ALT; see FIG. 44C) levels were similar between the four groups, except for one mouse in the Abraxane™ group with high ALT levels (see FIG. 45B and FIG. 44C).

Example 35. Effect of Systemic Delivery of PTX-Loaded DART Nanoparticles on 231-Br-Luc Tumor Growth in the Mouse Brain Since brain metastasis occurs in ~30% of TNBC patients and leads to significant mortality, the therapeutic efficacy of our DART nanoparticles was tested on 231-Br-Luc ("brain-seeking" TNBC cells) tumors residing in the brain. For these tests, MDA-MB-231-Br6-luc "brain-seeking" cells (which survive and proliferate in the brain microenvironment) were used. These cells express Fn14 and are sensitive to PTX treatment in vitro (FIG. 46A). FIG. 45A shows the viability of 231-Br-Luc cells determined by MTS assay after 24 hours' incubation with various PTX concentrations.

To investigate if DART nanoparticles could traffic to 231-Br-Luc tumors residing in the brain, intracranial tumor bearing mice were intravenously injected with rhodamine-labeled PLGA-PEG-IgG or PLGA-PEG-ITEM4 nanoparticles. Brains were harvested from mice 24 hours later and fluorescence was quantified using a Xenogen™ imaging system. Both nanoparticle formulations were detected in the brain but more fluorescence was present in harvested brains from mice that received the PLGA-PEG-ITEM4 DART nanoparticles. This difference, however, was not statistically significant (see FIG. 45B). FIG. 45B shows the fluorescence intensity of rhodamine-labeled nanoparticle accumulation in intracranial 231-Br-Luc tumors isolated from mice 24 hours after nanoparticle administration.

Example 36. Effect of Systemic Delivery of PTX-Loaded DART Nanoparticles on 231-Br-Luc Tumor Growth in the Mouse Brain Therapeutic efficacy of PTX-loaded nanoparticles then was assessed in mice bearing intracranial 231-Br-Luc tumors. The mice were randomized into four groups via BLI signal and on day 7 after tumor implantation, they were treated with either saline, Abraxane™, PLGA-PEG-IgG-PTX, or PLGA-PEG-ITEM4-PTX DART nanoparticles at 10 mg/kg of PTX equivalent. Mice were imaged once a week and body weights were measured every other day until the end of the experiment. Representative BLI images from mice included in the four treatment groups is shown in FIG. 46A.

Figure 46B:
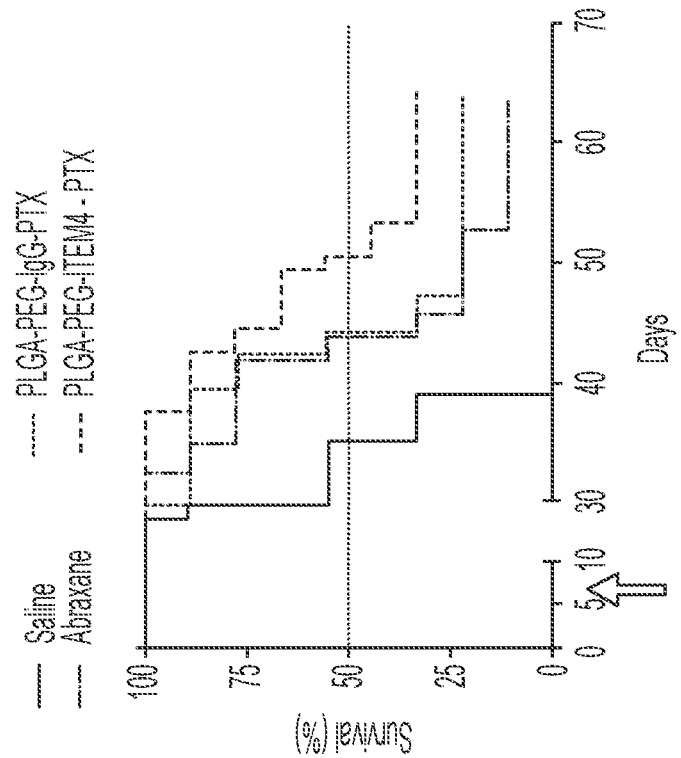
FIG. 46B shows the cumulative survival of mice from FIG. 46A (Kaplan-Meier). The arrow indicates injection day.
Figure 46A:
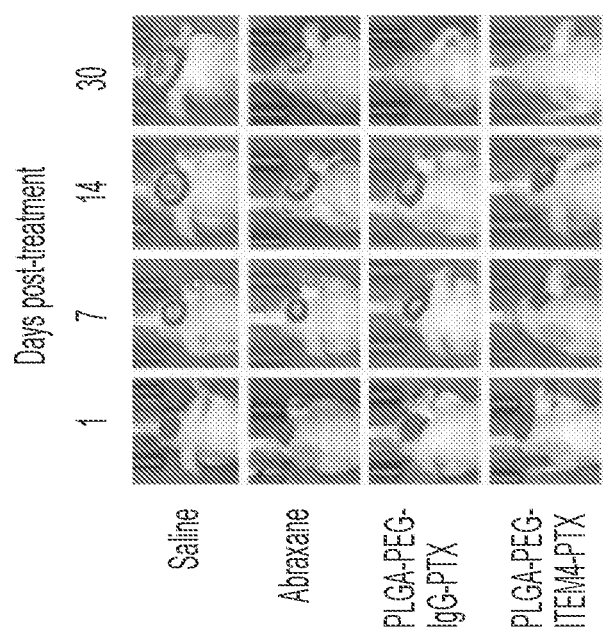
FIG. 46A shows BLI analysis over time of 231-Br-Luc intracranial tumor-bearing mice treated with either Saline (n=9), Abraxane™, PLGA-PEG-IgG-PTX nanoparticles, or PLGA-PEG-ITEM4-PTX nanoparticles (10 mg/kg PTX equivalent, n=9) by one intravenous injection.

The median survival time for mice treated with saline was 35 days, which was slightly increased to 44 days with Abraxane™ treatment (Kaplan-Meier, Wilcoxon test, P<0.01) (FIG. 46B). Treatment with PLGA-PEG-IgG-PTX did not further increase the median survival of 44 days compared to Abraxane™; however, two out of nine mice were still alive at the end of the study on day 64 and showed no residual tumors (Kaplan-Meier, Wilcoxon test, P<0.001). In contrast, treatment with PLGA-PEG-ITEM4-PTX nanoparticles further increased the median survival time to 50 days and three out of nine mice were alive at the end of the study on day 64 and showed no residual tumors (P<0.001). These results demonstrate that treatment with PTX-loaded DART nanoparticles can significantly reduce 231-Br-Luc intracranial tumor growth after one systemic administration.

REFERENCES

All references listed below and throughout the specification are hereby incorporated by reference in their entirety.
1. Allard et al., Convection-enhanced delivery of nano carriers for the treatment of brain tumors. Biomaterials, 30(12):2302-2318, 2009.
2. Anders et al., Pharmacokinetics and efficacy of PEGylated liposomal doxorubicin in an intracranial model of breast cancer. PLoS One 8(5):e61359, 2013.
3. Ausubel et al., Current Protocols in Molecular Biology, Greene Publishing Associates (1992, and Supplements to 2002).

4. Baschnagel et al., Vorinostat enhances the radiosensitivity of a breast cancer brain metastatic cell line grown in vitro and as intracranial xenografts. Mol. Cancer Ther. 8(6): 1589-1595, 2009. Park, Facing the truth about nanotechnology in drug delivery. ACS Nano. 7(9):7442-7447, 2013.
5. Bernabeu et al., Paclitaxel-loaded PCL-TPGS nanoparticles: in vitro and in vivo performance compared with Abraxane®. Colloids Surf. B Biointerfaces 113:43-50, 2014.
6. Bertrand et al., Cancer nanotechnology: the impact of passive and active targeting in the era of modern cancer biology. Adv. Drug Deliv. Rev. 66:2-25, 2014.
7. Bhattacharyya et al., A paclitaxel-loaded recombinant polypeptide nanoparticle outperforms Abraxane in multiple murine cancer models. Nat. Commun. 6:7939, 2015.
8. Blanco et al., Principles of nanoparticle design for overcoming biological barriers to drug delivery. Nat. Biotechnol. 33(9):941-951, 2015.
9. Bobo et al., Convection-enhanced delivery of macromolecules in the brain. Proc. Natl. Acad. Sci. USA, 91(6): 2076-80, 1994.
10. Bonelli and Hofmann, Expert Opin. Pharmacother. 5, 767-776, 2004.
11. Brem et al., Placebo-controlled trial of safety and efficacy of intraoperative controlled delivery by biodegradable polymers of chemotherapy for recurrent gliomas. The Polymer-brain Tumor Treatment Group. Lancet, 345 (8956):1008-1012, 1995.
12. Brown et al., TWEAK binding to the Fn14 cysteine-rich domain depends on charged residues located in both the A1 and D2 modules. Biochem. J., 397(2):297-304, 2006.
13. Bruce et al., Regression of recurrent malignant gliomas with convection-enhanced delivery of topotecan. Neurosurgery, 69(6):1272-1280, 2011.
14. Cabral et al., Nat. Nanotechnol. 6:815-823, 2011.
15. Chauhan et al., Annu. Rev. Chem. Biomol. Eng. 2:281-98, 2011.
16. Cheng et al., TWEAK/Fn14 Axis-Targeted Therapeutics: Moving Basic Science Discoveries to the Clinic. Front. Immunol., 4:473, 2013.
17. Cheng et al., The TWEAK Receptor Fn14 Is an Src-Inducible Protein and a Positive Regulator of Src-Driven Cell Invasion. Mol. Cancer Res., 13(3):575-583, 2015.
18. Cheng et al., Multifunctional nanoparticles: cost versus benefit of adding targeting and imaging capabilities. Science 338(6109):903-910, 2012.
19. Chao et al., Expression of TweakR in breast cancer and preclinical activity of enavatuzumab, a humanized anti-TweakR mAb. J. Cancer Res. Clin. Oncol. 139(2):315-325, 2013.
20. Chauhan et al., Delivery of molecular and nanoscale medicine to tumors: transport barriers and strategies. Annu. Rev. Chem. Biomol. Eng. 2:281-298, 2011.
21. Chauhan and Jain, Strategies for advancing cancer nanomedicine. Nat. Mater. 12(11):958-962, 2013.
22. Coleman and Ribchester, Current Drug Targets —CNS & Neurological Disorders, 3:153-160, 2004 Bentham Science Publishers Ltd; and Programmed Axon Death, Synaptic Dysfunction and the Ubiquitin Proteasome System.
23. Dancy et al., Non-specific binding and steric hindrance thresholds for penetration of particulate drug carriers within tumor tissue. J. Control Release 238:139-148, 2016.
24. Danhier et al., PLGA-based nanoparticles: an overview of biomedical applications. J. Control Release 161(2): 505-522, 2012.
25. Davis et al., Nanoparticle therapeutics: an emerging treatment modality for cancer. Nat. Rev. Drug Discov. 7(9):771-782, 2008.
26. de Plater et al., Predictive gene signature of response to the anti-TweakR mAb PDL192 in patient-derived breast cancer xenografts. PLoS One 9(11):e104227, 2014.
27. Dent et al., Pattern of metastatic spread in triple-negative breast cancer. Breast Cancer Res. Treat. 115(2):423-428, 2009.
28. Dhruv et al., Structural basis and targeting of the interaction between fibroblast growth factor-inducible 14 and tumor necrosis factor-like weak inducer of apoptosis. J. Biol. Chem., 288(45):32261-32276, 2013.
29. Do et al., Ex vivo Evans blue assessment of the blood brain barrier in three breast cancer brain metastasis models. Breast Cancer Res. Treat. 144(1):93-101, 2014.
30. Dreaden et al., Tumor-Targeted Synergistic Blockade of MAPK and PI3K from a Layer-by-Layer Nanoparticle. Clin. Cancer Res. 21(19):4410-4419, 2015.
31. Duncan and Gaspar, Nanomedicine(s) under the microscope. Mol. Pharm., 8(6):2101-2141, 2011.
32. Ensign et al., Mucus-penetrating nanoparticles for vaginal drug delivery protect against herpes simplex virus. Sci. Transl. Med., 4(138):138ra79, 2012.
33. Fauci et al., Harrison's Principles of Internal Medicine, McGraw-Hill, 14th Edition (1998), page 2321.
34. Feng et al., The Fn14 immediate-early response gene is induced during liver regeneration and highly expressed in both human and murine hepatocellular carcinomas. Am. J. Pathol. 156:1253-1261, 2000.
35. Fortin et al., Tumor necrosis factor-like weak inducer of apoptosis stimulation of glioma cell survival is dependent on Akt2 function. Mol. Cancer Res., 7(11):1871-1881, 2009.
36. Foulkes et al., Triple-negative breast cancer. N. Engl. J. Med. 363(20):1938-1948, 2010.
37. Fung et al., Chemother apeutic drugs released from polymers: distribution of 1,3-bis(2-chloroethyl)-1-nitrosourea in the rat brain. Pharm. Res., 13(5):671-682, 1996.
38. Gradishar et al., Phase III trial of nanoparticle albumin-bound paclitaxel compared with polyethylated castor oil-based paclitaxel in women with breast cancer. J. Clin. Oncol. 23(31):7794-7803, 2005.
39. Gref et al., Biodegradable long-circulating polymeric nanospheres. Science 263(5153):1600-1603, 1994.
40. Guarneri et al., Relapsed triple-negative breast cancer: challenges and treatment strategies. Drugs 73(12): 125712-65, 2013.
41. Gurunathan et al., Regulation of fibroblast growth factor-inducible 14 (Fn14) expression levels via ligand-independent lysosomal degradation. J. Biol. Chem., 289(19): 12976-12988, 2014.
42. Hadjipanayis et al., EGFRvIII antibody-conjugated iron oxide nanoparticles for magnetic resonance imaging-guided convection-enhanced delivery and targeted therapy of glioblastoma. Cancer Res., 70(15):6303-6312, 2010.
43. Hamaguchi et al., NK105, a paclitaxel-incorporating micellar nanoparticle formulation, can extend in vivo antitumour activity and reduce the neurotoxicity of paclitaxel. Br. J. Cancer 92(7):1240-1246, 2005.

44. Harlow and Lan, Antibodies: A Laboratory Manual, Cold Spring Harbor Laboratory Press, Cold Spring Harbor, N.Y. (1990).
45. Harries et al., Nanoparticle albumin-bound paclitaxel for metastatic breast cancer. J. Clin. Oncol. 23(31):7768-7771, 2005.
46. He et al., Blood-brain barrier-penetrating amphiphilic polymer nanoparticles deliver docetaxel for the treatment of brain metastases of triple negative breast cancer. J. Control Release 246:98-109, 2017.
47. Hersh et al., The TNF Receptor Family Member Fn14 is Highly Expressed in Recurrent Glioblastoma (GBM) and in GBM Patient-Derived Xenografts With Acquired Temozolomide Resistance. Neurol. Oncol., 2018.
48. Hu et al., TWEAK/Fn14 signaling in tumors. Tumour Biol. 39(6):1010428317714624, 2017.
49. Huang et al., Overexpression of Fn14 promotes androgen-independent prostate cancer progression through MMP-9 and correlates with poor treatment outcome. Carcinogenesis 32(11):1589-1596, 2011.
50. Jain et al., Nat. Rev. Clin. Oncol. 7(11):653-664, 2010.
51. Jain, Nanobiotechnology-based strategies for crossing the blood-brain barrier. Nanomedicine (Lond), 7(8):1225-1233, 2012.
52. Jain and Stylianopoulos, Delivering nanomedicine to solid tumors. Nat. Rev. Clin. Oncol. 7(11):653-664, 2010.
53. Johnston et al., Targeting of Fn14 Prevents Cancer-Induced Cachexia and Prolongs Survival. Cell, 162(6):1365-78, 2015.
54. Kabraji et al., Drug Resistance in HER2-Positive Breast Cancer Brain Metastases: Blame the Barrier or the Brain? Clin. Cancer Res. 24(8):1795-1804, 2018.
55. Kandel, Schwart, Jessell, editors. Principles of Neural Science, 4th ed. McGraw-Hill/Appleton & Lange: New York, N. Y. (2000).
56. Karmali et al., Targeting of albumin-embedded paclitaxel nanoparticles to tumors. Nanomed. 5(1):73-82, 2009.
57. Karpuj, et al., Nat. Med., 8:143-149, 2002.
58. Kassam et al., Survival outcomes for patients with metastatic triple-negative breast cancer: implications for clinical practice and trial design. Clin. Breast Cancer 9(1):29-33, 2009.
59. Kennecke et al., Metastatic behavior of breast cancer subtypes. J. Clin. Oncol. 28(20):3271-3277, 2010.
60. Kim et al., Highly compacted pH-responsive DNA nanoparticles mediate transgene silencing in experimental glioma. J. Mater. Chem. B, 2:8165-8173, 2014.
61. Kim et al., Use of single-site-functionalized PEG dendrons to prepare gene vectors that penetrate human mucus barriers. Angew. Chem. Int. Ed. Engl., 52(14):3985-3988, 2013.
62. Kodack et al., Emerging strategies for treating brain metastases from breast cancer. Cancer Cell. 27(2):163-175, 2015.
63. Kroll and Neuwelt, Outwitting the blood-brain barrier for therapeutic purposes: osmotic opening and other means. Neurosurgery, 42(5):1083-1100, 1998.
64. Kundranda and Niu, Albumin-bound paclitaxel in solid tumors: clinical development and future directions. Drug Des. Devel. Ther. 9:3767-3777, 2015.
65. Kunwar et al., Phase III randomized trial of CEO of IL13-PE38QQR vs Gliadel wafers for recurrent glioblastoma. Neurol. Oncol., 12(8):871-881, 2010.
66. Kwon et al., Elevated fibroblast growth factor-inducible 14 expression promotes gastric cancer growth via nuclear factor-KB and is associated with poor patient outcome. Cancer Lett. 314(1):73-81, 2012.
67. Lai et al., Rapid transport of large polymeric nanoparticles in fresh undiluted human mucus. Proc. Natl. Acad. Sci. USA, 104(5):1482-7, 2007.
68. Lee et al., Stat3 orchestrates interaction between endothelial and tumor cells and inhibition of Stat3 suppresses brain metastasis of breast cancer cells. Oncotarget. 6(12):10016-10029, 2015.
69. Lehmann et al., Identification of human triple-negative breast cancer subtypes and preclinical models for selection of targeted therapies. J. Clin. Invest. 121(7):2750-2767, 2011.
70. Li et al., Prevention of antibody-mediated elimination of ligand-targeted liposomes by using poly(ethylene glycol)-modified lipids. J. Pharm. Exp. Ther. 300(3):976-983, 2002.
71. Li et al., Deep penetration of nanoparticulate drug delivery systems into tumors: challenges and solutions. Curr. Med. Chem. 20(23):2881-2891, 2013.
72. Li et al., A multifunctional polymeric nanotheranostic system delivers doxorubicin and imaging agents across the blood-brain barrier targeting brain metastases of breast cancer. ACS Nano. 8(10):9925-9940, 2014.
73. Li et al., Novel Strategy Utilizing Extracellular Cysteine-Rich Domain of Membrane Receptor for Constructing d-Peptide Mediated Targeted Drug Delivery Systems: A Case Study on Fn14. Bioconjug. Chem. 28(8):2167-2179, 2017.
74. Lim et al., Phase I pharmacokinetic study of a weekly liposomal paclitaxel formulation (Genexol-PM) in patients with solid tumors. Ann. Oncol., 21(2):382-388, 2010.
75. Lluch et al., Treatment innovations for metastatic breast cancer: nanoparticle albumin-bound (NAB) technology targeted to tumors. Crit. Rev. Oncol. Hematol. 89(1):62-72, 2014.
76. Lockman et al., Heterogeneous blood-tumor barrier permeability determines drug efficacy in experimental brain metastases of breast cancer. Clin. Cancer Res. 16(23):5664-5678, 2010.
77. Madhankumar et al., Interleukin-13 receptor-targeted nanovesicles are a potential therapy for glioblastoma multiforme. Mol. Cancer Ther., 5(12):3162-3169, 2006.
78. Maeda et al., Adv. Drug Deliv. Rev., 65:71-79, 2013.
79. Martinez-Aranda et al., Predictive and Prognostic Brain Metastases Assessment in Luminal Breast Cancer Patients: FN14 and GRP94 from Diagnosis to Prophylaxis. Front. Oncol. 7:283, 2017.
80. Medberry et al., Hydrogels derived from central nervous system extracellular matrix. Biomaterials, 34(4):1033-40, 2013.
81. Meighan-Mantha et al., The mitogen-inducible Fn14 gene encodes a type I transmembrane protein that modulates fibroblast adhesion and migration. J. Biol. Chem. 274:33166-33176, 1999.
82. Michaelson et al., Tweak induces mammary epithelial branching morphogenesis. Oncogene 24:2613-2624, 2005.
83. Miele et al., Albumin-bound formulation of paclitaxel (Abraxane ABI-007) in the treatment of breast cancer. Int. J. Nanomedicine 4:99-105, 2009.
84. Miller-Kleinhenz et al., Targeted nanoparticles for image-guided treatment of triple-negative breast cancer: clinical significance and technological advances. Wiley Interdiscip. Rev. Nanomed. Nanobiotechnol. 7(6):797-816, 2015.

85. Mohamed et al., Targeted therapy for breast cancer. Am. J. Pathol. 183(4):1096-1112, 2013.
86. Morshed et al., Cell-Penetrating Peptide-Modified Gold Nanoparticles for the Delivery of Doxorubicin to Brain Metastatic Breast Cancer. Mol. Pharm. 13(6):1843-1854, 2016.
87. Murphy et al., Targeted nanogels: a versatile platform for drug delivery to tumors. Mol. Cancer Ther. 10(6):972-982, 2011.
88. Nadeau, Parkinson's Disease, J. Am. Ger. Soc., 45:233-240, 1997.
89. Nakayama et al., Fibroblast growth factor-inducible 14 mediates multiple pathways of TWEAK-induced cell death. J. Immunol., 170(1):341-348, 2008.
90. Nance et al., Non-invasive delivery of stealth, brain-penetrating nanoparticles across the blood-brain barrier using MRI-guided focused ultrasound. J. Control Release, 189:123-132, 2014.
91. Nance et al., A dense poly(ethylene glycol) coating improves penetration of large polymeric nanoparticles within brain tissue. Sci. Transl. Med. 4(149):149ra119, 2012.
92. Nikolaev, McLaughlin, O'Leary, Tessier-Lavigne. APP binds DR6 to cause axon pruning and neuron death via distinct caspases. Nature. 457 (7232): 981-989, 2009. doi: 10.1038/nature07767. PMJD 19225519.
93. Nyman et al., Phase I and pharmacokinetics trial of ABI-007, a novel nanoparticle formulation of paclitaxel in patients with advanced nonhematologic malignancies. J. Clin. Oncol. 23(31):7785-7793, 2005.
94. O'Reilly et al., The fate of chemoresistance in triple negative breast cancer (*TNBC*). Elsevier: BBA Clinical. p. 257-275. 30, 2015.
95. O'Shaughnessy et al., Nab-paclitaxel for first-line treatment of patients with metastatic breast cancer and poor prognostic factors: a retrospective analysis. Breast Cancer Res. Treat. 138(3):829-837, 2013.
96. Owens and Peppas, Opsonization, biodistribution, and pharmacokinetics of polymeric nanoparticles. Int. J. Pharm., 307(1):93-102, 2006.
97. Pang et al., Enhanced intracellular delivery and chemotherapy for glioma rats by transferrin-conjugated biodegradable polymersomes loaded with doxorubicin. Bioconjug. Chem., 22(6):1171-1180, 2011.
98. Patil et al., MRI virtual biopsy and treatment of brain metastatic tumors with targeted nanobioconjugates: nanoclinic in the brain. ACS Nano. 9(5):5594-5608, 2015.
99. Paulmurugan et al., Folate Receptor-Targeted Polymeric Micellar Nanocarriers for Delivery of Orlistat as a Repurposed Drug against Triple-Negative Breast Cancer. Mol. Cancer Ther. 15(2):221-231, 2016.
100. Perez et al., The TWEAK receptor Fn14 is a potential cell surface portal for targeted delivery of glioblastoma therapeutics. Oncogene 35(17):2145-2155, 2016.
101. Perou, Molecular stratification of triple-negative breast cancers. Oncologist 16 Suppl 1:61-70, 2011.
102. Pestalozzi et al., Identifying breast cancer patients at risk for Central Nervous System (CNS) metastases in trials of the International Breast Cancer Study Group (IBCSG). Ann. Oncol. 17(6):935-944, 2006.
103. Playfer, Parkinson's Disease, Postgrad. Med. J., 73:257-264, 1997.
104. Popielarski et al., A nanoparticle-based model delivery system to guide the rational design of gene delivery to the liver. 1. Synthesis and characterization. Bioconjug. Chem., 16(5):1063-70, 2005.
105. Prabhakar et al., Cancer Res. 73(8):2412-7, 2016.
106. Reardon et al., Phase II trial of murine (131)I-labeled antitenascin monoclonal antibody 81 C6 administered into surgically created resection cavities of patients with newly diagnosed malignant gliomas. J. Clin. Oncol., 20(5):1389-1397, 2002.
107. Rich and Bigner, Development of novel targeted therapies in the treatment of malignant glioma. Nat. Rev. Drug Discov., 3(5):430-446, 2004.
108. Ruoslahti et al., Targeting of drugs and nanoparticles to tumors. J. Cell. Biol. 188(6):759-768, 2010.
109. Salhia et al., Integrated genomic and epigenomic analysis of breast cancer brain metastasis. PLoS One 9(1): e85448, 2014.
110. Salvati et al., Transferrin-functionalized nanoparticles lose their targeting capabilities when a biomolecule corona adsorbs on the surface. Nat. Nanotechnol. 8(2):137-143, 2013.
111. Sambrook et al. Molecular Cloning: A Laboratory Manual, 2d ed., Cold Spring Harbor Laboratory Press, Cold Spring Harbor, N.Y. (1989).
112. Sampson et al., Poor drug distribution as a possible explanation for the results of the PRECISE trial. J. Neurosurg., 113(2):301-309, 2010.
113. Sampson et al., Immunologic escape after prolonged progression-free survival with epidermal growth factor receptor variant III peptide vaccination in patients with newly diagnosed glioblastoma. J. Clin. Oncol., 28(31): 4722-4729, 2010.
114. Sanz-Pamplona et al., Expression of endoplasmic reticulum stress proteins is a candidate marker of brain metastasis in both ErbB-2+ and ErbB-2-primary breast tumors. Am. J. Pathol. 179(2):564-579, 2011.
115. Sapra and Allen, Internalizing antibodies are necessary for improved therapeutic efficacy of antibody-targeted liposomal drugs. Cancer Res. 62(24):7190-7194, 2002.
116. Schneider et al., Minimizing the non-specific binding of nanoparticles to the brain enables active targeting of Fn14-positive glioblastoma cells. Biomaterials 42:42-51, 2015.
117. Schneider et al., Surface plasmon resonance as a high throughput method to evaluate specific and non-specific binding of nanotherapeutics. J. Control Release 219:331-344, 2015.
118. Schuster et al., Overcoming the cystic fibrosis sputum barrier to leading adeno-associated virus gene therapy vectors. Mol. Ther. 22(8):1484-1493, 2014.
119. Sharma et al., Paclitaxel-liposomes for intracavitary therapy of intraperitoneal P388 leukemia. Cancer Lett. 107(2):265-272, 1996.
120. Siegel et al., Cancer statistics, 2018. CA Cancer J. Clin. 68(1):7-30, 2018.
121. Sparreboom et al., Comparative preclinical and clinical pharmacokinetics of a cremophor-free, nanoparticle albumin-bound paclitaxel (ABI-007) and paclitaxel formulated in Cremophor (Taxol). Clin. Cancer Res. 11(11): 4136-4143, 2005.
122. Stead et al., Triple-negative breast cancers are increased in black women regardless of age or body mass index. Breast Cancer Res. 11(2):R18, 2009.
123. Stupp et al., Radiotherapy plus concomitant and adjuvant temozolomide for glioblastoma. N.E.J.M., 352(10): 987-996, 2005.
124. Stylianopoulos and Jain, Design considerations for nanotherapeutics in oncology. Nanomedicine, 2015.
125. Su et al., Conditional internalization of PEGylated nanomedicines by PEG engagers for triple negative breast cancer therapy. Nat. Commun. 8:15507, 2017.

126. Sugahara et al., Tissue-penetrating delivery of compounds and nanoparticles into tumors. Cancer Cell 16(6): 510-520, 2009.
127. Suk et al., PEGylation as a strategy for improving nanoparticle-based drug and gene delivery. Adv. Drug Deliv. Rev. 99(Pt A):28-51, 2016.
128. Sykova and Nicholson, Diffusion in brain extracellular space. Physiol. Rev., 88(4):1277-1340, 2008.
129. Tate and Aghi, Biology of angiogenesis and invasion in glioma. Neurotherapeutics, 6(3):447-457, 2009.
130. Tietjen et al., Focus on Fundamentals: Achieving Effective Nanoparticle Targeting. Trends Mol. Med. 24(7):598-606, 2018.
131. Tobias et al., The art of gene therapy for glioma: a review of the challenging road to the bedside. J. Neurol. Neurosurg. Psychiatry, 84(2):213-222, 2013.
132. Torre et al., Global cancer statistics, 2012. CA Cancer J. Clin., 65(2):87-108, 2015.
133. Tran et al., Increased fibroblast growth factor-inducible 14 expression levels promote glioma cell invasion via Rac1 and nuclear factor-kappaB and correlate with poor patient outcome. Cancer Res., 66(19):9535-9542, 2006.
134. Tzeng and Green, Therapeutic nanomedicine for brain cancer. Ther. Deliv, 4(6):687-704, 2013.
135. Ulbrich et al., Transferrin- and transferrin-receptor-antibody-modified nanoparticles enable drug delivery across the blood-brain barrier (BBB). Eur. J. Pharm. Biopharm., 71(2):251-256, 2009.
136. Vargova et al., Diffusion parameters of the extracellular space in human gliomas. Glia, 42(1):77-88, 2003.
137. Veiseh et al., Specific targeting of brain tumors with an optical/magnetic resonance imaging nanoprobe across the blood-brain barrier. Cancer Res., 69(15):6200-6207, 2009.
138. Voges et al., Clinical protocol. Liposomal gene therapy with the herpes simplex thymidine kinase gene/ganciclovir system for the treatment of glioblastoma multiforme. Hum. Gene Ther., 13(0.5):675-685, 2002.
139. Voges et al., Imaging-guided convection-enhanced delivery and gene therapy of glioblastoma. Ann. Neurol., 54(4):479-487, 2003.
140. Vykhodtseva et al., Progress and problems in the application of focused ultrasound for blood-brain barrier disruption. Ultrasonics, 48(4):279-296, 2008.
141. Wadajkar et al., Decreased non-specific adhesivity, receptor targeted (DART) nanoparticles exhibit improved dispersion, cellular uptake, and tumor retention in invasive gliomas. J. Control Release 267:144-153, 2017.
142. Wang et al., ACS Nano. 9:7195-7206, 2015.
143. Wang et al., Nanoparticle delivery of cancer drugs. Annu. Rev. Med. 63:185-198, 2012.
144. Wen, and Kesari, Malignant gliomas in adults. N.E.J.M., 359(5):492-507, 2008.
145. Whitsett et al., Elevated expression of Fn14 in non-small cell lung cancer correlates with activated EGFR and promotes tumor cell migration and invasion. Am. J. Pathol., 181(1):111-20, 2012.
146. Whitsett et al., FN14 expression correlates with MET in NSCLC and promotes MET-driven cell invasion. Clin. Exp. Metastasis 31(6):613-623, 2014.
147. Wicki et al., J. Control. Release 200:138-57, 2015.
148. Willis et al., The fibroblast growth factor-inducible 14 receptor is highly expressed in HER2-positive breast tumors and regulates breast cancer cell invasive capacity. Mol. Cancer Res., 6(5):725-734, 2008.
149. Winkles, The TWEAK-Fn14 cytokine-receptor axis: discovery, biology and therapeutic targeting. Nat. Rev. Drug Discov., 7(5):411-425, 2008.
150. Witzel et al., Breast cancer brain metastases: biology and new clinical perspectives. Breast Cancer Res. 18(1):8, 2016.
151. Wong et al., Nanotechnological advances for the delivery of CNS therapeutics. Adv. Drug Deliv. Rev. 64(7): 686-700, 2012.
152. Woodworth et al., Emerging insights into barriers to effective brain tumor therapeutics. Front. Oncol., 4:126, 2014.
153. Xu et al., Cancer nanomedicine: from targeted delivery to combination therapy. Trends Mol. Med. 21(4):223-232, 2015.
154. Yadav et al., Systemic treatment strategies for triple-negative breast cancer. World J. Clin. Oncol. 5(2):125-133, 2014.
155. Yardley, nab-Paclitaxel mechanisms of action and delivery. J. Control Release 170(3):365-372, 2013.
156. Yin et al., AR-Regulated TWEAK-FN14 Pathway Promotes Prostate Cancer Bone Metastasis. Cancer Res., 74(16):4306-17, 2014.
157. Yoneda et al., A bone-seeking clone exhibits different biological properties from the MDA-MB-231 parental human breast cancer cells and a brain-seeking clone in vivo and in vitro. J. Bone Miner. Res. 16(8):1486-1495, 2001.
158. Zhou et al., Development and characterization of a potent immunoconjugate targeting the Fn14 receptor on solid tumor cells. Mol. Cancer Ther. 10(7):1276-1288, 2011.
159. Zhou et al., Antitumor activity of a humanized, bivalent immunotoxin targeting Fn14-positive solid tumors. Cancer Res., 73(14):4439-4450, 2013.
160. Zhou et al., The TWEAK receptor Fn14 is a therapeutic target in melanoma: immunotoxins targeting Fn14 receptor for malignant melanoma treatment. J. Invest. Dermatol. 133(4):1052-1062, 2013.
161. Zhou et al., Highly penetrative, drug-loaded nanocarriers improve treatment of glioblastoma. Proc. Natl. Acad. Sci. USA, 110(29):11751-11756, 2013.
162. Zhou et al., Development of human serine protease-based therapeutics targeting Fn14 and identification of Fn14 as a new target overexpressed in TNBC. Mol. Cancer Ther. 13(11):2688-2705, 2014.
163. Zhou et al., The TWEAK receptor Fn14 is a therapeutic target in melanoma: immunotoxins targeting Fn14 receptor for malignant melanoma treatment. J. Invest. Dermatol. 133(4):1052-1062, 2016.
164. Zhu et al., Age-Related Disparity in Immediate Prognosis of Patients with Triple-Negative Breast Cancer: A Population-Based Study from SEER Cancer Registries. PLoS One, 2015. 10(5): p. e0128345.
165. Zimmermann and Dours-Zimmermann, Extracellular matrix of the central nervous system: from neglect to challenge. Histochem. Cell. Biol., 130(4):635-53, 2008.

The invention claimed is:

1. A drug delivery nanoparticle for treatment of Fn14 receptor bearing cancer, comprising:
   a) a nanoparticle having a hydrodynamic diameter of about 4 nm to about 200 nm;
   b) a surface coating on the nanoparticle containing at least 3 polyethylene glycol molecules per 100 nm$^2$;
   c) a moiety that specifically binds to an Fn14 receptor on the cell surface of the cancer cell;
   d) an anti-cancer therapeutic agent.

2. A drug delivery nanoparticle of claim 1, wherein the diameter is about 100 nm.

3. A drug delivery nanoparticle of claim 1, wherein the surface coating on the nanoparticle contains about 5 to about 20 polyethylene glycol molecules per 100 nm$^2$.

4. A drug delivery nanoparticle of claim 1, wherein the moiety that specifically binds Fn14 receptor is an Fn14 antibody or binding fragment thereof.

5. A drug delivery nanoparticle of claim 4, wherein the antibody is a monoclonal antibody or fragment thereof.

6. A drug delivery nanoparticle of claim 5, wherein the monoclonal antibody is an ITEM4 antibody or fragment thereof.

7. The drug delivery nanoparticle of claim 1, wherein the anti-Fn14 antibody is selected from the group consisting of ITEM4, ITEM4-SH, ITEM4 scFv, and ITEM4 Fab.

8. The drug delivery nanoparticle of claim 1, wherein the moiety that specifically binds Fn14 receptor is present at a coating density of about 0.0006 molecules per 100 nm$^2$ to about 0.075 molecules per 100 nm$^2$.

9. The drug delivery nanoparticle of claim 1, wherein the nanoparticle contains poly(lactic-co-glycolic acid) (PLGA), the anti-Fn14 antibody is ITEM4 and the ITEM4 is present at a coating density about 0.03 to about 0.075 molecules per 100 nm$^2$.

10. The drug delivery nanoparticle of claim 1, wherein the anti-cancer agent is selected from the group consisting of cisiplatin, doxorubicin, etoposide, and paclitaxel.

11. The drug delivery nanoparticle of claim 1, wherein the Fn14 receptor bearing cancer is selected from the group consisting of a bladder, brain, breast, cervical, colorectal, esophageal, liver, lung, skin, ovarian, pancreatic, prostate, renal, testicular, bone, liver, and lymph node cell.

12. The drug delivery nanoparticle of claim 11, wherein the Fn14 receptor bearing cancer is glioblastoma or breast cancer.

13. The drug delivery nanoparticle of claim 1, wherein the nanoparticle penetrates extracellular matrix and the nanoparticle has minimal non-specific binding to extracellular matrix.

14. A pharmaceutical composition comprising a pharmaceutically acceptable vehicle and a drug delivery nanoparticle of claim 1.

15. A method of treating Fn14 receptor bearing cancer, comprising administering to a subject in need a therapeutically effective amount of the drug delivery nanoparticle of claim 1.

16. A method of treating Fn14 receptor bearing cancer, comprising administering to a subject in need a therapeutically effective amount of the pharmaceutical composition of claim 14.

* * * * *